United States Patent
John et al.

(10) Patent No.: US 10,618,899 B2
(45) Date of Patent: Apr. 14, 2020

(54) SUBSTITUTED [1,2,3]TRIAZOLO[4,5-D]PYRIMIDINES THAT LOWER STRESS-INDUCED P-TAU

(71) Applicant: Buck Institute for Research on Aging, Novato, CA (US)

(72) Inventors: Varghese John, Los Angeles, CA (US); Dale E. Bredesen, Novato, CA (US)

(73) Assignee: Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 15/548,402

(22) PCT Filed: Feb. 17, 2016

(86) PCT No.: PCT/US2016/018305
§ 371 (c)(1),
(2) Date: Aug. 2, 2017

(87) PCT Pub. No.: WO2016/134042
PCT Pub. Date: Aug. 25, 2016

(65) Prior Publication Data
US 2018/0346466 A1 Dec. 6, 2018

Related U.S. Application Data

(60) Provisional application No. 62/117,888, filed on Feb. 18, 2015.

(51) Int. Cl.
*A61K 31/519* (2006.01)
*C07D 487/04* (2006.01)
*C07D 471/04* (2006.01)
*A61P 25/28* (2006.01)

(52) U.S. Cl.
CPC ............ *C07D 487/04* (2013.01); *A61P 25/28* (2018.01); *C07D 471/04* (2013.01)

(58) Field of Classification Search
CPC ........................... A61K 31/519; C07D 487/04
USPC ........................................ 514/261.1; 544/254
See application file for complete search history.

(56) References Cited

U.S. PATENT DOCUMENTS

| | | | |
|---|---|---|---|
| 6,107,301 | A | 8/2000 | Aldrich et al. |
| 6,342,503 | B1 | 1/2002 | Aldrich et al. |
| 6,448,261 | B1 | 9/2002 | Bakthavatchalam et al. |
| 2001/0025042 | A1 | 9/2001 | Arvanitis et al. |

FOREIGN PATENT DOCUMENTS

| | | |
|---|---|---|
| EP | 1293213 A1 | 3/2003 |
| WO | WO 97/35539 A2 | 10/1997 |
| WO | WO 2004/037159 A2 | 5/2004 |
| WO | WO 2007/076055 A2 | 7/2007 |
| WO | WO 2014/047257 A2 | 3/2014 |

OTHER PUBLICATIONS

PCT International Search Report and Written Opinion dated Aug. 26, 2016 issued in PCT/US2016/018305.
PCT International Preliminary Report on Patentability dated Aug. 22, 2017 issued in PCT/US2016/018305.
EP Extended Search Report dated Jun. 29, 2018 issued in EP 16752995.7.
Alexieva, et al. (1994) "Anticytokinin Activity of 4-Substituted Triazolo[4,5-d]pyrimidines and 4-Substituted Pyrazolo[3,4-d]pyrimidines" *Journal of Plant Growth Regulation*, 13:123-129.
Garner, et al. (2004) "Corticotrophin Releasing Hormone: Chemistry and Recent Developments" *Australian Journal of Chemistry*, 57(5): 393-407.
Hull (1959) "The Synthesis of Some 9-Furfurylpurines and Some Related Heterocyclic Compounds." *Imperial Chemical Industries Limited, Pharmaceuticals Division*, Alderley Park, Macclesfield, Cheshire, 481-484.
Liu, et al. (2005) "Parallel Solution-Phase Synthesis of a 2,6,8,9-Tetrasubstituted Purine Library via a Sulfur Intermediate" *J. Comb. Chem.*, 7: 627-636.
Miyashita, et al. (1991) "Ring Transformation of Condensed Pyrimidines by Enamines and Ynamines. Formation of Condensed Pyridines and Condensed Diazocines" *Chem. Pharm. Bull*, 39(2): 282-287.
Sergiev, et al. (2007) "Influence of cytokinins and novel cytokinin antagonists on the senescence of detached leaves of *Arabidopsis thaliana.*" *Biologia PlantarumLANTARUM*, 51 (2): 377-380.
Rissman, R. A. et al., "Corticotropin-Releasing Factor Receptors Differentially Regulate Stress-Induced Tau Phosphorylation," The Journal of Neuroscience 27(24): 6552-6562 (2007).
Campbell, S. N. et al., "Increased Tau Phosphorylation and Aggregation in Mice Overexpressing Corticotropin Releasing Factor," J Alzheimers Dis., 43(3): 967-976 (2015).
Office Action from corresponding Chinese Application No. 2016800174566 dated Nov. 13, 2019.
Office Action from corresponding Japanese Application No. 2017543785 dated Dec. 2, 2019.

*Primary Examiner* — Douglas M Willis
(74) *Attorney, Agent, or Firm* — Harness Dickey & Pierce P.L.C.

(57) ABSTRACT

Various [1,2,3]triazolo[4,5-d]pyrimidines are provided that are effective to lower p-tau and/or to prevent or reduce elevation of p-tau, particularly in response to stress (e.g., elevated cortisol levels). The compounds are useful in the treatment or prophylaxis of pathologies characterized by abnormal amyloid plaque and or tangle formation and/or deposition.

11 Claims, 26 Drawing Sheets

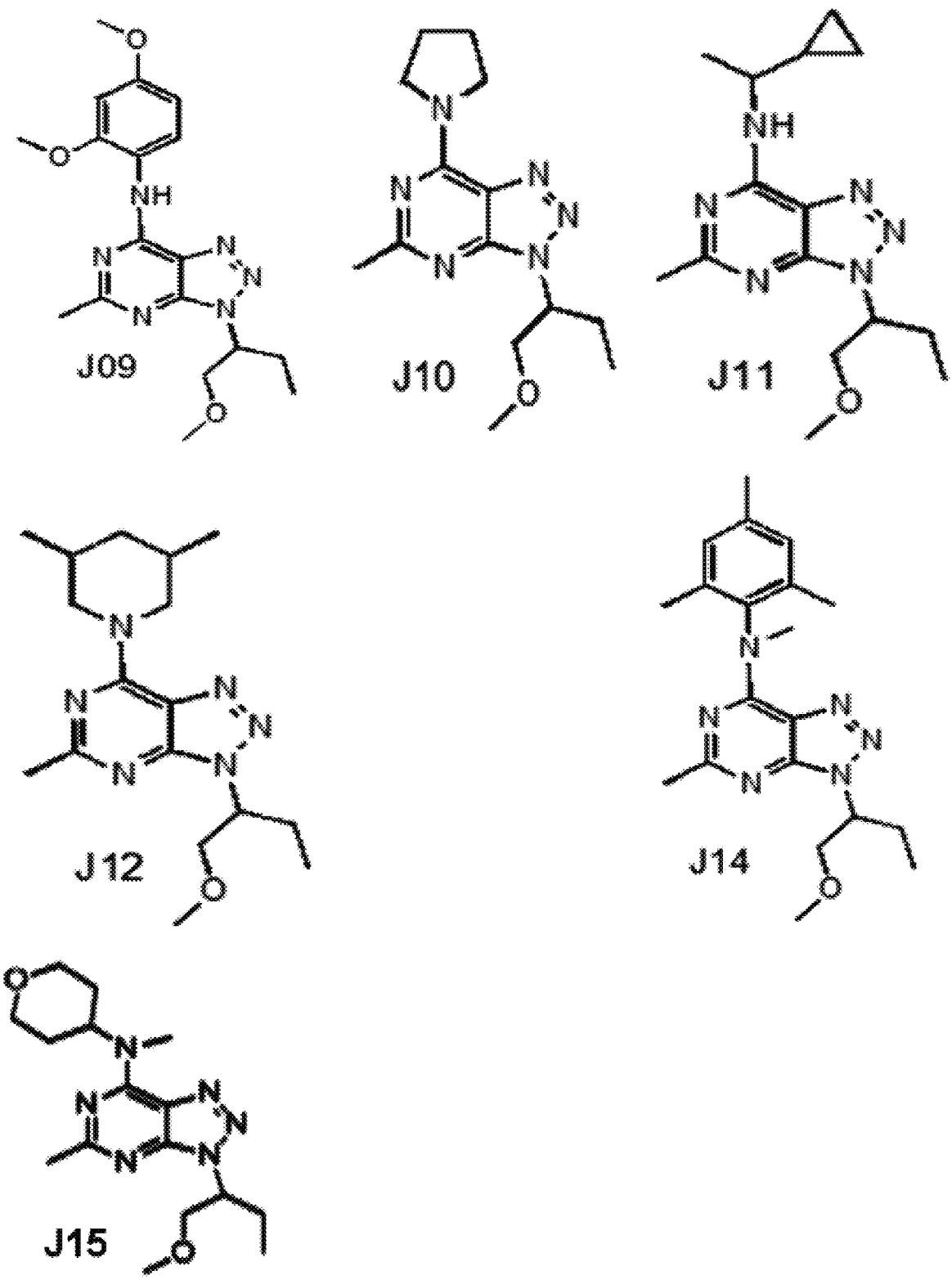
Fig. 2, cont'd.

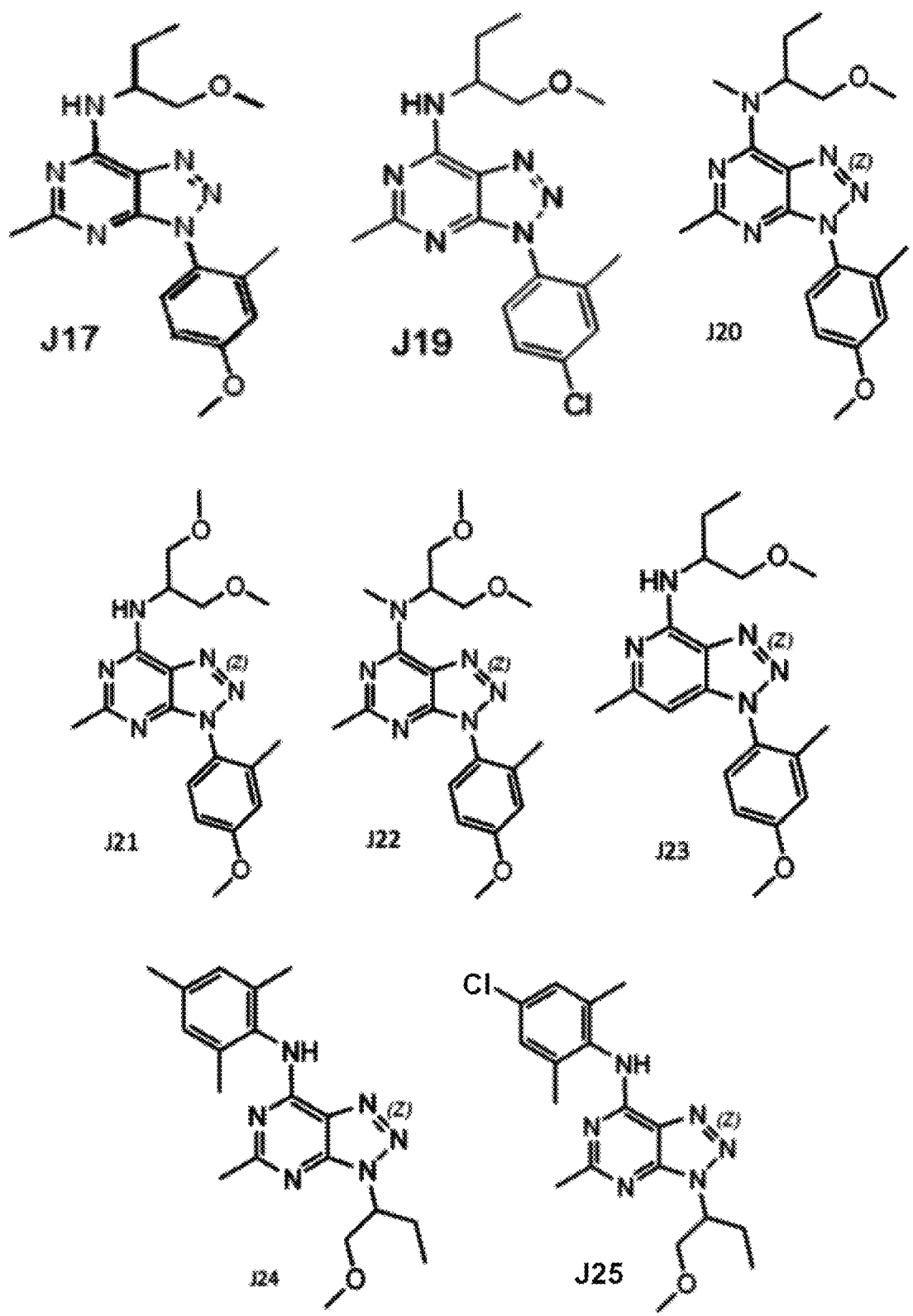
Fig. 2, cont'd.

A

J03

B

C

*In vitro*

SUBSTITUTED [1,2,3]TRIAZOLO[4,5-D]PYRIMIDINES THAT LOWER STRESS-INDUCED P-TAU

CROSS-REFERENCE TO RELATED APPLICATIONS

This application is a U.S. 371 National Phase of PCT/US2016/018305, filed on Feb. 17, 2016, which claims benefit of and priority to U.S. Ser. No. 62/117,888, filed Feb. 18, 2015, both of which are incorporated herein by reference in their entirety for all purposes.

STATEMENT OF GOVERNMENTAL SUPPORT

[Not Applicable]

BACKGROUND

Alzheimer's disease (AD) is estimated to afflict more than 20 million people worldwide and is believed to be the most common cause of dementia. As the World population ages, the number of people with Alzheimer's disease (AD), currently approximately 5.4 million in the United States, will continue to rise. Alzheimer's is a neurodegenerative disease associated with progressive dementia and memory loss. Two key characteristics of AD are the accumulation of extracellular deposits containing aggregated Aβ peptide and neuronal synaptic loss in the AD in specific brain regions. Although AD pathogenesis is complex, compelling genetic and biochemical evidence suggest that overproduction of Aβ, or failure to clear this peptide is the earliest event in the amyloid cascade that lead to AD primarily through amyloid deposition, which is presumed to be involved in neurofibrillary tangle formation, neuronal dysfunction and microglia activation, that characterize AD-affected brain tissues.

Neurofibrillary tangles, along with plaques comprised of Aβ peptide, are a pathological hallmark of Alzheimer's Disease (AD). Hyperphosphorylation of the microtubule-stabilizing protein tau leads to tangle formation. In people diagnosed with AD, and in our hands using the J20 mouse model of AD, the level of tau phosphorylation has the closest correlation to cognitive impairment. The reversal of tau pathology alone can improve memory, even in the presence of high Aβ42 in J20 mice (Roberson, et al. (2007) *Science*, 316(5825): 750-754). Even when Aβ plaque load is similar, reduction in tau expression and therefore tau pathology (tau-) increases performance in the Morris Water Maze. Tau pathology is "downstream" of Aβ formation in that Aβ increases expression of glycogen synthase kinase 3beta (GSK-3β), an enzyme that can increase phosphorylation of tau. The isoform of Aβ, whether soluble, oligomeric, and/or plaque-bound likely affects GSK-3β expression, therefore absolute AB level may not be directly related to p-tau level. Convergent evidence implicates stress in AD neuropathology (Carroll, et al. (2011) *J. Neurosci*. (40): 14436-14449). Stress exposure can increase Aβ production and induce deficits in hippocampal cell proliferation and contextual memory (Wilson et al. (2003) *Neurology*, 61: 1479-1485). Moreover, exposure to a variety of physiological stressors can activate tau kinases and induce tau phosphorylation (tau-P) in rodents (Dong et al. (2004) *Neurosci.*, 127: 601-609). The corticotropin releasing factor (CRF) signaling system plays a role in response to stress (Kang et al. (2007) *Proc. Natl. Acad. Sci. USA*, 104: 10673-10678).

SUMMARY

Various embodiments contemplated herein may include, but need not be limited to, one or more of the following:

Embodiment 1

A compound according to the formula:

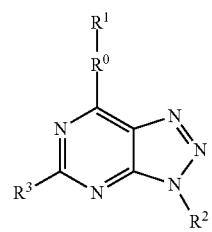

or a pharmaceutically acceptable salt thereof, wherein: $R^0$ is present or absent, and when present is selected from the group consisting of CHR, NH, O, and NCHR where R is H, alkyl (e.g., a C1-C6 carbon chain), or aryl (e.g., phenyl, substituted phenyl, or heteroaryl); $R^2$ is

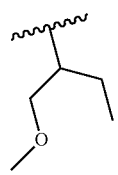 [SMILES: *C(CC)COC]

and $R^1$ is

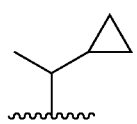

or is selected from the group consisting of a substituted or unsubstituted cyclic or heterocycle selected from the group consisting of pyridine, pyrimidine, naphthalene, quinolone, isoquinoline, cinnoline, phenyl, substituted phenyl, oxazole, furan, pyran, isoxazole, thiazole, thiophene, pyrole, pyrrolidine, pyrazole, and imidazole; or $R^1$ is

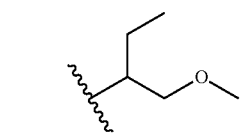 [SMILES: *C(CC)COC]

and $R^2$ is

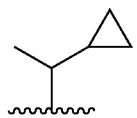 [SMILES: *C(C)C1CC1]

or is selected from the group consisting of a substituted or unsubstituted cyclic or heterocycle selected from the group consisting of pyridine, pyrimidine, naphthalene, quinolone, isoquinoline, cinnoline, phenyl, substituted phenyl, oxazole, furan, pyran, isoxazole, thiazole, thiophene, pyrole, pyrrolidine, pyrazole, and imidazole; and $R^3$ is selected from the group consisting of H, $CH_3$, ethyl, propyl, butyl, $CF_3$, $NH_2$, halogen, and $CH_2O$ where R is H, alkyl (e.g., C1-C6 carbon chain), or aryl (e.g., phenyl, substituted phenyl, or heteroaryl).

Embodiment 2

The compound of embodiment 1, wherein said compound is not one or more compounds selected from the group consisting of J03, J04, J05, J08, and J17.

Embodiment 3

The compound of embodiment 2, wherein said compound is not J03.

Embodiment 4

The compound according to any one of embodiments 2-3, wherein said compound is not J04.

Embodiment 5

The compound according to any one of embodiments 2-4, wherein said compound is not J05.

Embodiment 6

The compound according to any one of embodiments 2-5, wherein said compound is not J06.

Embodiment 7

The compound according to any one of embodiments 2-6, wherein said compound is not J17.

Embodiment 8

The compound according to any one of embodiments 1-7, wherein $R^1$ is

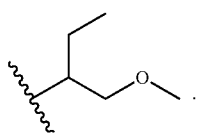 [SMILES: *C(CC)COC]

.

Embodiment 9

The compound of embodiment 8, wherein $R^2$ is

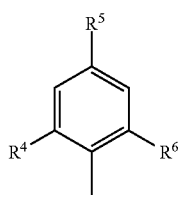

where $R^4$, $R^5$, and $R^6$ are independently selected from the group consisting of H, OH, halogen, methyl, and $OCH_3$, $CF_3$, ethyl, aryl, SR, $SO_2R$, NHCOR, and $CO_2R$, where R is H, alkyl (e.g., C1-C6 carbon chain), or aryl (e.g., phenyl, substituted phenyl, or heteroaryl).

Embodiment 10

The compound of embodiment 1, wherein $R^2$ is

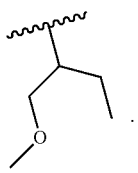 [SMILES: *C(CC)COC]

Embodiment 11

The compound of embodiment 10, wherein $R^1$ is

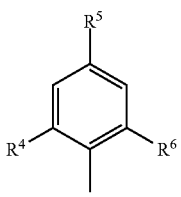

where $R^4$, $R^5$, and $R^6$ are independently selected from the group consisting of H, OH, halogen, methyl, $OCH_3$, $OCF_3$, $OCHF_2$, $N(CH_3)_2$, ethyl, propyl, butyl, NH-alkyl, O-alkyl, and $SO_2CH_3$.

Embodiment 12

The compound of embodiment 11, where $R^4$, $R^5$, and $R^6$ are independently selected from the group consisting of H, OH, halogen, methyl, and $OCH_3$.

Embodiment 13

The compound according to any one of embodiments 8-12, wherein $R^5$ is $OCH_3$.

Embodiment 14

The compound of embodiment 13, wherein $R^4$ is $CH_3$.

Embodiment 15

The compound of embodiment 13, wherein $R^4$ is $CH_3$ and $R^6$ is H.

Embodiment 16

The compound of embodiment 13, wherein $R^4$ is $OCH_3$.

Embodiment 17

The compound of embodiment 13, wherein $R^4$ is $OCH_3$ and $R^6$ is H.

Embodiment 18

The compound according to any one of embodiments 8-12, wherein $R^5$ is $CH_3$.

Embodiment 19

The compound of embodiment 18, wherein $R^4$ is $CH_3$.

Embodiment 20

The compound of embodiment 18, wherein $R^4$ is $CH_3$ and $R^6$ is H.

Embodiment 21

The compound of embodiment 18, wherein $R^4$ is $CH_3$ and $R^6$ is $CH_3$.

Embodiment 22

The compound according to any one of embodiments 8-12, wherein $R^5$ is halogen.

Embodiment 23

The compound of embodiment 22, wherein $R^5$ is F or Cl.

Embodiment 24

The compound according to any one of embodiments 22-23, wherein $R^4$ is $CH_3$.

Embodiment 25

The compound according to any one of embodiments 22-23, wherein $R^4$ is $CH_3$ and $R^6$ is $CH_3$.

Embodiment 26

The compound according to any one of embodiments 22-23, wherein $R^4$ is halogen.

Embodiment 27

The compound of embodiment 26, wherein $R^4$ is F.

Embodiment 28

The compound of embodiment 26, wherein $R^4$ is Cl.

Embodiment 29

The compound according to any one of embodiments 22-28, wherein $R^6$ is H.

Embodiment 30

The compound according to any one of embodiments 22-28, wherein $R^6$ is $CH_3$.

Embodiment 31

The compound of embodiment 8, wherein $R^2$ is

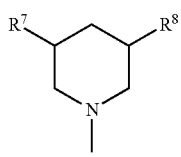

where $R^7$ and $R^8$ are independently H, $CH_3$, $OCH_3$, and halogen.

Embodiment 32

The compound of embodiment 10, wherein $R^1$ is

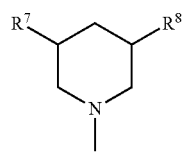

where $R^7$ and $R^8$ are independently H, $CH_3$, $OCH_3$, and halogen.

Embodiment 33

The compound according to any one of embodiments 31-32, wherein $R^7$ is $CH_3$ and $R^8$ is $CH_3$.

Embodiment 34

The compound of embodiment 8, wherein $R^2$ is

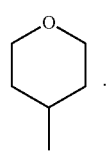

Embodiment 35

The compound of embodiment 10, wherein $R^1$ is

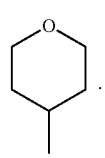

Embodiment 36

The compound of embodiment 8, wherein $R^2$ is

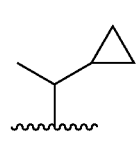

Embodiment 37

The compound of embodiment 10, wherein $R^1$ is

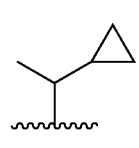 [SMILES: *C(C)C1CC1]

Embodiment 38
The compounds according to any one of embodiments 1-37, wherein R⁰ is NH.
Embodiment 39
The compound according to any one of embodiments 31-33, wherein R⁰ is absent.
Embodiment 40
The compound of embodiment 1, wherein said compound is a compound according to a formula selected from the group consisting of
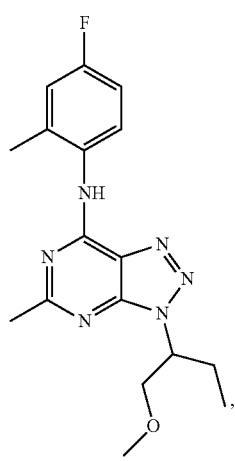
J06
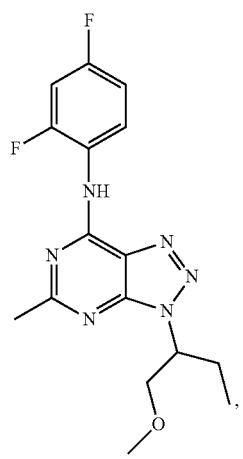
J07
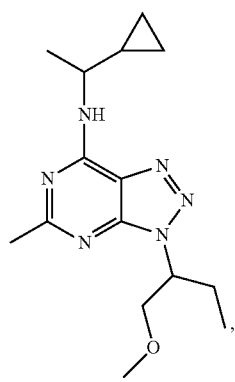
J11
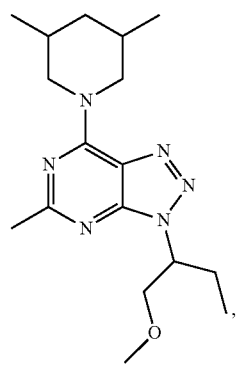
J12
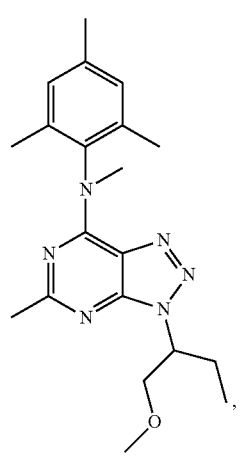
J14
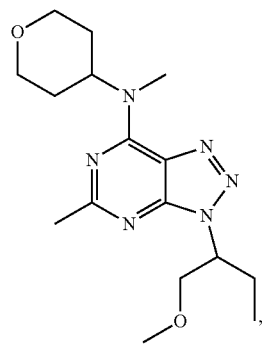
J15
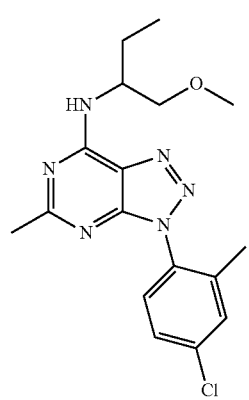
J19

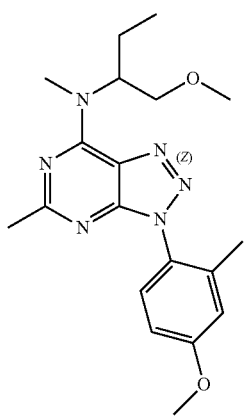
J20

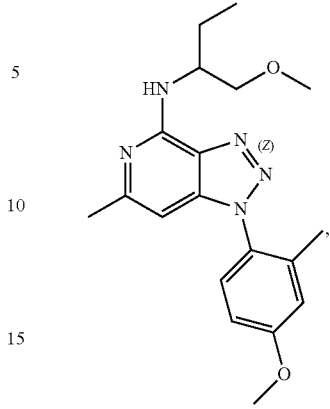
J23

J21
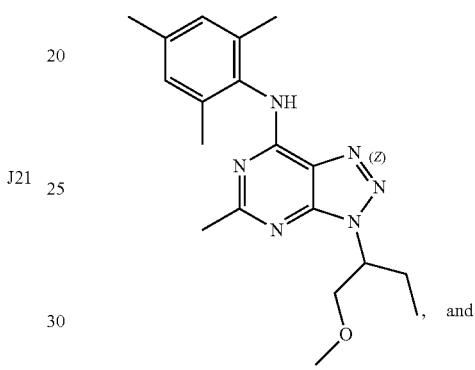
J24

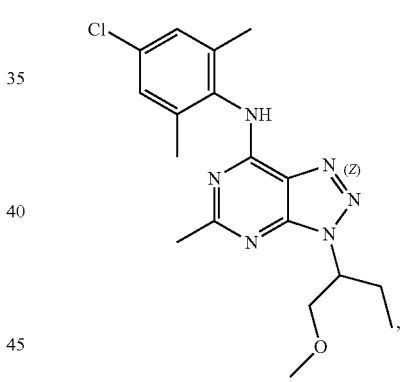
J25

J22 or a pharmaceutically acceptable salt or solvate thereof.

Embodiment 41

The compound of embodiment 1, wherein said compound is a compound according to a formula selected from the group consisting of J14, J19, J20, J21, J22, J23, J24, and J25, or a pharmaceutically acceptable salt or solvate thereof.

Embodiment 42

The composition according to any one of embodiments 1-41 wherein said composition is effective to decrease in corticotropin-releasing factor (CRF-1) induced p-tau.

Embodiment 43

The compound according to any one of embodiments 1-42, wherein said compound is a substantially pure S enantiomer.

Embodiment 44

The compound according to any one of embodiments 1-42, wherein said compound is a substantially pure R enantiomer.

Embodiment 45

A pharmaceutical formulatical formulation comprising a compound according to any one of embodiments 1-44 and a pharmaceutically acceptable carrier or excipient.

Embodiment 46

The formulation of embodiment 45, wherein said formulation is a unit dosage formulation.

Embodiment 47

The formulation according to any one of embodiments 45-46, wherein said composition is formulated for administration via a route selected from the group consisting of isophoretic delivery, transdermal delivery, aerosol administration, administration via inhalation, oral administration, intravenous administration, and rectal administration.

Embodiment 48

A method of decreasing p-tau in a mammal or inhibiting or preventing an increase in p-tau in a mammal, said method comprising:
  administering to said mammal an effective amount of one or more compounds according to any one of embodiments 1-44; and/or
  administering to said mammal an effective amount of a compound selected from the group consisting of J03, J04, J05, J08, and J17, or a pharmaceutically acceptable salt or solvate thereof; and/or
  administering to said mammal an effective amount of a formulation according to any one of embodiments 45-47; and/or
  administering to said mammal an effective amount of a formulation comprising a compound selected from the group consisting of J03, J04, J05, J08, and J17 and a pharmaceutically acceptable carrier or excipient.

Embodiment 49

A method of promoting the processing of amyloid precursor protein (APP) by the non-amyloidogenic pathway in a mammal, said method comprising:
  administering to said mammal an effective amount of one or more compounds according to any one of embodiments 1-44; and/or
  administering to said mammal an effective amount of a compound selected from the group consisting of J03, J04, J05, J08, and J17, or a pharmaceutically acceptable salt or solvate thereof; and/or
  administering to said mammal an effective amount of a formulation according to any one of embodiments 45-47; and/or
  administering to said mammal an effective amount of a formulation comprising a compound selected from the group consisting of J03, J04, J05, J08, and J17 and a pharmaceutically acceptable carrier or excipient.

Embodiment 50

The method of embodiment 49, wherein said method decreases p-tau in said mammal.

Embodiment 51

A method of preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease in a mammal, said method comprising:
  administering to said mammal an effective amount of one or more compounds according to any one of embodiments 1-44; and/or
  administering to said mammal an effective amount of a compound selected from the group consisting of J03, J04, J05, J08, and J17, or a pharmaceutically acceptable salt or solvate thereof; and/or
  administering to said mammal an effective amount of a formulation according to any one of embodiments 45-47; and/or
  administering to said mammal an effective amount of a formulation comprising a compound selected from the group consisting of J03, J04, J05, J08, and J17 and a pharmaceutically acceptable carrier or excipient.

Embodiment 52

A method of ameliorating one or more symptoms of Alzheimer's disease, and/or reversing Alzheimer's disease, and/or reducing the rate of progression of Alzheimer's disease in a mammal, said method comprising:
  administering to said mammal an effective amount of one or more compounds according to any one of embodiments 1-44; and/or
  administering to said mammal an effective amount of a compound selected from the group consisting of J03, J04, J05, J08, and J17, or a pharmaceutically acceptable salt or solvate thereof; and/or
  administering to said mammal an effective amount of a formulation according to any one of embodiments 45-47; and/or
  administering to said mammal an effective amount of a formulation comprising a compound selected from the group consisting of J03, J04, J05, J08, and J17 and a pharmaceutically acceptable carrier or excipient.

Embodiment 53

The method according to any one of embodiments 48-52, wherein said method comprises administering a compound selected from the group consisting of J03, J04, J05, J06, J07, J08, J09, J10, J11, J12, J14, J15, J17, J19, J20, J21, J22, J23, J24, and J25, or a pharmaceutically acceptable salt or solvate thereof.

Embodiment 54

The method according to any one of embodiments 48-52, wherein said method comprises administering a compound selected from the group consisting of J14, J19, J20, J21, J22, J23, J24, and J25, or a pharmaceutically acceptable salt or solvate thereof.

Embodiment 55

The method according to any one of embodiments 48-52, wherein said method comprises administering a compound selected from the group consisting of J03, J04, J05, J08, and J17, or a pharmaceutically acceptable salt or solvate thereof.

Embodiment 56

The method according to any one of embodiments 48-52, wherein said method comprises administering J03, or a pharmaceutically acceptable salt or solvate thereof.

Embodiment 57

The method according to any one of embodiments 48-56, wherein the mammal has a familial risk for having Alzheimer's disease.

Embodiment 58

The method according to any one of embodiments 48-56, wherein the mammal has a familial Alzheimer's disease (FAD) mutation.

Embodiment 59

The method according to any one of embodiments 48-56, wherein said mammal has one copy of the ApoE4 allele.

Embodiment 60

The method according to any one of embodiments 48-56, wherein said mammal has two copies of the ApoE4 allele.

Embodiment 61

The method according to any one of embodiments 48-60, wherein said mammal is a human.

Embodiment 62

The method according to any one of embodiments 48-61, wherein, wherein said method is a method of preventing or delaying the transition from a cognitively asymptomatic pre-Alzheimer's condition to a pre-Alzheimer's cognitive dysfunction.

Embodiment 63

The method according to any one of embodiments 48-61, wherein said method is a method of preventing or delaying the onset of a pre-Alzheimer's cognitive dysfunction.

Embodiment 64

The method according to any one of embodiments 48-63, wherein said method comprises ameliorating one or more symptoms of a pre-Alzheimer's cognitive dysfunction.

Embodiment 65

The method according to any one of embodiments 48-63, wherein said method comprises preventing or delaying the progression of a pre-Alzheimer's cognitive dysfunction to Alzheimer's disease.

Embodiment 66

The method of embodiment 65, wherein said method delays or prevents the progression of MCI to Alzheimer's disease.

Embodiment 67

The method according to any one of embodiments 48-65, wherein said mammal exhibits biomarker positivity of Aβ in a clinically normal human mammal age 50 or older.

Embodiment 68

The method according to any one of embodiments 48-65, wherein said mammal exhibits asymptomatic cerebral amyloidosis.

Embodiment 69

The method according to any one of embodiments 48-65, wherein said mammal exhibits cerebral amyloidosis in combination with downstream neurodegeneration.

Embodiment 70

The method according to any one of embodiments 48-65, wherein said mammal is cognitively asymptomatic.

Embodiment 71

The method according to any one of embodiments 48-65, wherein said mammal exhibits cerebral amyloidosis in combination with downstream neurodegeneration and subtle cognitive/behavioral decline.

Embodiment 72

The method of embodiment 71, wherein said downstream neurodegeneration is determined by one or more elevated markers of neuronal injury selected from the group consisting of tau, and FDG uptake.

Embodiment 73

The method according to any one of embodiments 68-72, wherein said cerebral amyloidosis is determined by PET, or CSF analysis, and structural MRI (sMRI).

Embodiment 74

The method according to any one of embodiments 48-65, wherein said mammal is a mammal diagnosed with mild cognitive impairment.

Embodiment 75

The method of embodiment 74, wherein said mammal shows a clinical dementia rating above zero and below about 1.5.

Embodiment 76

The method according to any one of embodiments 48-66, wherein the mammal is not diagnosed as at risk for a neurological disease or disorder other than Alzheimer's disease.

Embodiment 77

The method according to any one of embodiments 48-76, wherein said administration produces a reduction in the CSF of levels of one or more components selected from the group consisting of total-Tau (tTau), phospho-Tau (pTau), APPneo, soluble Aβ40, pTau/Aβ342 ratio and tTau/Aβ342 ratio, and/or an increase in the CSF of levels of one or more components selected from the group consisting of Aβ342/Aβ340 ratio, Aβ342/Aβ338 ratio, sAPPα, sAPPα/sAPPβ ratio, sAPPα/Aβ40 ratio, and sAPPα/Aβ42 ratio.

Embodiment 78

The method according to any one of embodiments 48-77, wherein said administration produces a reduction of the plaque load in the brain of the mammal.

Embodiment 79

The method according to any one of embodiments 48-78, wherein said administration produces a reduction in the rate of plaque formation in the brain of the mammal.

Embodiment 80

The method according to any one of embodiments 48-79, wherein said administration produces an improvement in the cognitive abilities of the mammal.

Embodiment 81

The method according to any one of embodiments 48-79, wherein said administration produces an improvement in, a stabilization of, or a reduction in the rate of decline of the clinical dementia rating (CDR) of the mammal.

Embodiment 82

The method according to any one of embodiments 48-81, wherein the mammal is a human and said administration produces a perceived improvement in quality of life by the human.

Embodiment 83

The method according to any one of embodiments 48-82, wherein the compound(s) are administered via a route selected from the group consisting of oral delivery, isophoretic delivery, transdermal delivery, parenteral delivery, aerosol administration, administration via inhalation, intravenous administration, and rectal administration.

Embodiment 84

The method according to any one of embodiments 48-82, wherein the compound is administered orally.

Embodiment 85

The method according to any one of embodiments 48-84, wherein the administering is over a period of at least three weeks.

Embodiment 86

The method according to any one of embodiments 48-84, wherein the administering is over a period of at least 6 months.

Embodiment 87

The method according to any one of embodiments 48-86, wherein the compound(s) are administered via a route selected from the group consisting of isophoretic delivery, transdermal delivery, aerosol administration, administration via inhalation, oral administration, intravenous administration, and rectal administration.

Definitions

Unless otherwise indicated, reference to a compound (e.g., to a triazolopyrimidine and/or triazolopyridine as described herein) should be construed broadly to include pharmaceutically acceptable salts, prodrugs, tautomers, alternate solid forms, non-covalent complexes, and combinations thereof, of a chemical entity of the depicted structure or chemical name.

Generally, reference to a certain element such as hydrogen or H is meant to include all isotopes of that element. For example, if an R group is defined to include hydrogen or H, it also includes deuterium and tritium. Accordingly, isotopically labeled compounds are within the scope of this invention.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

A prodrug is a compound that is converted to a therapeutically active compound after administration. For example, conversion may occur by hydrolysis of an ester group, such as a $C_1$-$C_6$ alkyl ester of the carboxylic acid group of the present compounds, or some other biologically labile group. Prodrug preparation is well known in the art. For example, "Prodrugs and Drug Delivery Systems," which is a chapter in Richard B. Silverman, *Organic Chemistry of Drug Design and DrugAction,* 2d Ed., Elsevier Academic Press: Amsterdam, 2004, pp. 496-557, provides further detail on the subject.

Tautomers are isomers that are in equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like. In various embodiments alternate solid forms of any of the compounds described herein are contemplated.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), and the like.

The term "alkyl" refers to and covers any and all groups that are known as normal alkyl, branched-chain alkyl, cycloalkyl and also cycloalkyl-alkyl. Illustrative alkyl groups include, but are not limited to methyl, ethyl, n-propyl, isopropyl, n-butyl, isobutyl, sec-butyl, t-butyl, octyl, and decyl. The term "cycloalkyl" refers to cyclic, including polycyclic, saturated hydrocarbyl groups. Examples include, but are not limited to cyclopentyl, cyclohexyl, dicyclopentyl, norbornyl, octahydronapthyl, and spiro[3.4]octyl. In certain embodiments, alkyl groups contain 1-12 carbon atoms (C1-12 alkyl), or 1-9 carbon atoms ($C_{1-9}$ alkyl), or 1-6 carbon atoms ($C_{1-6}$ alkyl), or 1-5 carbon atoms ($C_{1-5}$ alkyl), or carbon atoms ($C_{1-4}$ alkyl), or 1-3 carbon atoms ($C_{1-3}$ alkyl), or 1-2 carbon atoms ($C_{1-2}$ alkyl).

By way of example, the term "$C_{1-6}$ alkyl group" refers to a straight chain or branched chain alkyl group having 1 to 6 carbon atoms, and may be exemplified by a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, and an n-hexyl group.

The term "alkoxy" as used herein means an alkyl group bound through a single, terminal oxygen atom. An "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein means an alkyl group bound through a single, terminal sulfur atom. An "alkylthio" group may be represented as —S-alkyl where alkyl is as defined above. The term "arylthio" is used similarly, and may be represented as —S-aryl, with aryl as defined below. The term "mercapto" refers to —SH.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

The term "heteroaryl group" refers to a monocyclic or condensed-ring aromatic heterocyclic group containing one or more hetero-atoms selected from O, S and N. If the aromatic heterocyclic group has a condensed ring, it can include a partially hydrogenated monocyclic group. Examples of such a heteroaryl group include a pyrazolyl group, a thiazolyl group, an isothiazolyl group, a thiadiazolyl group, an imidazolyl group, a furyl group, a thienyl group, an oxazolyl group, an isoxazolyl group, a pyrrolyl group, an imidazolyl group, a (1,2,3)- and (1,2,4)-triazolyl group, a tetrazolyl group, a pyranyl group, a pyridyl group, a pyrimidinyl group, a pyrazinyl group, a pyridazinyl group, a quinolyl group, an isoquinolyl group, a benzofuranyl group, an isobenzofuranyl group, an indolyl group, an isoindolyl group, an indazolyl group, a benzoimidazolyl group, a benzotriazolyl group, a benzoxazolyl group, a benzothiazolyl group, a benzo[b]thiophenyl group, a thieno[2,3-b]thiophenyl group, a (1,2)- and (1,3)-benzoxathiol group, a chromenyl group, a 2-oxochromenyl group, a benzothiadiazolyl group, a quinolizinyl group, a phthalazinyl group, a naphthyridinyl group, a quinoxalinyl group, a quinazolinyl group, a cinnolinyl group, and a carbazolyl group.

A "derivative" of a compound means a chemically modified compound wherein the chemical modification takes place at one or more functional groups of the compound. The derivative however, is expected to retain, or enhance, the pharmacological activity of the compound from which it is derived.

As used herein, "administering" refers to local and systemic administration, e.g., including enteral, parenteral, pulmonary, and topical/transdermal administration. Routes of administration for agents (e.g., triazolopyrimidines and/or triazolopyridines described herein, or a tautomer(s) or stereoisomer(s) thereof, or pharmaceutically acceptable salts or solvates of said compound(s), said stereoisomer(s), or said tautomer(s), or analogues, derivatives, or prodrugs thereof) that find use in the methods described herein include, e.g., oral (per os (p.o.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering the agent(s) described herein or composition to a mammal so that the agent(s) or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration" or "administering in conjunction with" when used, for example with respect to the active agent(s) described herein e.g., triazolopyrimidine(s) and/or triazolopyridine(s) described herein, or a tautomer(s) or stereoisomer(s) thereof, or pharmaceutically acceptable salts or solvates of said compound(s), said stereoisomer(s), or said tautomer(s), or analogues, derivatives, or prodrugs thereof and a second active agent (e.g., a cognition enhancer), refers to administration of the agent(s) and/the second active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The term "effective amount" or "pharmaceutically effective amount" refer to the amount and/or dosage, and/or dosage regime of one or more agent(s) necessary to bring about the desired result e.g., an amount sufficient to mitigating in a mammal one or more symptoms associated with mild cognitive impairment (MCI), or an amount sufficient to lessen the severity or delay the progression of a disease characterized by amyloid deposits in the brain in a mammal (e.g., therapeutically effective amounts), an amount sufficient to reduce the risk or delaying the onset, and/or reduce the ultimate severity of a disease characterized by amyloid deposits in the brain in a mammal (e.g., prophylactically effective amounts).

The phrase "cause to be administered" refers to the actions taken by a medical professional (e.g., a physician), or a person controlling medical care of a subject, that control and/or permit the administration of the agent(s) at issue to the subject. Causing to be administered can involve diagnosis and/or determination of an appropriate therapeutic or prophylactic regimen, and/or prescribing particular agent(s) for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination, or prevention of an increase (e.g., a stress-induced increase), of one or more markers that are characteristic of the pathology or disease (e.g., of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPβ ratio, sAPPα/Aβ40 ratio, sAPPα/Aβ42 ratio, etc.) and/or reduction, stabilization or reversal of one or more diagnostic criteria (e.g., clinical dementia rating (CDR)).

As used herein, the phrase "consisting essentially of" refers to the genera or species of active pharmaceutical agents recited in a method or composition, and further can include other agents that, on their own do not substantial activity for the recited indication or purpose. In some embodiments, the phrase "consisting essentially of" expressly excludes the inclusion of one or more additional agents that have neuropharmacological activity other than the recited agent(s) (e.g., other than ASBIs such as galangin, rutin, and analogues, derivatives, or prodrugs thereof). In some embodiments, the phrase "consisting essentially of" expressly excludes the inclusion of one or more additional active agents other than the active agent(s) described herein (e.g., other than ASBIs such as galangin, rutin, and analogues, derivatives, or prodrugs thereof). In some embodiments, the phrase "consisting essentially of" expressly excludes the inclusion of one or more acetylcholinesterase inhibitors.

The terms "subject", "individual", and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

The term "formulation" or "drug formulation" or "dosage form" or "pharmaceutical formulation" as used herein refers to a composition containing at least one therapeutic agent or medication for delivery to a subject. In certain embodiments the dosage form comprises a given "formulation" or "drug formulation" and may be administered to a patient in the form of a lozenge, pill, tablet, capsule, suppository, membrane, strip, liquid, patch, film, gel, spray or other form.

The term "mucosal membrane" refers generally to any of the mucus-coated biological membranes in the body. In certain embodiments active agent(s) described herein can be administered herein via any mucous membrane found in the body, including, but not limited to buccal, perlingual, nasal, sublingual, pulmonary, rectal, and vaginal mucosa. Absorption through the mucosal membranes of the oral cavity and those of the gut are of interest. Thus, peroral, buccal, sublingual, gingival and palatal absorption are contemplated herein.

The term "transmucosal" delivery of a drug and the like is meant to encompass all forms of delivery across or through a mucosal membrane.

The term "bioadhesion" as used herein refers to the process of adhesion of the dosage form(s) to a biological surface, e.g., mucosal membranes.

"Controlled drug delivery" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

"Sustained drug delivery" refers to release or administration of a drug from a source (e.g., a drug formulation) in a sustained fashion over a protracted yet specific period of time, that may extend from several minutes to a few hours, days, weeks or months. In various embodiments the term "sustained" will be used to refer to delivery of consistent and/oe substantially constant levels of drug over a time period ranging from a few minutes to a day, with a profile characterized by the absence of an immediate release phase, such as the one obtained from IV administration.

The term "$T_{max}$" as used herein means the time point of maximum observed plasma concentration.

The term "$C_{max}$" as used herein means the maximum observed plasma concentration.

The term "plasma $t_{1/2}$" as used herein means the observed "plasma half-life" and represents the time required for the drug plasma concentration to reach the 50% of its maximal value ($C_{max}$). This facilitates determination of the mean duration of pharmacological effects. In addition, it facilitates direct and meaningful comparisons of the duration of different test articles after delivery via the same or different routes.

The term "Optimal Therapeutic Targeting Ratio" or "OTTR" represents the average time that the drug is present at therapeutic levels, defined as time within which the drug plasma concentration is maintained above 50% of $C_{max}$ normalized by the drug's elimination half-life multiplied by the ratio of the $C_{max}$ obtained in the dosage form of interest over the $C_{max}$ following IV administration of equivalent doses and it is calculated by the formula:

$$OTTR = (C^{IV}_{max}/C_{max}) \times (Dose/Dose^{IV})(\text{Time above 50% of } C_{max})/(\text{Terminal}^{IV} \text{ elimination half-life of the drug}).$$

The term "substantial pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical or chemical properties, of the compound. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

The term "substantially pure" when used with respect to enantiomers indicates that one particular enantiomer (e.g. an S enantiomer or an R enantiomer) is substantially free of its stereoisomer. In various embodiments substantially pure indicates that a particular enantiomer is at least 70%, or at least 80%, or at least 90%, or at least 95%, or at least 98%, or at least 99% of the purified compound. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) J. Chromatogr., 113(3): 283-302). Racemic mixtures of chiral compounds of the can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

DETAILED DESCRIPTION

Novel compounds that inhibit corticotropin-releasing factor CRF-1 associated phosphorylation of tau are identified herein. Without being bound to a particular theory, it is believed these compounds show efficacy in the treatment of ongoing Alzheimer's Disease, in the delay or prevention of the onset of Alzheimer's disease, in the onset of mild cognitive impairment (MCI) when mediated by an amyloidogenic process, in the delay of a transition from MCI to AD, and in the delay or prevention of MCI.

In people diagnosed with Alzheimer's disease (AD), and in our hands using the J20 mouse model of AD, the level of tau phosphorylation provides the closest correlation to degree of cognitive impairment. The reversal of tau pathology alone can improve memory, even in the presence of high Aβ42 in J20 mice Stress and the associated increase in corticotropin-releasing factor CRF-1 is known to increase the phosphorylation of tau.

To identify therapeutic candidates, a clinical library of CRF-1R inhibitors to was screened to determine their effects on cortisol-induced p-tau increases. One compound, designated "J03" (N-(4-Methoxy-2-methylphenyl)-1-[1-(methoxymethyl)propyl]-6-methyl-1H-1,2,3-triazolo[4,5-c] pyridine-4-amine, see FIG. 4) acted as a CRF-1 antagonist (Ki~7.9 nM) and showed no binding to CRFR2 (Ki>10,000 nM). J03 was shown specifically to inhibit stress-induced p-tau increases by cortisol in vitro. Notably, testing of another set of CRF1 antagonists did not induce a similar inhibition of p-tau.

Following the observations of J03 a number of analogs were developed. One design focus was to replace the triazolopyridine ring of J03 with a triazolopyrimidine ring (see, e.g., FIG. 1) and to explore the orientation of and vary the substituents around the triazolopyridine and triazolopyrimidine rings. It is noted that with respect to any triazolopyridine and triazolopyrimidine described herein a compound with substituents A and B in reversed positions (see, e.g., FIG. 1) is also contemplated. Synthetic schemes have been developed and the analog synthesis has been performed. Biological activity and pharmacokinetics has been evaluated (see, Example 2).

Figure 2:
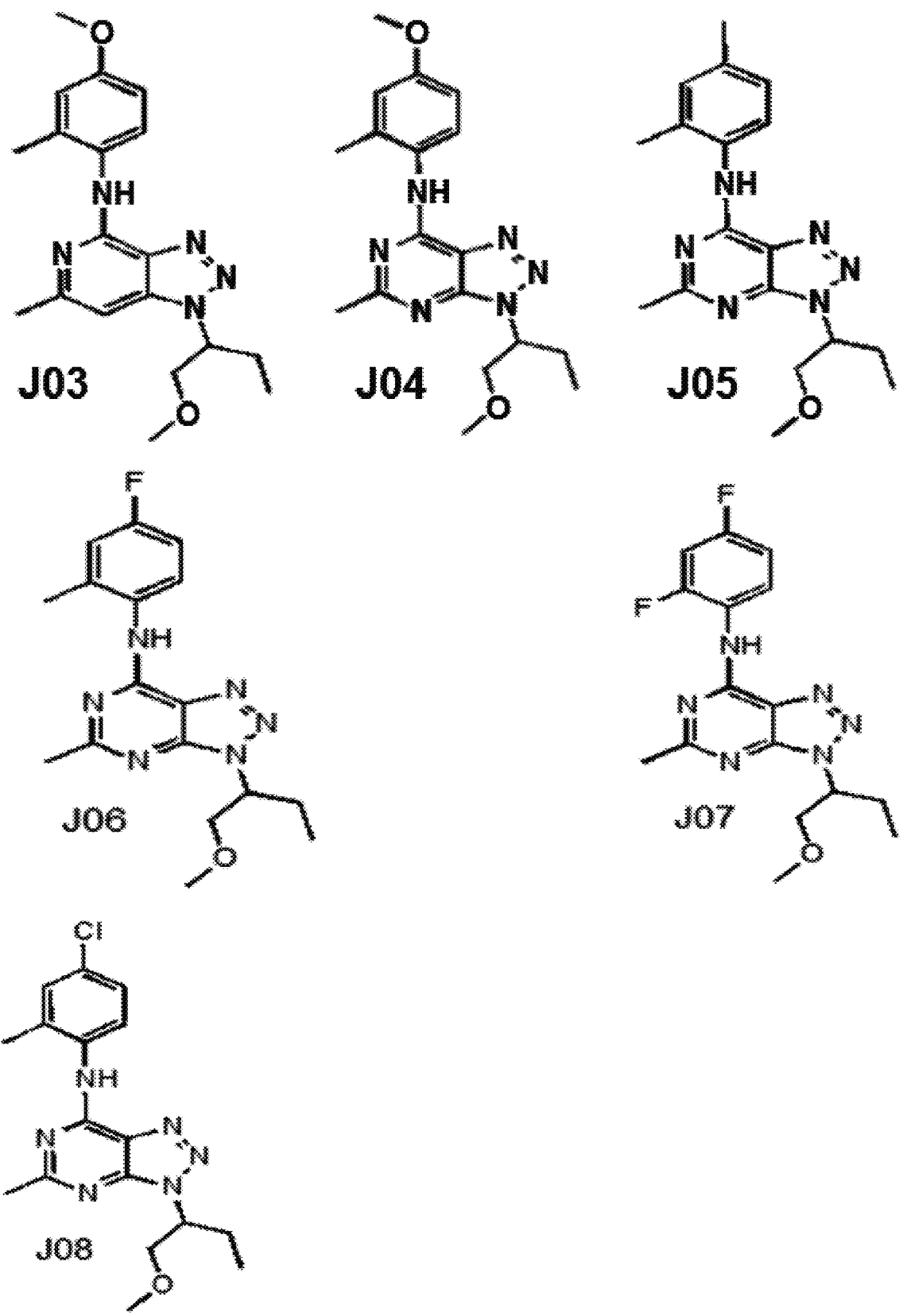
FIG. 2 illustrates a number of triazolopyridines and triazolopyrimidines that lower stress-induced p-tau.

A number of compounds are illustrated in FIG. 2 and some properties of these compounds are summarized below in Table 1.

TABLE 1

Illustrative "J-series" (triazolopyridine and triazolopyrimidine) compounds.
Compound with effects highlighted (in green) were better than those for J03. J17 and J19 show the most efficacy.

| | Primary (SH-SY5Y) | | Secondary (SH-Sy5Y, CRF stimulation) | | | | Tertiary | |
|---|---|---|---|---|---|---|---|---|
| | Tau | p-Tau | Tau | p-Tau | sAPPα | CRF | | |
| Cmpd | % | (%) | % | (%) | (%) | 1 Ki | PAMPA | Solubility |
| J03 | Unchanged | ↓ ≈10% | ↓ >20% | ↓ >20% | Unchanged | 7 nM | 0.92 | ≈10 mM DMSO |
| J04 | Unchanged | ↓ >10% | ↓ >20% | ↓ >20% | ↓ ≈10% | 15 nM | 0.44 | ≈10 mM DMSO |
| J05 | ↓ ≈10% | ↓ >10% | ↓ >10% | ↓ ≈10% | In progress | 100 nM | 0.99 | ≈10 mM DMSO |
| J06 | Unchanged | ↓ ≈10% | ↑ ≈10% | Unchanged | In progress | >1 μM | NA | ≈10 mM DMSO |
| J07 | ↓ ≈10% | ↓ >10% | ↓ >30% | ↓ >20% | ↓ ≈10% | >1 μM | 0.72 | ≈10 mM DMSO |
| J08 | Unchanged | ↓ >10% | ↓ >20% | ↓ >20% | Unchanged | 15 nM | 1.27 | ≈10 mM DMSO |
| J09 | Unchanged | ↑ >15% | NA | NA | NA | >10 OnM | NA | ≈10 mM DMSO |
| J10 | Unchanged | Unchanged | NA | NA | NA | >10 OnM | NA | ≈10 mM DMSO |
| J11 | Unchanged | ↓ >10% | ↓ >20% | ↓ >20% | Unchanged | >1 μM | 0.94 | ≈10 mM DMSO |
| J12 | ↓ >10% | ↓ >10% | ↓ >30% | ↓ >20% | Unchanged | >1 μM | 2.39 | ≈10 mM DMSO |
| J14 | Unchanged | ↓ ≈10% | ↓ >20% | ↓ >20% | In progress | 25 nM | 1.11 | ≈10 mM DMSO |
| J15 | Unchanged | ↓ >10% | ↓ >30% | ↓ >30% | >10% | >1 μM | 0.34 | ≈10 mM DMSO |

TABLE 1-continued

Illustrative "J-series" (triazolopyridine and triazolopyrimidine) compounds.
Compound with effects highlighted (in green) were better than those for J03. J17 and J19 show the most efficacy.

| | Primary (SH-SY5Y) | | Secondary (SH-Sy5Y, CRF stimulation) | | | | Tertiary | |
|---|---|---|---|---|---|---|---|---|
| | Tau | p-Tau | Tau | p-Tau | sAPPα | CRF | | |
| Cmpd | % | (%) | % | (%) | (%) | 1 Ki | PAMPA | Solubility |
| J17 | ↓ >10% | ↓ >10% | ↓ >30% | ↓ >30% | Unchanged | 30 nM | 0.64 | ≈10 mM DMSO |
| J17 HCl | Unchanged | Unchanged | NA | NA | NA | NA | NA | ≈10 mM DMSO |
| J19 | ↓ >10% | ↓ >10% | ↓ >20% | ↓ >30% | Unchanged | 100 nM | 0.75 | ≈10 mM DMSO |
| J20 HCl | Unchanged | ↑ >15% | NA | NA | NA | NA | NA | ≈10 mM DMSO |

As illustrated, a number of these compounds are effective in lowering p-tau and/or reducing or preventing a stress-induced increase in p-tau. Moreover, as indicated above, reduction in p-tau (or inhibition of p-tau increase) is an important metric of efficacy in pathologies characterized by the accumulation of amyloid plaque (e.g., Alzheimer's disease, MCI, etc.). It is believed these compounds and analogs thereof, pharmaceutically acceptable salts and clathrates thereof, and the like are useful in the prophylaxis and/or treatment of pathologies characterized by the accumulation of amyloid plaque.

Accordingly it is believed that these agents) (e.g., triazolopyrimidine and/or triazolopyridine compounds described herein, or a tautomer(s) or stereoisomer(s) thereof, or pharmaceutically acceptable salts or solvates of said compounds(s), said stereoisomer(s), or said tautomer(s), or analogues, derivatives, or prodrugs thereof) can be used to decrease p-tau in a mammal, and/or to inhibit or prevent an increase in p-tau, and/or to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by the non-amyloidogenic pathway. In certain embodiments these agents can be used in the treatment of Alzheimer's disease (e.g., to lessen the severity of the disease, and/or to ameliorate one or more symptoms of the disease, and/or to slow the progression of the disease).

While the methods described herein are detailed primarily in the context of mild cognitive impairment (MCI) and Alzheimer's disease (AD) it is believed they can apply equally to other pathologies characterized by amyloidosis. In this respect, an illustrative, but non-limiting list of conditions characterized by amyloid plaque formation is shown in Table 2.

TABLE 2

Illustrative pathologies characterized by amyloid formation/deposition.

| Disease | Characteristic Protein | Abbreviation |
|---|---|---|
| Alzheimer's disease | Beta amyloid | Aβ |
| Diabetes mellitus type 2 | Islet amyloid protein (Amylin) | IAPP |
| Parkinson's disease | Alpha-synuclein | SNCA |
| Transmissible spongiform encephalopathy e.g. Bovine spongiform encephalopathy | Prion | PrP |
| Huntington's Disease | Huntingtin | HTT |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |
| Prolactinomas | Prolactin | APro |
| Familial amyloid polyneuropathy | Transthyretin | ATTR |
| Hereditary non-neuropathic systemic amyloidosis | Lysozyme | ALys |
| Dialysis related amyloidosis | Beta 2 microglobulin | Aβ2M |
| Finnish amyloidosis | Gelsolin | AGel |
| Lattice corneal dystrophy | Keratoepithelin | AKer |
| Cerebral amyloid angiopathy | Beta amyloid | Aβ |
| Cerebral amyloid angiopathy (Icelandic type) | Cystatin | ACys |
| Systemic AL amyloidosis | Immunoglobulin light chain AL | AL |
| Sporadic Inclusion Body Myositis | S-IBM | none |
| Age-related macular degeneration (AMD) | Beta amyloid | Aβ |
| Cerebrovascular dementia | Cerebrovascular amyloid | CVA |

Therapeutic and Prophylactic Methods.

In various embodiments therapeutic and/or prophylactic methods are provided that utilize the active agent(s) (e.g., triazolopyrimidine(s) and/or triazolopyridines described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) are provided. Typically the methods involve administering one or more active agent(s) to a subject (e.g., to a human in need thereof) in an amount sufficient to realize the desired therapeutic or prophylactic result.

Prophylaxis

In certain embodiments active agent(s) (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) are utilized in various prophylactic contexts. Thus, for example, in certain embodiments, the active agent(s) can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process(es) (abbreviated as AD-P, see, e.g., Sperling et al. (2011) *Alzheimer's & Dementia*, 1-13) at risk for progression to AD dementia to biomarker-positive individuals who are already demonstrating very subtle decline but not yet meeting standardized criteria for MCI (see, e.g., Albert et al. (2011) *Alzheimer's and Dementia*, 1-10 (doi:10.1016/j.jalz.2011.03.008).

This latter group of individuals might be classified as "not normal, not MCI" but would be can be designated "presymptomatic" or "pre-clinical or "asymptomatic" or "premanifest"). In various embodiments this continuum of presymptomatic AD can also encompass, but is not necessarily limited to, (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al. (2010) *Lancet Neurol.*, 9: 119-128.). This biomarker model parallels proposed pathophysiological sequence of (pre-AD/AD), and is relevant to tracking the preclinical (asymptomatic) stages of AD (see, e.g., FIG. 3 in Sperling et al. (2011) *Alzheimer's & Dementia*, 1-13). Biomarkers of brain amyloidosis include, but are not limited to reductions in CSF $A\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al. (2009) *Neurology*, 73: 294-301; Yaffe et al. (2011) *JAMA* 305: 261-266).

In certain embodiments the subjects suitable for the prophylactic methods contemplated herein include, but are not limited to, subjects characterized as having asymptomatic cerebral amyloidosis. In various embodiments these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomatology.

It is noted that currently available CSF and PET imaging biomarkers of Aβ primarily provide evidence of amyloid accumulation and deposition of fibrillar forms of amyloid. Data suggest that soluble or oligomeric forms of Aβ are likely in equilibrium with plaques, which may serve as reservoirs. In certain embodiments it is contemplated that there is an identifiable preplaque stage in which only soluble forms of Aβ are present. In certain embodiments it is contemplated that oligomeric forms of amyloid may be critical in the pathological cascade, and provide useful markers. In addition, early synaptic changes may be present before evidence of amyloid accumulation.

In certain embodiments the subjects suitable for the prophylactic methods contemplated herein include, but are not limited to, subjects characterized as amyloid positive with evidence of synaptic dysfunction and/or early neurodegeneration. In various embodiments these subjects have evidence of amyloid positivity and presence of one or more markers of "downstream" AD-related neuronal injury. Illustrative, but non-limiting markers of neuronal injury include, but are not limited to (1) elevated CSF tau or phospho-tau, (2) hypometabolism in an AD-like pattern (i.e., posterior cingulate, precuneus, and/or temporoparietal cortices) on FDG-PET, and (3) cortical thinning/gray matter loss in a specific anatomic distribution (i.e., lateral and medial parietal, posterior cingulate, and lateral temporal cortices) and/ or hippocampal atrophy on volumetric MRI. Other markers include, but are not limited to fMRI measures of default network connectivity. In certain embodiments early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (i.e., in later stages of preclinical (asymptomatic) AD).

In certain embodiments the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see Hardy (1997) *Trends. Neurosci.,* 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., at about 20, about 30, about 40, about 50 years of age). Usually, however, it is not necessary to begin treatment until a patient reaches at least about 40, or at least about 50, or at least about 55, or at least about 60, or at least about 65, or at least about 70 years of age.

In some embodiments, the subject exhibits symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al. (2010) *Int. J. Alzheimer's Dis.* 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI. In such instances, the methods can delay or prevent the onset of MCI, and or reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) *Arch. Neurol.* 61(1): 59-66; and on the internet at en.wikipedia.org/wiki/Mild_cognitiveimpairment—cite_note-Grundman-1). When individuals have impairments in domains other than memory it is often classified as non-amnestic single- or multiple-domain MCI and these individuals are believed to be more likely to convert to other dementias (e.g., dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) *Arch. Neurol.* 63(5): 665-72).

The diagnosis of MCI typically involves a comprehensive clinical assessment including clinical observation, neuroimaging, blood tests and neuropsychological testing. In certain embodiments diagnostic criteria for MIC include, but are not limited to those described by Albert et al. (2011) *Alzheimer's & Dementia.* 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments clinical evaluation/diagnosis of MCI involves: (1) Concern reflecting a change in cognition reported by patient or informant or clinician (i.e., historical or observed evidence of decline over time); (2) Objective evidence of Impairment in one or more cognitive domains, typically including memory (i.e., formal or bedside testing to establish level of cognitive function in multiple domains); (3) Preservation of independence in functional abilities; (4) Not demented; and in certain embodiments, (5) An etiology of MCI consistent with AD pathophysiological processes. Typically vascular, traumatic, and medical causes of cognitive decline, are ruled out where possible. In certain embodiments, when feasible, evidence of longitudinal decline in cognition is identified. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (i.e., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (i.e., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (i.e., mutation in APP, PS1, PS2), then the development of MCI is most likely the precursor to AD dementia. The large majority of these cases develop early onset AD (i.e., onset below 65 years of age).

In addition, there are genetic influences on the development of late onset AD dementia. For example, the presence of one or two E4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE E4 positive, is more likely to progress to AD dementia within a few years than an individual without this genetic characteristic. It is believed that additional genes play an important, but smaller role than APOE and also confer changes in risk for progression to AD dementia (see, e.g., Bertram et al. (2010) *Neuron,* 21: 270-281).

In certain embodiments subjects suitable for the prophylactic methods described herein include, but need not be limited to, subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "AP" (which includes CSF $A\beta_{42}$ and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both $A\beta$, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Aβ accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein.

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be is well suited for the methods described herein.

Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al. (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al. (2008) *Brain* 131(Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating can be obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 3.

TABLE 3

Illustrative clinical dementia rating (CDR) table.

| CDR: | Impairment: | | | | |
| --- | --- | --- | --- | --- | --- |
| | None 0 | Questionable 0.5 | Mild 1 | Moderate 2 | Severe 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |

TABLE 3-continued

Illustrative clinical dementia rating (CDR) table.

| | Impairment: | | | | |
|---|---|---|---|---|---|
| CDR: | None 0 | Questionable 0.5 | Mild 1 | Moderate 2 | Severe 3 |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home. Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments administration of one or more agents described herein (e.g., triazolopyrimidine(s) and/or triazolopyridine(s) described herein, or tautomer(s) or stereoisomer(s) thereof, or pharmaceutically acceptable salts, solvates, or clathrates of said triazolopyrimidine(s) and/or triazolopyridine(s), said stereoisomer(s), or said tautomer(s), or analogues, derivatives, or prodrugs thereof) is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al. (2004) Arch. Neurol. 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemorycognitive measures included in the battery. Tests of learning, attention, perceptual speed, category fluency, and executive function may be impaired in patients with MCI, but these are far less prominent than the memory deficit.

Alzheimer's Disease (AD).

In certain embodiments the active agent(s(e.g., triazolopyrimidine(s) and/or triazolopyridine(s) described herein, or a tautomer(s) or stereoisomer(s) thereof, or pharmaceutically acceptable salts, solvates, or clathrates of said triazolopyrimidine and/or triazolopyridine(s), said stereoisomer(s), or said tautomer(s), or analogues, derivatives, or prodrugs thereof) are contemplated for the treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J. Psychiatr.,* 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 4.

TABLE 4

Illustrative stages of Alzheimer's disease.

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline
(Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline (Moderately
severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).
Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.
Tend to wander and become lost.
Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up. Reflexes become abnormal and muscles grow rigid.
Swallowing is impaired.

In various embodiments administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

Active Agent(s).

The methods described herein are based, in part, on the discovery that administration of one or more active agents (e.g., triazolopyrimidine(s) and/or triazolopyridine(s) described herein, or a tautomer(s) or stereoisomer(s) thereof, or pharmaceutically acceptable salts, solvates, or clathrates of said triazolopyrimidine(s) and/or triazolopyridine(s), said stereoisomer(s), or said tautomer(s), or analogues, derivatives, or prodrugs thereof) are effective to lower tau and/or p-tau, or to prevent the stress-induced (e.g., cortisol-induced) increase in p-tau and find use in the treatment and/or prophylaxis of diseases characterized by amyloid deposits in the brain, for example, mild cognitive impairment, Alzheimer's disease, macular degeneration, and the like.

In certain embodiments the active agent is a compound (e.g., a triazolopyrimidine and/or a triazolopyridine) as described below. In certain embodiments the activate agent comprises a compound according to the Formula I:

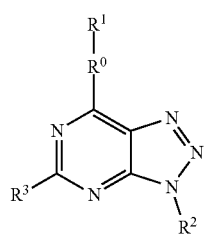

I or a pharmaceutically acceptable salt, solvate, or clathrate thereof, where $R^0$ is present or absent, and when present is selected from the group consisting of CHR, NH, O, and NCHR where R is H, alkyl (e.g., C1-C6 carbon chain), or aryl (e.g., phenyl, substituted phenyl, or heteroaryl); $R^2$ is

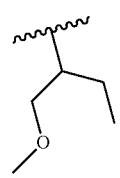

and $R^1$ is

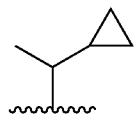

or is selected from the group consisting of a substituted or unsubstituted cyclic or heterocycle selected from the group consisting of pyridine, pyrimidine, naphthalene, quinolone, isoquinoline, cinnoline, phenyl, substituted phenyl, oxazole, furan, pyran, isoxazole, thiazole, thiophene, pyrole, pyrrolidine, pyrazole, and imidazole; or $R^1$ is

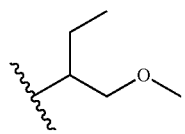

and $R^2$ is

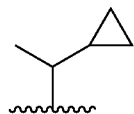 [SMILES: *C(C)C1CC1]

or is selected from the group consisting of a substituted or unsubstituted cyclic or heterocycle selected from the group consisting of pyridine, pyrimidine, naphthalene, quinolone, isoquinoline, cinnoline, phenyl, substituted phenyl, oxazole, furan, pyran, isoxazole, thiazole, thiophene, pyrole, pyrrolidine, pyrazole, and imidazole; $R^3$ is selected from the group consisting of H, $CH_3$, ethyl, propyl, butyl, $CF_3$, $NH_2$, halogen, and $CH_2O$ where R is H, alkyl (e.g., C1-C6 carbon chain), or aryl (e.g., phenyl, substituted phenyl, or heteroaryl). In certain embodiments, the compound is not J03, J04, J05, J06, J07, J08, J09, J10, JH11, J12, J15, and J17. In certain embodiments, the compound is not J03, J04, J05, J08, and J17.

In certain embodiments, in the compounds above, $R^1$ is

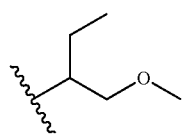 [SMILES: *C(CC)COC]

and the compound is a compound according to Formula II:

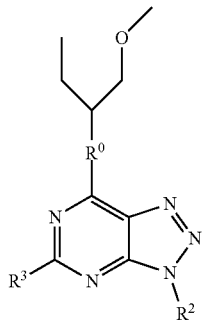

In certain embodiments, in the compounds above, $R^2$ is

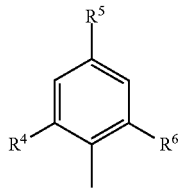

where $R^4$, $R^5$, and $R^6$ are independently selected from the group consisting of H, OH, halogen, methyl, and $OCH_3$, $CF_3$, ethyl, aryl, SR, $SO_2R$, NHCOR, and $CO_2R$, where R is H, alkyl, or aryl (e.g., where said alkyl is a C1-C6 carbon chain, and said aryl is phenyl, substituted phenyl, or heteroaryl). In certain embodiments, in compounds of Formula I, $R^2$ is

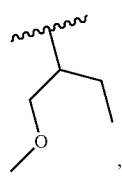 [SMILES: *C(CC)COC]

and the compound is a compound according to Formula III:

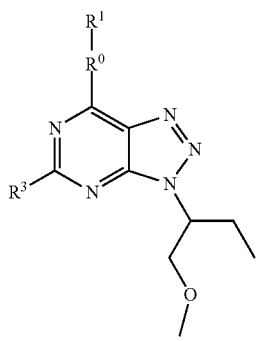

and in certain of these compounds, $R^1$ is

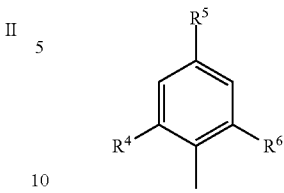

where $R^4$, $R^5$, and $R^6$ are independently selected from the group consisting of H, OH, halogen, methyl, and $OCH_3$. In certain embodiments, of any of the foregoing compounds, $R^5$ is $OCH_3$, and, in certain of these embodiments, $R^4$ is $CH_3$, $R^4$ is $CH_3$ and $R^6$ is H, $R^4$ is $OCH_3$, or $R^4$ is $OCH_3$ and $R^6$ is H. In certain embodiments, of any of the foregoing compounds, $R^5$ is halogen, or $R^5$ is F or Cl. In certain of these embodiments, particularly where $R^5$ is halogen, $R^4$ is $CH_3$, and/or $R^4$ is $CH_3$ and $R^6$ is $CH_3$, or $R^4$ is halogen (e.g., F or Cl). In certain embodiments, $R^6$ is H, or $R^6$ is $CH_3$.

In certain embodiments, the compound is a compound according to Formula II, $R^1$ is the formula shown below or the compound is a compound according to Formula III and $R^2$ is the formula shown below:

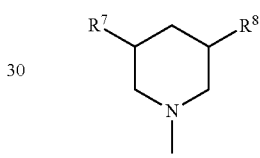

where $R^7$ and $R^8$ are independently H, $CH_3$, $OCH_3$, and halogen. In certain embodiments, $R^7$ is $CH_3$ and $R^8$ is $CH_3$.

In certain embodiments, the compound is a compound according to Formula II where $R^2$ is

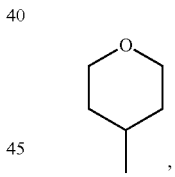

or a compound according to Formula III where $R^1$ is

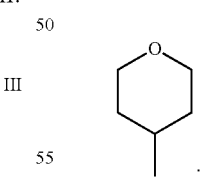

In certain embodiments, the compound is a compound according to Formula II where $R^2$ is

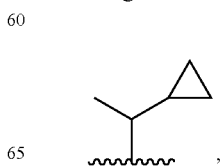

or a compound according to Formula III where R¹ is

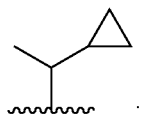 [SMILES: *C(C)C1CC1]

(5)

In certain embodiments in any of the preceding compounds, R⁰ is NH or R⁰ is absent.

In certain embodiments, the compound is a compound described in Table 5, or shown in FIG. 2.

TABLE 5

Illustrative, but non-limiting, list of triazolopyrimidine and/or a triazolopyridine compounds.

| Compound | Structure | Also contemplated |
| --- | --- | --- |
| J03 | J03 | |
| J04 | J04 | |

TABLE 5-continued

Illustrative, but non-limiting, list of triazolopyrimidine and/or a triazolopyridine compounds.

| Compound | Structure | Also contemplated | |
|---|---|---|---|
| J05 | 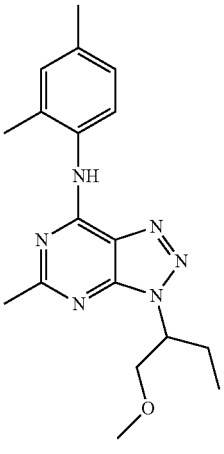 J05 | Triazolopyridine form | Substituents A and B reversed on triazolopyridine or triazolopyrimidine |
| J06 | 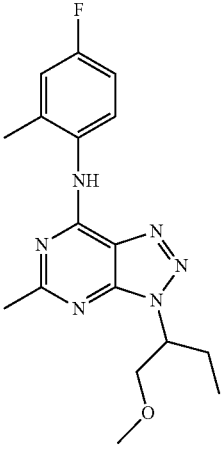 J06 | Triazolopyridine form | Substituents A and B reversed on triazolopyridine or triazolopyrimidine |
| J07 | 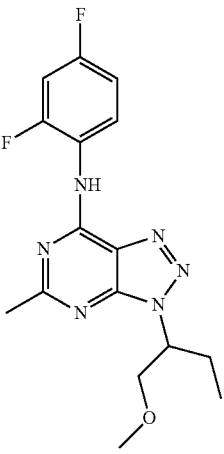 J07 | Triazolopyridine form | Substituents A and B reversed on triazolopyridine or triazolopyrimidine |

TABLE 5-continued

Illustrative, but non-limiting, list of triazolopyrimidine and/or a triazolopyridine compounds.

| Compound | Structure | Also contemplated | |
|---|---|---|---|
| J08 | 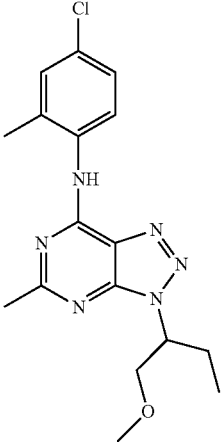 | Triazolopyridine form | Substituents A and B reversed on triazolopyridine or triazolopyrimidine |
| J09 | 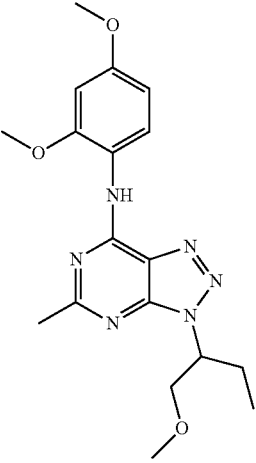 | Triazolopyridine form | Substituents A and B reversed on triazolopyridine or triazolopyrimidine |
| J10 | 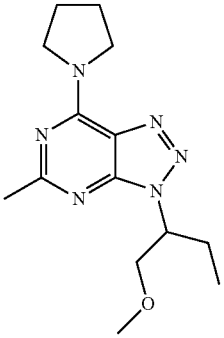 | Triazolopyridine form | Substituents A and B reversed on triazolopyridine or triazolopyrimidine |

TABLE 5-continued

Illustrative, but non-limiting, list of triazolopyrimidine and/or a triazolopyridine compounds.

| Compound | Structure | Also contemplated | |
|---|---|---|---|
| J11 | 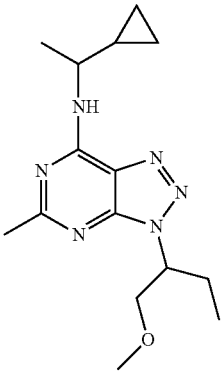 J11 | Triazolopyridine form | Substituents A and B reversed on triazolopyridine or triazolopyrimidine |
| J12 | 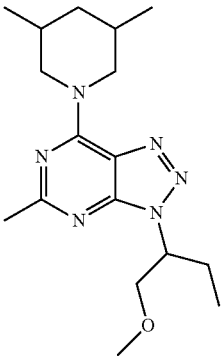 J12 | Triazolopyridine form | Substituents A and B reversed on triazolopyridine or triazolopyrimidine |
| J14 | 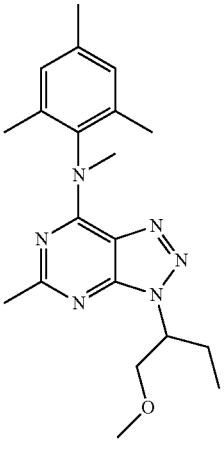 J14 | Triazolopyridine form | Substituents A and B reversed on triazolopyridine or triazolopyrimidine |

TABLE 5-continued

Illustrative, but non-limiting, list of triazolopyrimidine and/or a triazolopyridine compounds.

| Compound | Structure | Also contemplated | |
|---|---|---|---|
| J15 | (structure J15) | Triazolopyridine form | Substituents A and B reversed on triazolopyridine or triazolopyrimidine |
| J17 | (structure J17) | Triazolopyridine form | Substituents A and B reversed on triazolopyridine or triazolopyrimidine |
| J19 | (structure J19) | Triazolopyridine form | Substituents A and B reversed on triazolopyridine or triazolopyrimidine |

TABLE 5-continued

Illustrative, but non-limiting, list of triazolopyrimidine and/or a triazolopyridine compounds.

| Compound | Structure | Also contemplated | |
|---|---|---|---|
| J20 | 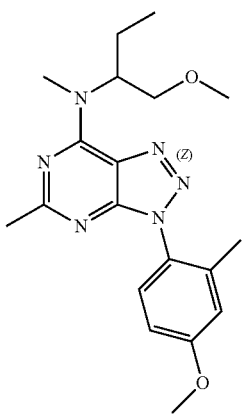<br>J20 | Triazolopyridine form | Substituents A and B reversed on triazolopyridine or triazolopyrimidine |
| J21 | 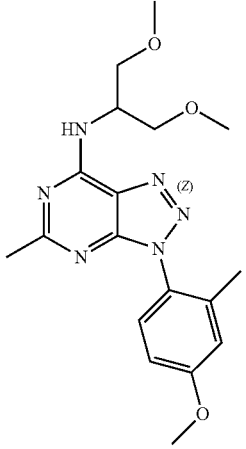<br>J21 | Triazolopyridine form | Substituents A and B reversed on triazolopyridine or triazolopyrimidine |
| J22 | 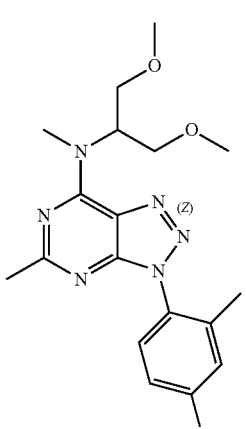<br>J22 | Triazolopyridine form | Substituents A and B reversed on triazolopyridine or triazolopyrimidine |

TABLE 5-continued

Illustrative, but non-limiting, list of triazolopyrimidine and/or a triazolopyridine compounds.

| Compound | Structure | Also contemplated | |
|---|---|---|---|
| J23 | 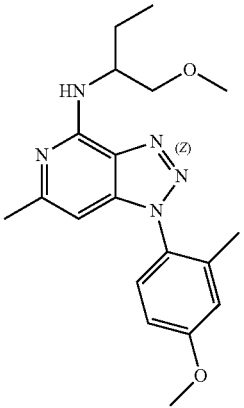 | Triazolopyridine form | Substituents A and B reversed on triazolopyridine or triazolopyrimidine |
| J24 | 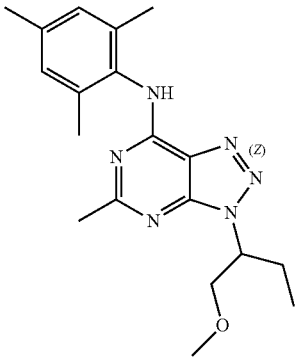 | Triazolopyridine form | Substituents A and B reversed on triazolopyridine or triazolopyrimidine |
| J25 | 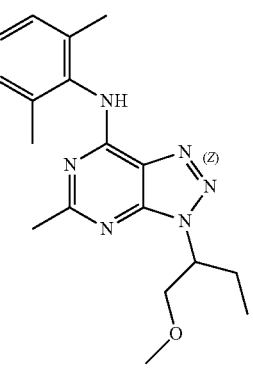 | Triazolopyridine form | Substituents A and B reversed on triazolopyridine or triazolopyrimidine |

In certain embodiments the compound comprises a compound selected from the group consisting of J06, J07, J11, J12, J14, J15, J19, J20, J21, J22, J23, J24, J25, or a pharmaceutically acceptable salt or solvate thereof. In certain embodiments the compound comprises a compound selected from the group consisting of J14, J19, J20, J21, J22, J23, J24, and J25, or a pharmaceutically acceptable salt or solvate thereof.

In certain embodiments, the compound described above is effective to decrease in corticotropin-releasing factor (CRF-1) induced p-tau.

In certain embodiments, any of the preceding compounds is provided as a racemic mixture.

In certain embodiments, any of the preceding compounds is a substantially pure S enantiomer.

In certain embodiments, any of the preceding compounds is a substantially pure R enantiomer.

Figure 1:
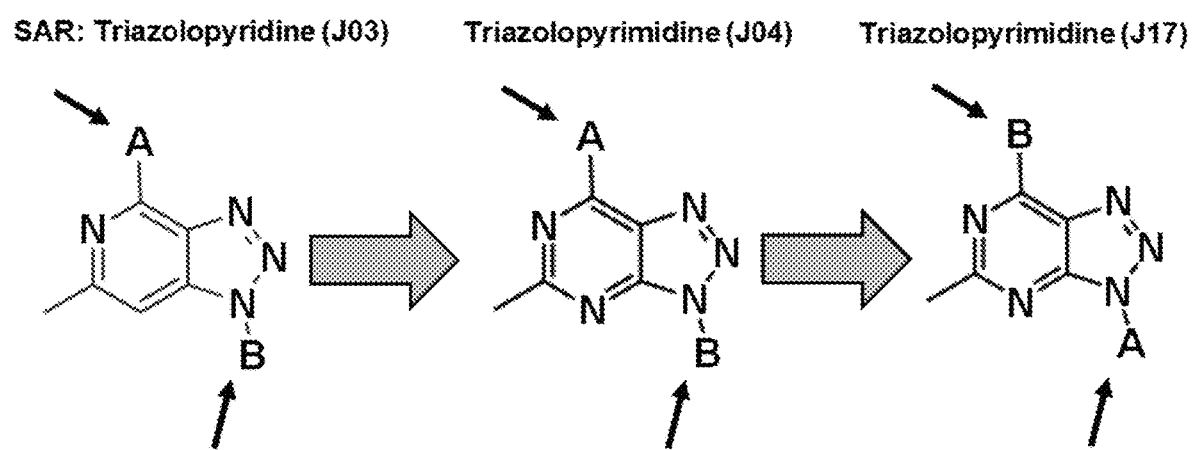
FIG. 1 illustrates design considerations in making J03 analogs.

It is to be noted (e.g., as indicated above in Table 5) that wherever a triazolopyrimidine is described herein the corresponding triazolopyridine (having the same substituents) is contemplated. Conversely, wherever a triazolopyridine is described herein the corresponding triazolopyrimidine (having the same substituents) is contemplated. Moreover, for any triazolopyrimidine having substituents A and B, e.g., as illustrated in FIG. 1, a triazolopyridine and a triazolopyrimidine having substituents A and B reversed is contemplated, and for any triazolopyrimidine having substituents A and B, e.g., as illustrated in FIG. 1, a triazolopyridine and a triazolopyrimidine having substituents A and B reversed is contemplated. Additionally, with respect to any of the triazolopyridines and a triazolopyrimidines described and/or contemplated herein, a racemic mixture of enantiomers is contemplated as well as a substantially pure (R) enantiomer or a substantially pure (S) enantiomer.

Figure 4:
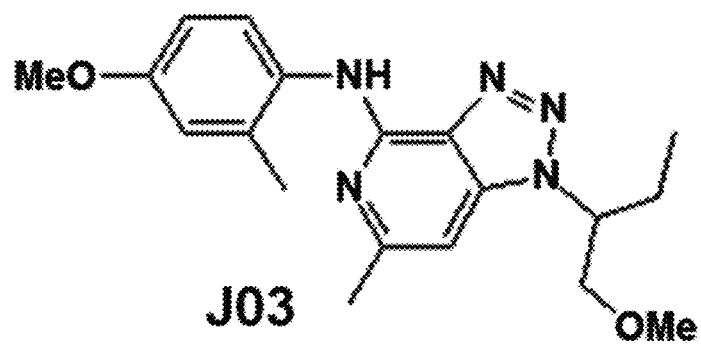
FIG. 4, panels A-C, show that J03 (panel A) reduces tau (panel B) and phospho-tau (panel C) increases induced by CRF. SHSY-5Y cells were cultured without serum to induce differentiation and increased tau expression.
Figure 4:
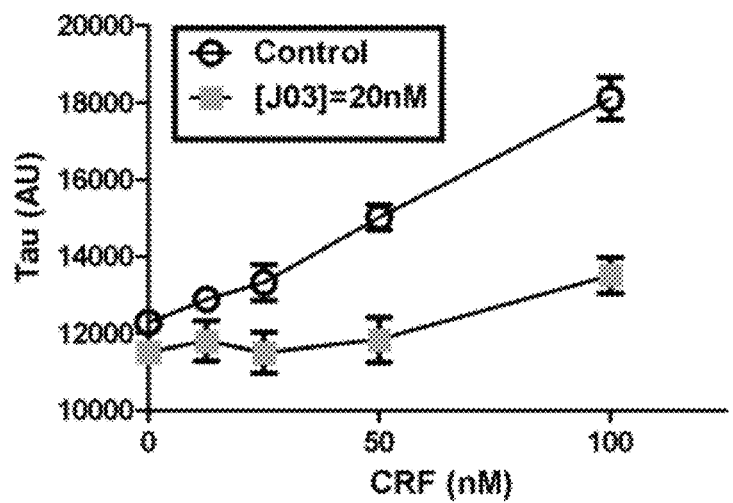
Figure 4:
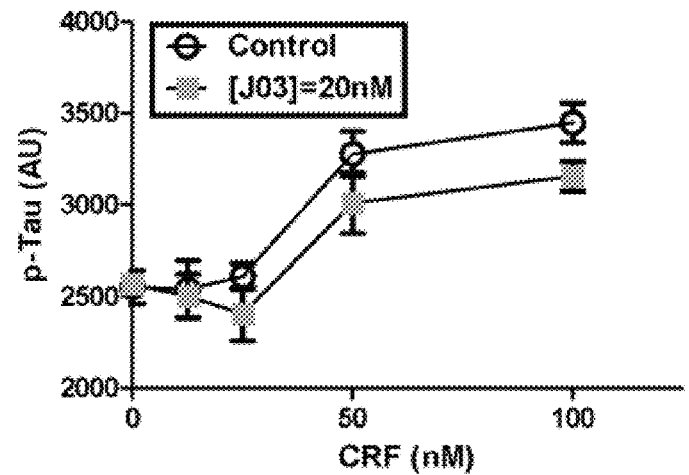

Various illustrative, but non-limiting triazolopyrimidine and/or triazolopyridines are also shown in FIGS. 2 and 4. In certain embodiments pharmaceutically acceptable salts, solvates, clathrates, tautomers, pharmaceutically acceptable salts of a tautomer, enantiomers thereof, and pharmaceutically acceptable salts of an enantiomer are contemplated.

Methods of preparing triazolopyrimidine(s) and/or triazolopyridine(s) such as are described herein are known to those of skill in the art. Generally, in one approach, the relevant triazolopyrimidine and/or triazolopyridine is illustrated in Example 1, below, describing the synthesis of J19. As illustrated therein, the synthesis of J19 involves the preparation of 6-Chloro-N4-substituted pyrimidine-4,5-diamine followed by a cyclisation to the triazolopyrimidine and displacement of the chlorine on the pyrimidine ring to yield the desired analog. A similar synthetic pathway would be used for the other analogs described herein. Additionally, a similar synthetic pathway would be used for the triazolopyridine series, the final product would involve separation of the pyridine isomers.

Figure 3:
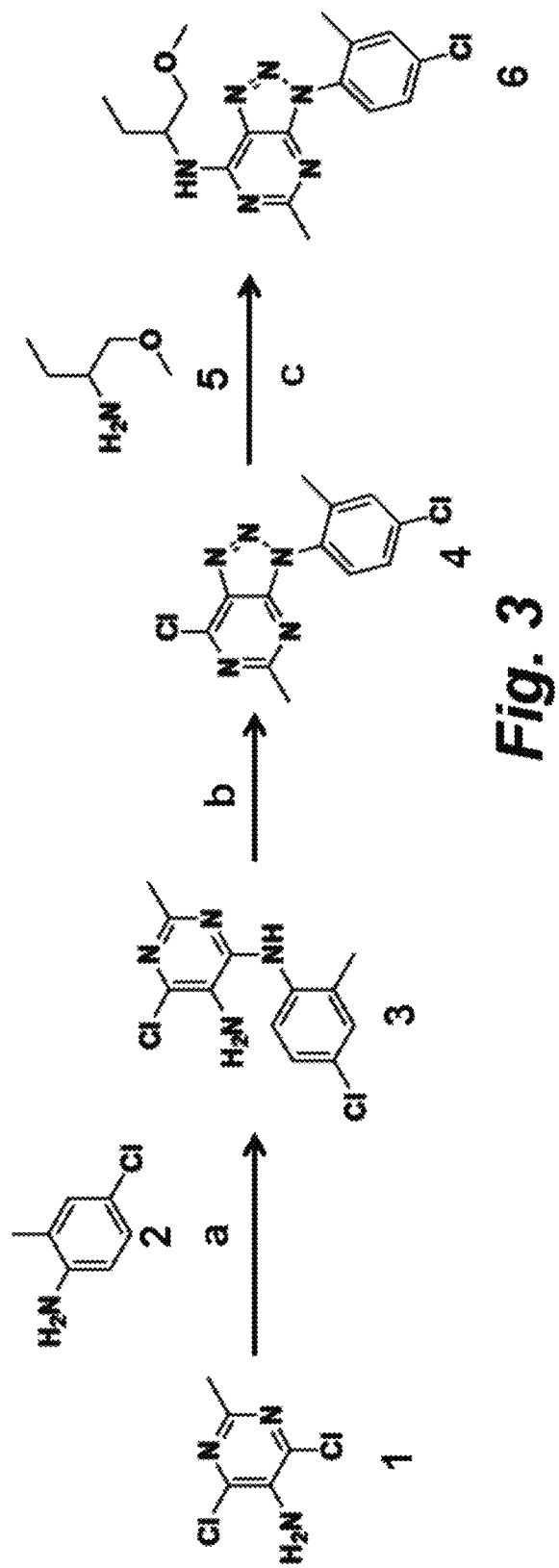
FIG. 3 illustrates a synthesis Scheme 1 for J19. Reagents and conditions: (a) 2-methoxyethanol, 125° C.; (b) NaNO$_2$, DCM, acetic acid, r.t; (c) THF, 100° C., sealed tube.

One illustrative, but non-limiting, protocol for the synthesis of J19 is provided in FIG. 3 and Example 1. Synthesis of additional compounds described herein are straightforward variations of the synthesis schemes provided herein.

The various active agents and synthesis schemes are intended to be illustrative and not limiting. Using the teachings provided herein, numerous other (e.g., triazolopyrimidine(s) and/or triazolopyridines or a tautomer(s) or stereoisomer(s) thereof, or pharmaceutically acceptable salts, solvates, or clathrates of said triazolopyrimidine and/or triazolopyridine(s), said stereoisomer(s), or said tautomer(s), or analogues, derivatives, or prodrugs thereof can be synthesized and identified by one of skill in the art.

Pharmaceutical Formulations.

In certain embodiments one or more active agents described herein (e.g., triazolopyrimidine(s) and/or triazolopyridines described herein, or a tautomer(s) or stereoisomer(s) thereof, or pharmaceutically acceptable salts, solvates, or clathrates of said triazolopyrimidine(s) and/or triazolopyridine(s), said stereoisomer(s), or said tautomer(s), or analogues, derivatives, or prodrugs thereof) are administered to a mammal in need thereof, e.g., to a mammal at risk for or suffering from a pathology characterized by abnormal processing of amyloid precursor proteins, a mammal at risk for progression of MCI to Alzheimer's disease, and so forth. In certain embodiments the active agent(s) are administered to prevent or delay the onset of a pre-Alzheimer's condition and/or cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by a non-amyloidogenic pathway.

In certain embodiments one or more active agents described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) are administered to a mammal in need thereof, e.g., to a mammal at risk for or suffering from a pathology characterized by abnormal processing of amyloid precursor proteins in conditions other than Alzheimer's disease of MCI. Illustrative conditions, include, but are not limited to AD-type symptoms of patients with Down's syndrome, glaucoma, macular degeneration (e.g., age-related macular degeneration (AMD), olfactory impairment. in the treatment of type-II diabetes, including diabetes associated with amyloidogenesis., neurodegenerative diseases such as scrapie, bovine spongiform encaphalopathies (e.g., BSE), traumatic brain injury ("TBI"), Creutzfeld-Jakob disease and the like, type II diabetes. Other conditions characterized by characterized by amyloid formation/deposition are contemplated. Such conditions include, but are not limited to Huntington's Disease, medullary carcinoma of the thyroid, cardiac arrhythmias, isolated atrial amyloidosis, atherosclerosis, rheumatoid arthritis, aortic medial amyloid, prolactinomas, familial amyloid polyneuropathy, hereditary non-neuropathic systemic amyloidosis, dialysis related amyloidosis, Finnish amyloidosis, Lattice corneal dystrophy, cerebral amyloid angiopathy (e.g., Icelandic type), systemic AL amyloidosis, sporadic inclusion body myositis, cerebrovascular dementia, and the like.

The active agent(s) (e.g., triazolopyrimidine(s) and/or triazolopyridines described herein) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience, and as described above.

For example, a pharmaceutically acceptable salt can be prepared for any of the agent(s) described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein (e.g., triazolopyrimidine(s) and/or triazolopyridines described herein, or a tautomer or stereoisomer thereof, or pharmaceutically acceptable salts or solvates of said triazolopyrimidine(s) and/or triazolopyridine(s), said stereoisomer(s), or said tautomer(s), or analogues, derivatives, or prodrugs thereof) are useful for parenteral administration, topical administration, oral administration, nasal administration (or otherwise inhaled), rectal administration, or local administration, such as by aerosol or transdermally, for prophylactic and/or therapeutic treatment of one or more of the pathologies/indications described herein (e.g., pathologies characterized by excess amyloid plaque formation and/or deposition or undesired amyloid or pre-amyloid processing).

In various embodiments the active agents described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., triazolopyrimidine(s) and/or triazolopyridine(s) described herein, or a tautomer(s) or stereoisomer(s) thereof, or pharmaceutically acceptable salts, solvates, or clathrates of said triazolopyrimidine(s) and/or triazolopyridine(s), said stereoisomer(s), or said tautomer(s), or analogues, derivatives, or prodrugs thereof) and the resulting composition is compressed. Where necessary the compressed product is coated, e.g., using known methods for masking the taste or for enteric dissolution or sustained release. Suitable coating materials include, but are not limited to ethyl-cellulose, hydroxymethylcellulose, POLYOX®yethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physiochemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

Pharmaceutical compositions comprising the active agents described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active agent(s) into preparations that can be used pharmaceutically. Proper formulation is dependent upon the route of administration chosen.

In certain embodiments, the active agents described herein are formulated for oral administration. For oral administration, suitable formulations can be readily formulated by combining the active agent(s) with pharmaceutically acceptable carriers suitable for oral delivery well known in the art. Such carriers enable the active agent(s) described herein to be formulated as tablets, pills, dragees, caplets, lizenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

For administration by inhalation, the active agent(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In various embodiments the active agent(s) can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) Suppositories, Pharmaceutical Press) and typically involve combining the active agents with a suitable base (e.g., hydrophilic (PEG), lipophilic materials such as cocoa butter or Witepsol W45, amphiphilic materials such as Suppocire AP and polyglycolized glyceride, and the like). The base is selected and compounded for a desired melting/delivery profile.

For topical administration the active agent(s) described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) can be formulated as solutions, gels, ointments, creams, suspensions, and the like as are well-known in the art.

In certain embodiments the active agents described herein are formulated for systemic administration (e.g., as an injectable) in accordance with standard methods well known to those of skill in the art. Systemic formulations include, but are not limited to, those designed for administration by injection, e.g. subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. Such penetrants are generally known in the art. Injectable formulations and inhalable formulations are generally provided as a sterile or substantially sterile formulation.

In addition to the formulations described previously, the active agent(s) may also be formulated as a depot preparations. Such long acting formulations can be administered by implantation (for example subcutaneously or intramuscularly) or by intramuscular injection. Thus, for example, the active agent(s) may be formulated with suitable polymeric or hydrophobic materials (for example as an emulsion in an acceptable oil) or ion exchange resins, or as sparingly soluble derivatives, for example, as a sparingly soluble salt.

In certain embodiments the active agent(s) described herein can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Alternatively, other pharmaceutical delivery systems can be employed. For example, liposomes, emulsions, and microemulsions/nanoemulsions are well known examples of delivery vehicles that may be used to protect and deliver pharmaceutically active compounds. Certain organic solvents such as dimethylsulfoxide also can be employed, although usually at the cost of greater toxicity.

In certain embodiments the active agent(s) described herein (e.g., triazolopyrimidine(s) and/or triazolopyridine(s) described herein, or a tautomer(s) or stereoisomer(s) thereof, or pharmaceutically acceptable salts, solvates or clathrates of said triazolopyrimidine(s) and/or triazolopyridine(s), said stereoisomer(s), or said tautomer(s), or analogues, derivatives, or prodrugs thereof) are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil in water (O/W) nanoemulsions include, but are not limited to: Surfactant micelles—micelles composed of small molecules surfactants or detergents (e.g., SDS/PBS/2-propanol); Polymer micelles—micelles composed of polymer, copolymer, or block copolymer surfactants (e.g., Pluronic L64/PBS/2-propanol); Blended micelles—micelles in which there is more than one surfactant component or in which one of the liquid phases (generally an alcohol or fatty acid compound) participates in the formation of the micelle (e.g., octanoic acid/PB S/EtOH); Integral micelles—blended micelles in which the active agent(s) serve as an auxiliary surfactant, forming an integral part of the micelle; and Pickering (solid phase) emulsions—emulsions in which the active agent(s) are associated with the exterior of a solid nanoparticle (e.g., polystyrene nanoparticles/PBS/no oil phase).

Illustrative water in oil (W/O) nanoemulsions include, but are not limited to: Surfactant micelles—micelles composed of small molecules surfactants or detergents (e.g., dioctyl sulfosuccinate/PBS/2-propanol, isopropylmyristate/PBS/2-propanol, etc.); Polymer micelles—micelles composed of polymer, copolymer, or block copolymer surfactants (e.g., PLURONIC® L121/PBS/2-propanol); Blended micelles—micelles in which there is more than one surfactant component or in which one of the liquid phases (generally an alcohol or fatty acid compound) participates in the formation of the micelle (e.g., capric/caprylic diglyceride/PBS/EtOH); Integral micelles—blended micelles in which the active agent(s) serve as an auxiliary surfactant, forming an integral part of the micelle (e.g., active agent/PBS/polypropylene glycol); and Pickering (solid phase) emulsions—emulsions in which the active agent(s) are associated with the exterior of a solid nanoparticle (e.g., chitosan nanoparticles/no aqueous phase/mineral oil).

As indicated above, in certain embodiments the nanoemulsions comprise one or more surfactants or detergents. In some embodiments the surfactant is a non-anionic detergent (e.g., a polysorbate surfactant, a polyoxyethylene ether, etc.). Surfactants that find use in the present invention include, but are not limited to surfactants such as the TWEEN®, TRITON®, and TYLOXAPOL® families of compounds.

In certain embodiments the emulsions further comprise one or more cationic halogen containing compounds, including but not limited to, cetylpyridinium chloride. In still further embodiments, the compositions further comprise one or more compounds that increase the interaction ("interaction enhancers") of the composition with microorganisms (e.g., chelating agents like ethylenediaminetetraacetic acid, or ethylenebis(oxyethylenenitrilo)tetraacetic acid in a buffer).

In some embodiments, the nanoemulsion further comprises an emulsifying agent to aid in the formation of the emulsion. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their anti-pathogenic properties.

In addition to discrete oil droplets dispersed in an aqueous phase, certain oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (see e.g., Hamouda et al. (1998) *J. Infect. Disease* 180: 1939).

In certain embodiments the emulsion comprises a discontinuous oil phase distributed in an aqueous phase, a first component comprising an alcohol and/or glycerol, and a second component comprising a surfactant or a halogen-containing compound. The aqueous phase can comprise any type of aqueous phase including, but not limited to, water (e.g., dionized water, distilled water, tap water) and solutions (e.g., phosphate buffered saline solution or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In certain embodiments, the oil phase comprises 30-90 vol % of the oil-in-water emulsion (e.g., constitutes 30-90% of the total volume of the final emulsion), more preferably 50-80%. The formulations need not be limited to particular surfactants, however in certain embodiments, the surfactant is a polysorbate surfactant (e.g., TWEEN 20®, TWEEN 40®, TWEEN 60®, and TWEEN 80®), a pheoxypolyethoxyethanol (e.g., TRITON® X-100, X-301, X-165, X-102, and X-200, and TYLOXAPOL®), or sodium dodecyl sulfate, and the like.

In certain embodiments a halogen-containing component is present. the nature of the halogen-containing compound, in some embodiments the halogen-containing compound comprises a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, tetradecyltrimethylammonium bromide, and the like In certain embodiments the emulsion comprises a quaternary ammonium compound. Quaternary ammonium compounds include, but are not limited to, N-alkyldimethyl benzyl ammonium saccharinate, 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl dimethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, an d5,152,923 and in Fanun et al. (2009) Microemulsions: Properties and Applications (Surfactant Science), CRC Press, Boca Ratan Fl.

In certain embodiments, one or more active agents described herein can be provided as a "concentrate", e.g., in a storage container (e.g., in a premeasured volume) ready for dilution, or in a soluble capsule ready for addition to a volume of water, alcohol, hydrogen peroxide, or other diluent.

Extended Release (Sustained Release) Formulations.

In certain embodiments "extended release" formulations of the active agent(s) described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) are contemplated. In various embodiments such extended release formulations are designed to avoid the high peak plasma levels of intravenous and conventional immediate release oral dosage forms.

Illustrative sustained-release formulations include, for example, semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization can be employed.

In certain embodiments such "extended release" formulations utilize the mucosa and can independently control tablet disintegration (or erosion) and/or drug dissolution and release from the tablet over time to provide a safer delivery profile. In certain embodiments the oral formulations of active agent(s) described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) provide individual, repetitive doses that include a defined amount of the active agent that is delivered over a defined amount of time.

One illustrative sustained release formulation is a substantially homogeneous composition that comprises about 0.01% to about 99% w/w, or about 0.1% to about 95%, or about 0.1%, or about 1%, or about 2%, or about 5%, or about 10%, or about 15%, or about 20% to about 80%, or to about 90%, or to about 95%, or to about 97%, or to about 98%, or to about 99%1 of the active ingredient(s) (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) and one or more mucoadhesives (also referred to herein as "bioadhesives") that provide for adherence to the targeted mucosa of the subject (patient) and that may further comprise one or more of the following: one or more binders that provide binding of the excipients in a single tablet; one or more hydrogel forming excipients; one or more bulking agents; one or more lubricants; one or more glidants; one or more solubilizers; one or more surfactants; one or more flavors; one or more disintegrants; one or more buffering excipients; one or more coatings; one or more controlled release modifiers; and one or more other excipients and factors that modify and control the drug's dissolution or disintegration time and kinetics or protect the active drug from degradation.

In various embodiments a sustained release pharmaceutical dosage form for oral transmucosal delivery can be solid or non-solid. In one illustrative embodiment, the dosage form is a solid that turns into a hydrogel following contact with saliva.

Suitable excipients include, but are not limited to substances added to the formulations that are required to produce a commercial product and can include, but are not limited to: bulking agents, binders, surfactants, bioadhesives, lubricants, disintegrants, stabilizers, solubilizers, glidants, and additives or factors that affect dissolution or disintegration time. Suitable excipients are not limited to those above, and other suitable nontoxic pharmaceutically acceptable carriers for use in oral formulations can be found in Remington's Pharmaceutical Sciences, 17th Edition, 1985.

In certain embodiments extended release formulations of the active agent(s) described herein for oral transmucosal drug delivery include at least one bioadhesive (mucoadhesive) agent or a mixture of several bioadhesives to promote adhesion to the oral mucosa during drug delivery. In addition the bioadhesive agents may also be effective in controlling the dosage form erosion time and/or, the drug dissolution kinetics over time when the dosage form is wetted. Such mucoadhesive drug delivery systems are very beneficial, since they can prolong the residence time of the drug at the site of absorption and increase drug bioavailability. The mucoadhesive polymers forming hydrogels are typically hydrophilic and swellable, containing numerous hydrogen bond-forming groups, like hydroxyl, carboxyl or amine, which favor adhesion. When used in a dry form, they attract water from the mucosal surface and swell, leading to polymer/mucus interaction through hydrogen bonding, electrostatic, hydrophobic or van der Waals interaction.

Illustrative suitable mucoadhesive or bioadhesive materials, include, but are not limited to natural, synthetic or biological polymers, lipids, phospholipids, and the like. Examples of natural and/or synthetic polymers include cellulosic derivatives (such as methylcellulose, carboxymethyl cellulose, hydroxyethyl cellulose, hydroxyethylmethyl cellulose, etc), natural gums (such as guar gum, xanthan gum, locust bean gum, karaya gum, veegum etc.), polyacrylates (such as CARBOPOL®, polycarbophil, etc), alginates, thiol-containing polymers, POLYOX®yethylenes, polyethylene glycols (PEG) of all molecular weights (preferably between 1000 and 40,000 Da, of any chemistry, linear or branched), dextrans of all molecular weights (preferably between 1000 and 40,000 Da of any source), block copolymers, such as those prepared by combinations of lactic and glycolic acid (PLA, PGA, PLGA of various viscosities, molecular weights and lactic-to-glycolic acid ratios) polyethylene glycol-polypropylene glycol block copolymers of any number and combination of repeating units (such as PLURONICS®, TEKTRONIX® or GENAPOL® block copolymers), combination of the above copolymers either physically or chemically linked units (for example PEG-PLA or PEG-PLGA copolymers) mixtures. Preferably the bioadhesive excipient is selected from the group of polyethylene glycols, POLYOX®yethylenes, polyacrylic acid polymers, such as CARBOPOL® (such as CARBOPOL® 71G, 934P, 971P, 974P, and the like) and polycarbophils (such as NOVEON® AA-1, NOVEON® CA-1, NOVEON® CA-2, and the like), cellulose and its derivatives and most preferably it is polyethylene glycol, carbopol, and/or a cellulosic derivative or a combination thereof.

In certain embodiments the mucoadhesive/bioadhesive excipient is typically present at 1-50% w/w, preferably 1-40% w/w or most preferably between 5-30% w/w. A particular formulation may contain one or more different bioadhesives in any combination.

In certain embodiments the formulations for oral transmucosal drug delivery also include a binder or mixture of two or more binders which facilitate binding of the excipients into a single dosage form. Illustrative binders include, binders selected from the group consisting of cellulosic derivatives (such as methylcellulose, carboxymethyl cellulose, hydroxyethyl cellulose, hydroxyethylmethyl cellulose, etc.), polyacrylates (such as CARBOPOL®, polycarbophil, etc.), POVIDONE® (all grades), POLYOX®® of any molecular weight or grade, irradiated or not, starch, polyvinylpyrrolidone (PVP), AVICEL®, and the like. In certain embodiments the binder is typically present at 0.5-60% w/w, preferably 1-30% w/w and most preferably 1.5-15% w/w.

In certain embodiments the formulations also include at least one hydrogel-forming excipient. Illustrative hydrogel forming excipients include, but are not limited to those selected from the group consisting of polyethylene glycols and other polymers having an ethylene glycol backbone, whether homopolymers or cross linked heteropolymers, block copolymers using ethylene glycol units, such as POLYOX®ethylene homopolymers (such as POLYOX®® N10/MW=100,000 POLYOX®-80/MW=200,000; POLYOX® 1105/MW=900,000; POLYOX®-301/MW=4,000,000; POLYOX®-303/MW=7,000,000, POLYOX® WSR-N-60K, all of which are tradenames of Union Carbide), hydroxypropylmethylcellylose (HPMC) of all molecular weights and grades (such as METOLOSE® 90SH50000, METOLOSE® 90SH30000, all of which are tradenames of Shin-Etsu Chemical company), Poloxamers (such as LUTROL® F-68, LUTROL® F-127, F-105 etc., all tradenames of BASF Chemicals), GENAPOL®, polyethylene glycols (PEG, such as PEG-1500, PEG-3500, PEG-4000, PEG-6000, PEG-8000, PEG-12000, PEG-20,000, etc.), natural gums (xanthan gum, locust bean gum, etc.) and cellulose derivatives (HC, HMC, HMPC, HPC, CP, CMC), polyacrylic acid-based polymers either as free or cross-linked and combinations thereof, biodegradable polymers such as poly lactic acids, polyglycolic acids and any combination thereof, whether a physical blend or cross-linked. In certain embodiments, the hydrogel components may be cross-linked. The hydrogel forming excipient(s) are typically present at 0.1-70% w/w, preferably 1-50% w/w or most preferably 1-30% w/w.

In certain embodiments the formulations may also include at least one controlled release modifier which is a substance that upon hydration of the dosage form will preferentially adhere to the drug molecules and thus reduce the rate of its diffusion from the oral dosage form. Such excipients may also reduce the rate of water uptake by the formulation and thus enable a more prolonged drug dissolution and release from the tablet. In general the selected excipient(s) are lipophilic and capable of naturally complexing to the hydrophobic or lipophilic drugs. The degree of association of the release modifier and the drug can be varied by altering the modifier-to-drug ratio in the formulation. In addition, such interaction may be appropriately enhanced by the appropriate combination of the release modifier with the active drug in the manufacturing process. Alternatively, the controlled release modifier may be a charged polymer either synthetic or biopolymer bearing a net charge, either positive or negative, and which is capable of binding to the active via electrostatic interactions thus modifying both its diffusion through the tablet and/or the kinetics of its permeation through the mucosal surface. Similarly to the other compounds mentioned above, such interaction is reversible and does not involve permanent chemical bonds with the active. In certain embodiments the controlled release modifier may typically be present at 0-80% w/w, preferably 1-20% w/w, most preferably 1-10% w/w.

In various embodiments the extended release formulations may also include other conventional components required for the development of oral dosage forms, which are known to those skilled in the art. These components may include one or more bulking agents (such as lactose USP, Starch 1500, mannitol, sorbitol, malitol or other non-reducing sugars; microcrystalline cellulose (e.g., AVICEL®), dibasic calcium phosphate dehydrate, sucrose, and mixtures thereof), at least one solubilizing agent(s) (such as cyclodextrins, pH adjusters, salts and buffers, surfactants, fatty acids, phospholipids, metals of fatty acids etc.), metal salts and buffers organic (such as acetate, citrate, tartrate, etc.) or inorganic (phosphate, carbonate, bicarbonate, borate, sulfate, sulfite, bisulfite, metabisulfite, chloride, etc.), salts of metals such as sodium, potassium, calcium, magnesium, etc.), at least one lubricant (such as stearic acid and divalent cations of, such as magnesium stearate, calcium stearate, etc., talc, glycerol monostearate and the like), one or more glidants (such as colloidal silicon dioxide, precipitated silicon dioxide, fumed silica (CAB-O-SIL® M-5P, trademark of Cabot Corporation), stearowet and sterotex, silicas (such as SILOID® and SILOX® silicas-trademarks of Grace Davison Products, Aerosil—trademark of Degussa Pharma), higher fatty acids, the metal salts thereof, hydrogenated vegetable oils and the like), flavors or sweeteners and colorants (such as aspartame, mannitol, lactose, sucrose, other artificial sweeteners; ferric oxides and FD&C lakes), additives to help stabilize the drug substance from chemical of physical degradation (such as anti-oxidants, anti-hydrolytic agents, aggregation-blockers etc. Anti-oxidants may include BHT, BHA, vitamins, citric acid, EDTA, sodium bisulfate, sodium metabisulfate, thiourea, methionine, surfactants, amino-acids, such as arginine, glycine, histidine, methionine salts, pH adjusters, chelating agents and buffers in the dry or solution form), one or more excipients that may affect tablet disintegration kinetics and drug release from the tablet, and thus pharmacokinetics (disintegrants such as those known to those skilled in the art and may be selected from a group consisting of starch, carboxy-methylcellulose type or crosslinked polyvinyl pyrrolidone (such as cross-povidone, PVP-XL), alginates, cellulose-based disintegrants (such as purified cellulose, methylcellulose, crosslinked sodium carboxy methylcellulose (Ac-Di-Sol) and carboxy methyl cellulose), low substituted hydroxypropyl ethers of cellulose, microcrystalline cellulose (such as AVICEL®), ion exchange resins (such as AMBRELITE® IPR 88), gums (such as agar, locust bean, karaya, pectin and tragacanth), guar gums, gum karaya, chitin and chitosan, smecta, gellan gum, isapghula husk, polacrillin potassium (Tulsion[339]), gas-evolving disintegrants (such as citric acid and tartaric acid along with the sodium bicarbonate, sodium carbonate, potassium bicarbonate or calcium carbonate), sodium starch glycolate (such as EXPLOTAB® and PRIMOGEL®), starch DC and the likes, at least one biodegradable polymer of any type useful for extended drug release. Exemplary polymer compositions include, but are not limited to, polyanhydrides and co-polymers of lactic acid and glycolic acid, poly(dl-lactide-co-glycolide) (PLGA), poly(lactic acid) (PLA), poly(glycolic acid) (PGA), polyorthoesters, proteins, and polysaccharides.

In certain embodiments, the active agent(s) can be chemically modified to significantly modify the pharmacokinetics in plasma. This may be accomplished for example by conjugation with poly(ethylene glycol) (PEG), including site-specific PEGylation. PEGylation, which may improve drug performance by optimizing pharmacokinetics, decreasing immunogenicity and dosing frequency.

Methods of making a formulation of the active agent(s) described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) for GI or oral transmucosal delivery are also provided. One method includes the steps of powder grinding, dry powder mixing and tableting via direct compression. Alternatively, a wet granulation process may be used. Such a method (such as high shear granulation process) involves mixing the active ingredient and possibly some excipients in a mixer. The binder may be one of the excipients added in the dry mix state or dissolved in the fluid used for granulating. The granulating solution or suspension is added to the dry powders in the mixer and mixed until the desired characteristics are achieved. This usually produces a granule that will be of suitable characteristics for producing dosage forms with adequate dissolution time, content uniformity, and other physical characteristics. After the wet granulation step, the product is most often dried and/or then milled after drying to get a major percentage of the product within a desired size range. Sometimes, the product is dried after being wet sized using a device such as an oscillating granulator, or a mill. The dry granulation may then processed to get an acceptable size range by first screening with a sieving device, and then milling the oversized particles.

Additionally, the formulation may be manufactured by alternative granulation processes, all known to those skilled in the art, such as spray fluid bed granulation, extrusion and spheronization or fluid bed rotor granulation.

Additionally, the tablet dosage form of the active agent(s) described herein may be prepared by coating the primary tablet manufactured as described above with suitable coatings known in the art. Such coatings are meant to protect the active cores against damage (abrasion, breakage, dust formation) against influences to which the cores are exposed during transport and storage (atmospheric humidity, temperature fluctuations), and naturally these film coatings can also be colored. The sealing effect of film coats against water vapor is expressed by the water vapor permeability. Coating may be performed by one of the available processes such as Wurster coating, dry coating, film coating, fluid bed coating, pan coating, etc. Typical coating materials include polyvinyl pyrrolidone (PVP), polyvinyl pyrrolidone vinyl acetate copolymer (PVPVA), polyvinyl alcohol (PVA), polyvinyl alcohol/polyethylene glycol copolymer (PVA/PEG), cellulose acetate phthalate, ethyl cellulose, gellan gum, maltodextrin, methacrylates, methyl cellulose, hydroxyl propyl methyl cellulose (HPMC of all grades and molecular weights), carrageenan, shellac and the like.

In certain embodiments the tablet core comprising the active agent(s) described herein can be coated with a bioadhesive and/or pH resistant material to enable material, such as those defined above, to improve bioadhesion of the tablet in the sublingual cavity.

In certain embodiments, the active agent(s) described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) are formulated as inclusion complexes. While not limited to cyclodextrin inclusion complexes, it is noted that cyclodextrin is the agent most frequently used to form pharmaceutical inclusion complexes. Cyclodextrins (CD) are cyclic oligomers of glucose, that typically contain 6, 7, or 8 glucose monomers joined by α-1,4 linkages. These oligomers are commonly called α-CD, β-CD, and γ-CD, respectively. Higher oligomers containing up to 12 glucose monomers are known, and contemplated to in the formulations described herein. Functionalized cyclodextrin inclusion complexes are also contemplated. Illustrative, but non-limiting functionalized cyclodextrins include, but are not limited to sulfonates, sulfonates and sulfinates, or disulfonates of hydroxybutenyl cyclodextrin; sulfonates, sulfonates and sulfinates, or disulfonates of mixed ethers of cyclodextrins where at least one of the ether substituents is hydroxybutenyl cyclodextrin. Illustrative cyclodextrins include a polysaccharide ether which comprises at least one 2-hydroxybutenyl substituent, wherein the at least one hydroxybutenyl substituent is sulfonated and sulfinated, or disulfonated, and an alkylpolyglycoside ether which comprises at least one 2-hydroxybutenyl substituent, wherein the at least one hydroxybutenyl substituent is sulfonated and sulfinated, or disulfonated. In various embodiments inclusion complexes formed between sulfonated hydroxybutenyl cyclodextrins and one or more of the active agent(s) described herein are contemplated. Methods of preparing cyclodextrins, and cyclodextrin inclusion complexes are found for example in U.S. Patent Publication No: 2004/0054164 and the references cited therein and in U.S. Patent Publication No: 2011/0218173 and the references cited therein.

Pharmacokinetics (PK) and Formulation Attributes

One advantage of the extended (controlled) release oral (GI or transmucosal) formulations described herein is that they can maintain the plasma drug concentration within a targeted therapeutic window for a longer duration than with immediate-release formulations, whether solid dosage forms or liquid-based dosage forms. The high peak plasma levels typically observed for such conventional immediate release formulations will be blunted by the prolonged release of the drug over 1 to 12 hours or longer. In addition, a rapid decline in plasma levels will be avoided since the drug will continually be crossing from the oral cavity into the bloodstream during the length of time of dissolution of the tablet, thus providing plasma pharmacokinetics with a more stable plateau. In addition, the dosage forms described herein may improve treatment safety by minimizing the potentially deleterious side effects due to the reduction of the peaks and troughs in the plasma drug pharmacokinetics, which compromise treatment safety.

In various embodiments the oral transmucosal formulations of the active agent(s) described herein designed to avoid the high peak plasma levels of intravenous and conventional immediate release oral dosage forms by utilizing the mucosa and by independently controlling both tablet disintegration (or erosion) and drug dissolution and release from the tablet over time to provide a safer delivery profile. The oral formulations described herein provide individual, repetitive doses that include a defined amount of the active agent.

An advantage of the bioadhesive oral transmucosal formulations described herein is that they exhibit highly consistent bioavailability and can maintain the plasma drug concentration within a targeted therapeutic window with significantly lower variability for a longer duration than currently available dosage forms, whether solid dosage forms or IV dosage forms. In addition, a rapid decline in plasma levels is avoided since the drug is continually crossing from the oral cavity or GI tract into the bloodstream during the length of time of dissolution of the tablet or longer, thus providing plasma pharmacokinetics with an extended plateau phase as compared to the conventional immediate release oral dosage forms. Further, the dosage forms described herein can improve treatment safety by minimizing the potentially deleterious side effects due to the relative reduction of the peaks and troughs in the plasma drug pharmacokinetics, which compromise treatment safety and is typical of currently available dosage forms.

In various embodiments bioadhesive formulations described herein can be designed to manipulate and control the pharmacokinetic profile of the active agent(s) described herein. As such, the formulations can be adjusted to achieve 'slow' disintegration times (and erosion kinetic profiles) and slow drug release and thus enable very prolonged pharmacokinetic profiles that provide sustained drug action. Although such formulations may be designed to still provide a fast onset, they are mostly intended to enable the sustained drug PK and effect while maintaining the other performance attributes of the tablet such as bioadhesion, reproducibility of action, blunted $C_{max}$, etc.

The performance and attributes of the bioadhesive transmucosal formulations of this invention are independent of the manufacturing process. A number of conventional, well-established and known in the art processes can be used to manufacture the formulations of the present invention (such as wet and dry granulation, direct compression, etc.) without impacting the dosage form physicochemical properties or in vivo performance.

An illustrative mathematical ratio that demonstrates the prolonged plateau phase of the measured blood plasma levels of the active agent(s) described herein, following administration of the dosage forms of the invention is the term "Optimal Therapeutic Targeting Ratio" or "OTTR", which represents the average time that the drug is present at therapeutic levels, defined as time within which the drug plasma concentration is maintained above 50% of $C_{max}$ normalized by the drug's elimination half-life multiplied by the ratio of the $C_{max}$ obtained in the dosage form of interest over the normalized $C_{max}$ following IV administration of equivalent doses. In certain embodiments the OTTR can be calculated by the formula:

$$OTTR=(CV_{max}/C_{max})\times(Dose/Dose^{IV}) \text{ (Time above 50\% of } C_{max})/(\text{Terminal}^{IV} \text{ elimination half-life of the drug)}.$$

In certain embodiments the OTTR is greater than about 15, or greater than about 20, or greater than about 25, or greater than about 30, or greater than about 40, or greater than about 50.

Administration

In certain embodiments one or more active agents described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) are administered to a mammal in need thereof, e.g., to a mammal at risk for or suffering from a pathology characterized by abnormal processing of amyloid precursor proteins, a mammal at risk for progression of MCI to Alzheimer's disease, and so forth. In certain embodiments the active agent(s) are administered to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by a non-amyloidogenic pathway. In certain embodiments one or more active agent(s) are administered for the treatment of early stage, mid stage, or late-stage Alzheimer's disease, e.g., to reduce the severity of the disease, and/or to ameliorate one or more symptoms of the disease, and/or to slow the progression of the disease.

In various embodiments the active agent(s) described herein (e.g., triazolopyrimidine(s) and/or triazolopyridine(s) described herein, or a tautomer(s) or stereoisomer(s) thereof, or pharmaceutically acceptable salts or solvates of said triazolopyrimidine(s) and/or triazolopyridine(s), said stereoisomer(s), or said tautomer(s), or analogues, derivatives, or prodrugs thereof) can be administered by any of a number of routes. Thus, for example they can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. Typically the dosage form is selected to facilitate delivery to the brain (e.g., passage through the blood brain barrier). In this context it is noted that the compounds described herein are readily delivered to the brain. Dosage forms known to those of skill in the art are suitable for delivery of the compound.

In various embodiments the active agent(s) are administered in an amount/dosage regimen sufficient to exert a prophylactically and/or therapeutically useful effect in the absence of undesirable side effects on the subject treated (or with the presence of acceptable levels and/or types of side effects). The specific amount/dosage regimen will vary depending on the weight, gender, age and health of the individual; the formulation, the biochemical nature, bioactivity, bioavailability and the side effects of the particular compound.

In certain embodiments the therapeutically or prophylactically effective amount may be determined empirically by testing the agent(s) in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

In certain embodiments, when administered orally, an administered amount of the agent(s) described herein effective to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by a non-amyloidogenic pathway, and/or to treat or prevent AD ranges from about 0.1 mg/day to about 500 mg/day or about 1,000 mg/day, or from about 0.1 mg/day to about 200 mg/day, for example, from about 1 mg/day to about 100 mg/day, for example, from about 5 mg/day to about 50 mg/day. In some embodiments, the subject is administered the compound at a dose of about 0.05 to about 0.50 mg/kg, for example, about 0.05 mg/kg, 0.10 mg/kg, 0.20 mg/kg, 0.33 mg/kg, 0.50 mg/kg. It is understood that while a patient may be started at one dose, that dose may be varied (increased or decreased, as appropriate) over time as the patient's condition changes. Depending on outcome evaluations, higher doses may be used. For example, in certain embodiments, up to as much as 1000 mg/day can be administered, e.g., 5 mg/day, 10 mg/day, 25 mg/day, 50 mg/day, 100 mg/day, 200 mg/day, 300 mg/day, 400 mg/day, 500 mg/day, 600 mg/day, 700 mg/day, 800 mg/day, 900 mg/day or 1000 mg/day.

In various embodiments, active agent(s) described herein can be administered parenterally, for example, by IV, IM, depo-IM, SC, or depo-SC. In certain embodiments when administered parenterally, a therapeutically effective amount of about 0.5 to about 100 mg/day, preferably from about 5 to about 50 mg daily can be delivered. When a depot formulation is used for injection once a month or once every two weeks, the dose in certain embodiments can be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

In various embodiments, the active agent(s) described herein can be administered sublingually. In some embodiments, when given sublingually, the compounds and/or analogs thereof can be given one to four times daily in the amounts described above for IM administration.

In various embodiments, the active agent(s) described herein can be administered intranasally. When given by this route, the appropriate dosage forms are a nasal spray or dry powder, as is known to those skilled in the art. In certain embodiments, the dosage of compound and/or analog thereof for intranasal administration is the amount described above for IM administration.

In various embodiments, the active agent(s) described herein can be administered intrathecally. When given by this route the appropriate dosage form can be a parenteral dosage form as is known to those skilled in the art. In certain embodiments, the dosage of compound and/or analog thereof for intrathecal administration is the amount described above for IM administration.

In certain embodiments, the active agent(s) described herein can be administered topically. When given by this route, the appropriate dosage form is a cream, ointment, or patch. When administered topically, the dosage is from about 1.0 mg/day to about 200 mg/day. Because the amount that can be delivered by a patch is limited, two or more patches may be used. The number and size of the patch is not important as long as a therapeutically effective amount of compound be delivered as is known to those skilled in the art. The compound can be administered rectally by suppository as is known to those skilled in the art. In certain embodiments, when administered by suppository, the therapeutically effective amount is from about 1.0 mg to about 500 mg.

In various embodiments, the active agent(s) described herein can be administered by implants as is known to those skilled in the art. When administering the compound by implant, the therapeutically effective amount is the amount described above for depot administration.

In various embodiments, the active agent(s) described herein thereof can be enclosed in multiple or single dose containers. The enclosed agent(s) can be provided in kits, for example, including component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In various embodiments the dosage forms can be administered to the subject 1, 2, 3, or 4 times daily. In certain embodiments it is preferred that the compound be administered either three or fewer times, more preferably once or twice daily. In certain embodiments, it is preferred that the agent(s) be administered in oral dosage form.

It should be apparent to one skilled in the art that the exact dosage and frequency of administration will depend on the particular condition being treated, the severity of the condition being treated, the age, weight, general physical condition of the particular patient, and other medication the individual may be taking as is well known to administering physicians who are skilled in this art.

While the compositions and methods are described herein with respect to use in humans, they are also suitable for animal, e.g., veterinary use. Thus certain organisms (subjects) contemplated herein include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Combination Therapies

In certain embodiments, the active agent(s) described herein (e.g., triazolopyrimidine(s) and/or triazolopyridine(s) described herein, or a tautomer(s) or stereoisomer(s) thereof, or pharmaceutically acceptable salts, solvates, or clathrates of said compounds, said stereoisomer(s), or said tautomer(s), or analogues, derivatives, or prodrugs thereof) can be used in combination with other therapeutic agents or approaches used to treat or prevent diseases characterized by amyloid deposits in the brain, including MCI and/or AD. Accordingly, in certain embodiments, a pharmaceutical composition comprising at least one active agent described herein (e.g., a triazolopyrimidine and/or triazolopyridine described herein, or a tautomer or stereoisomer thereof, or pharmaceutically acceptable salt, solvate, or clathrate of said triazolopyrimidine and/or triazolopyridine, said stereoisomer, or said tautomer, or an analogue, derivative, or prodrug thereof) one together with at least one additional therapeutic agent, and, optionally, a pharmaceutically acceptable carrier or diluent is contemplated. In certain embodiments a therapeutic or prophylactic method comprising administering at least active agent described herein in conjunction with at least one additional therapeutic agent is contemplated.

In certain embodiments non-limiting examples of additional therapeutic agents include, but are not limited to disulfiram and/or analogues thereof, honokiol and/or analogues thereof, tropisetron and/or analogues thereof, nimetazepam and/or analogues thereof (see, e.g., U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein), tropinol-esters and/or related esters and/or analogues thereof (see, e.g., U.S. Ser. No. 61/514,381, which is incorporated herein by reference for the compounds described herein), TrkA kinase inhibitors (e.g., ADDN-1351) and/or analogues thereof (see, e.g., U.S. Ser. No. 61/525,076, which is incorporated herein by reference for the compounds described therein), hydantoins and/or analogues thereof (see, e.g., PCT/US2014/016100 (WO 2014/127042 A1), which is incorporated herein by reference for the compounds described therein, D2 receptor agonists and alpha1-adrenergic receptor antagonists, and APP-specific BACE Inhibitors (ASBIs) as described and/or claimed in PCT/US2013/032481 (WO 2013/142370 A1) and U.S. Ser. No. 14/384,641 which are incorporated herein by reference for the active agents described therein including, but not limited to galangin, a galangin prodrug, rutin, a rutin prodrug, and other flavonoids and flavonoid prodrugs as described or claimed therein.

Non-limiting examples of additional therapeutic agents include drugs selected from the group consisting of: (a) drugs useful for the treatment of Alzheimer's disease and/or drugs useful for treating one or more symptoms of Alzheimer's disease, (b) drugs useful for inhibiting the synthesis Aβ, and (c) drugs useful for treating neurodegenerative diseases. Additional non-limiting examples of additional therapeutic agents for use in combination with the compounds (e.g., triazolopyrimidine and/or triazolopyridine) described herein include drugs useful for the treatment, prevention, delay of onset, amelioration of any pathology associated with Aβ and/or a symptom thereof. Non-limiting examples of pathologies associated with Aβ include: Alzheimer's disease, Down's syndrome, Parkinson's disease, memory loss, memory loss associated with Alzheimer's disease, memory loss associated with Parkinson's disease, attention deficit symptoms, attention deficit symptoms associated with Alzheimer's disease, Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from β.sub.2 microglobulins and complications arising therefrom in hemodialysis patients), scrapie, bovine spongiform encephalitis, traumatic brain injury ("TBI"), and Creutzfeld-Jakob disease, comprising administering to said patient at least one triazolopyrimidine and/or triazolopyridine compound described herein, or a tautomer or isomer thereof; or pharmaceutically acceptable salt or solvate of said compound or said tautomer, in an amount effective to inhibit said pathology or pathologies.

In certain embodiments such additional therapeutic agents include, but are not limited to acetylcholinesterase inhibitors (including without limitation, e.g., (−)-phenserine enantiomer, tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil and ungeremine); NMDA receptor antagonist (including without limitations e.g., Memantine); muscarinic receptor agonists (including without limitation, e.g., Talsaclidine, AF-102B, AF-267B (NGX-267)); nicotinic receptor agonists (including without limitation, e.g., Ispronicline (AZD-3480)); beta-secretase inhibitors (including without limitations e.g., thiazolidinediones, including rosiglitazone and pioglitazone); gamma-secretase inhibitors (including without limitation, e.g., semagacestat (LY-450139), MK-0752, E-2012, BMS-708163, PF-3084014, begacestat (GSI-953), and NIC5-15); inhibitors of Aβ aggregation (including without limitation, e.g., Clioquinol (PBT1), PBT2, tramiprosate (homotaurine), Scyllo-inositol (a.k.a., scyllo-cyclohexanehexol, AZD-103 and ELND-005), passive immunotherapy with Aβ fragments (including without limitations e.g., Bapineuzemab) and Epigallocatechin-3-gallate (EGCg)); anti-inflammatory agents such as cyclooxygenase II inhibitors; anti-oxidants such as Vitamin E and ginkolides; immunological approaches, such as, for example, immunization with Aβ peptide or administration of anti-Aβ peptide antibodies; statins; and direct or indirect neurotrophic agents such as Cerebrolysin™, AIT-082 (Emilieu, 2000, Arch. Neurol. 57:454), Netrin (Luorenco (2009) Cell Death Differ., 16: 655-663), Netrin mimetics, NGF, NGF mimetics, BDNF and other neurotrophic agents of the future, agents that promote neurogenesis e.g. stem cell therapy. Further pharmacologic agents useful in the treatment or prevention diseases characterized by amyloid deposits in the brain, including MCI and/or AD, are described, e.g., in Mangialasche et al. (2010) Lancet Neurol., 9: 702-716.

In certain embodiments, additional non-limiting examples of additional therapeutic agents for use in combination with compounds described herein include: muscarinic antagonists (e.g., $m_i$ agonists (such as acetylcholine, oxotremorine, carbachol, or McNa343), or $m_2$ antagonists cholinesterase inhibitors (e.g., acetyl- and/or butyrylchlolinesterase inhibitors such as donepezil (Aricept®), galantamine (RAZADYNE®), and rivastigimine (EXELON®); N-methyl-D-aspartate receptor antagonists (e.g., NAMENDA® (memantine HCl); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB 1 receptor inverse agonists or CB 1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., REMBER®; RAGE inhibitors (e.g., TTP 488 (PF-4494700)); anti-Aβ vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, VYTORIN®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., SIMCOR® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., DIMEBON®, Pfizer).

Accordingly certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is disulfiram and/or analogues thereof (see, e.g., U.S. Ser. No. 13/213,960 (U.S. Patent Publication No: US-2012-0071468-A1), and PCT/US2011/048472 (PCT Publication No: WO 2012/024616) which are incorporated herein by references for the compounds described therein).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is honokiol and/or analogues thereof (see, e.g., U.S. Ser. No. 13/213,960 (U.S. Patent Publication No: US-2012-0071468-A1), and PCT/US2011/048472 (PCT Publication No: WO 2012/024616) which are incorporated herein by references for the compounds described therein).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is tropisetron and/or analogues thereof (see, e.g., U.S. Ser. No. 13/213,960 (U.S. Patent Publication No: US-2012-0071468-A1), and PCT/US2011/048472 (PCT Publication No: WO 2012/024616) which are incorporated herein by references for the compounds described therein).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is tropisetron.

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is nimetazepam and/or analogues thereof (see, e.g., U.S. Ser. No. 13/213,960 (U.S. Patent Publication No: US-2012-0071468-A1), and PCT/US2011/048472 (PCT Publication No: WO 2012/024616) which are incorporated herein by references for the compounds described therein).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is a tropinol ester or related ester (see, e.g., PCT/US2012/049223 (WO 2013/019901 A2), and U.S. Ser. No. 14/235,405 which are incorporated herein by reference for the tropinol esters and related compounds described therein).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is a TrkA kinase inhibitor (e.g., ADDN-1351) and/or analogues thereof (see, e.g., PCT/US2012/051426 (WO 2013/026021 A2), which is incorporated hereby reference for the TrkA kinase inhibitors and analogs thereof described therein.

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is a D2 receptor agonists and/or an alpha1-adrenergic receptor antagonists.

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is an ASBIs as described and/or claimed in PCT/US2013/032481 (WO 2013/142370 A1) and U.S. Ser. No. 14/384,641 which are incorporated herein by reference for the active agents described therein including, but not limited to galangin, a galangin prodrug, rutin, and other flavonoids as described or claimed therein.

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is one or more cholinesterase inhibitors (e.g., acetyl-and/or butyrylchlolinesterase inhibitors).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is one or more muscarinic antagonists (e.g., $m_1$ agonists or $m_2$ antagonists).

Certain embodiments provide a pharmaceutical composition comprising an effective amount of one or more triazolopyrimidine(s) and/or triazolopyridine(s) described herein and an additional therapeutic agent, and/or a method of treatment or prophylaxis comprising administration of one or more triazolopyrimidine(s) and/or triazolopyridine(s) described herein in conjunction with an additional therapeutic agent where the therapeutic agent in the formulation and/or method is one or more compounds selected from the group consisting of cholinesterase inhibitors (such as, for example, (.+−.)-2,3-dihydro-5,6-dimethoxy-2-[[1-(phenylmethyl)-4-piperidinyl]methy-1]-1H-inden-1-one hydrochloride, i.e, donepezil hydrochloride, available as the ARICEPT® brand of donepezil hydrochloride), N-methyl-D-aspartate receptor inhibitors (such as, for example, Namenda® (memantine HCl)); anti-amyloid antibodies (such as bapineuzumab, Wyeth/Elan), gamma secretase inhibitors, gamma secretase modulators, and beta secretase inhibitors other than the triazolopyrimidine(s) and/or triazolopyridine(s) described herein.

Methods of Monitoring Clinical Efficacy

In various embodiments, the effectiveness of treatment can be determined by comparing a baseline measure of a parameter of disease before administration of the agent(s) (e.g., triazolopyrimidine(s) and/or triazolopyridine(s) described herein, or a tautomer(s) or stereoisomer(s) thereof, or pharmaceutically acceptable salts or solvates of said triazolopyrimidine and/or triazolopyridine(s), said stereoisomer(s), or said tautomer(s), or analogues, derivatives, or prodrugs thereof) is commenced to the same parameter one or more time points after the agent(s) or analog has been administered. One illustrative parameter that can be measured is a biomarker (e.g., a peptide oligomer) of APP processing or related and implicated pathways. Such biomarkers include, but are not limited to sAPPα, p3 (Aβ17-42 or Aβ17-40), sAPPβ, soluble Aβ40, and/or soluble Aβ42 in the blood, plasma, serum, urine, mucous or cerebrospinal fluid (CSF).

An important indicator is p-tau and tau. A reduction of p-tau and/or tau is an indication of desirable efficacy. Additionally, inhibition in elevation of p-tau, e.g., stress-induced (cortisol-induced) p-tau is also an indication of efficacy.

Additionally, detection of increased levels of sAPPα and/or p3, and decreased levels of sAPPβ and/or APPneo is an indicator that the treatment is effective. Conversely, detection of decreased levels of sAPPα and/or p3, and/or increased levels of sAPPβ, APPneo, Tau or phospho-Tau (pTau) may be an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MRI. Administration of one or more of the agent(s)) described herein (e.g., triazolopyrimidine(s) and/or triazolopyridine(s), or a tautomer(s) or stereoisomer(s) thereof, or pharmaceutically acceptable salt, solvate, or clathrate said compound(s), said stereoisomer(s), or said tautomer(s), or analogues, derivatives, or prodrugs thereof) can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

Clinical efficacy can be monitored using any method known in the art. Measurable biomarkers to monitor efficacy include, but are not limited to, monitoring blood, plasma, serum, urine, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3, and decreased levels of sAPPβ and/or APPneo are indicators that the treatment or prevention regime is efficacious. Conversely, detection of decreased levels of sAPPα and/or p3, and increased levels of sAPPβ and/or APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including CT, PET, PIB-PET and/or MRI.

Efficacy can also be determined by measuring the cognitive abilities of the subject. Cognitive abilities can be measured using any method known in the art. Illustrative tests include assigning a Clinical Dementia Rating (CDR) score or applying the mini mental state examination (MMSE) (Folstein, et al. (1975) *J. Psychiatric Res.* 12(3): 189-198). Subjects who maintain the same score or who achieve an improved score, e.g., when applying the CDR or MMSE, indicate that the treatment or prevention regime is efficacious. Conversely, subjects who receive a score indicating diminished cognitive abilities, e.g., when applying the CDR or MMSE, indicate that the treatment or prevention regime has not been efficacious.

In certain embodiments, the monitoring methods can entail determining a baseline value of a measurable biomarker or parameter (e.g., amyloid plaque load or cognitive abilities) in a subject before administering a dosage of the agent(s), and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

In certain embodiments the tissue sample for analysis is typically blood, plasma, serum, urine, mucous or cerebrospinal fluid from the subject.

Kits.

In various embodiments, the active agent(s) (e.g., triazolopyrimidine(s) and/or triazolopyridine(s)) described herein thereof can be enclosed in multiple or single dose containers. The enclosed agent(s) can be provided in kits, for example, including component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments, a kit is provided where the kit comprises one or more triazolopyrimidine and/or triazolopyridine compounds described herein, or a tautomer or stereoisomer thereof, or pharmaceutically acceptable salt, solvate, or clathrate of said compound, said stereoisomer, or said tautomer, preferably provided as a pharmaceutical composition and in a suitable container or containers and/or with suitable packaging; optionally one or more additional active agents, which if present are preferably provided as a pharmaceutical composition and in a suitable container or containers and/or with suitable packaging; and optionally instructions for use, for example written instructions on how to administer the compound or compositions.

In another embodiment, a kit is provided that comprises a single container or multiple containers: (a) a pharmaceutically acceptable composition comprising one or more compounds described herein (e.g., compounds shown in FIG. 2, or illustrated or described in Table 5, or a tautomer or stereoisomer thereof, or pharmaceutically acceptable salt, solvate, or clathrate of said compound, said stereoisomer, or said tautomer, optionally a pharmaceutically acceptable composition comprising one or more additional therapeutic agents; and optionally instructions for use their use. The kit may optionally comprise labeling (e.g., instructional materials) appropriate to the intended use or uses.

As with any pharmaceutical product, the packaging material(s) and/or container(s) are designed to protect the stability of the product during storage and shipment. In addition, the kits can include instructions for use or other informational material that can advise the user such as, for example, a physician, technician or patient, regarding how to properly administer the composition(s) as prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign protein is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the kits can comprise one or more packaging materials such as, for example, a box, bottle, tube, vial, container, sprayer, insufflator, intravenous (I.V.) bag, envelope, and the like; and at least one unit dosage form of an agent comprising active agent(s) described herein and a packaging material. In some embodiments, the kits also include instructions for using the composition as prophylactic, therapeutic, or ameliorative treatment for the disease of concern.

In some embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising one or more triazolopyrimidine(s) and/or triazolopyridines described herein, or a tautomer(s) or stereoisomer(s) thereof, or pharmaceutically acceptable salts, solvates, or clathrates of said triazolopyrimidine(s) and/or triazolopyridine(s), said stereoisomer(s), or said tautomer(s), or analogues, derivatives, or prodrugs thereof within the packaging material, along with a second composition comprising a second agent such as, for example, an agent used in the treatment and/or prophylaxis of Alzheimer's disease (e.g., as described herein), or any prodrugs, co-drugs, metabolites, analogs, homologues, congeners, derivatives, salts and combinations thereof. In some embodiments, the articles of manufacture may also include instructions for using the composition as a prophylactic, therapeutic, or ameliorative treatment for the disease of concern.

EXAMPLES

The following examples are offered to illustrate, but not to limit the claimed invention.

Example 1

Synthesis of J19

An illustrative, but non-limiting synthesis scheme for J19 is shown in FIG. 3. Reagents and conditions for synthesis Scheme 1 were: (a) 2-methoxyethanol, 125° C.; (b) $NaNO_2$, DCM, acetic acid, r.t; (c) THF, 100° C., sealed tube.

6-Chloro-N4-(4-chloro-2-methylphenyl)-2-methyl-pyrimidine-4,5-diamine (3)

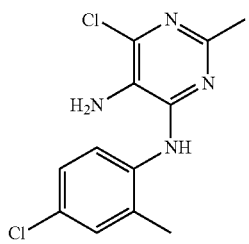 [SMILES: Cc1nc(Cl)c(N)c(Nc2ccc(Cl)cc2C)n1]

A 250 mL round bottom flask equipped with a reflux condenser was charged with a mixture of 4,6-dichloro-2-methylpyrimidin-5-amine (2.170 g, 12.2 mmol, 1.0 equiv.), 4-chloro-2-methylaniline (1.726 g, 12.2 mmol, 1.0 equiv.) and 2-methoxyethanol (100 mL) and the mixture was heated to an oil bath temperature of 125° C. with stirring under nitrogen. After 48 hours, TLC (1:1 ethyl acetate:hexane) indicated completion of the reaction. The mixture was concentrated under reduced pressure to leave a viscous oil. This was dissolved in ethyl acetate (approximately 30 mL) and the desired product precipitated upon the addition of hexane with stirring (approximately 100 mL). The mixture was allowed to sit at 4° C. overnight and the solid was collected by filtration, washed with hexane and dried under vacuum to give the product as a tan solid (2.4 g, 69%). $^1H$ NMR ($CDCl_3$. 300 MHz):δ 7.81 (d, J=9.3 Hz, 1H), 7.21-7.19 (m, 2H), 6.79 (bs, 1H), 3.29 (bs, 2H), 2.49 (s, 3H), 2.29 (s, 3H). LC/MS: 283.3 (M+1).

7-Chloro-3-(4-chloro-2-methylphenyl)-5-methyl-3H-[1,2,3]triazolo[4,5-d]pyrimidine

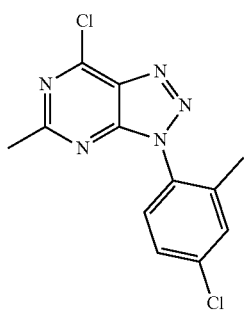

Sodium nitrite (0.289 g, 4.2 mmol, 1.1 equiv.) was added to a vigorously stirring mixture of 6-chloro-N4-(4-chloro-2-methylphenyl)-2-methylpyrimidine-4,5-diamine (1.060 g, 3.7 mmol, 1.0 equiv.) in dichloromethane (15 mL) and acetic acid (15 mL) at room temperature. After 45 minutes, TLC indicated complete disappearance of the starting material (1:3 ethyl acetate:hexane). The mixture was transferred to a separatory funnel and 50 mL of water was added. The dichloromethane layer was removed and washed with water, brine and dried over magnesium sulfate. The organic layer was then concentrated to dryness to leave a tan solid which was used directly without further purification (1.10 g, 100%). 1H NMR (CDCl3, 300 MHz): 7.46-7.35 (m, 3H), 2.85 (s, 3H), 2.19 (s, 3H). LC/MS: 294.2 $(M)^+$ 3-(4-Chloro-2-methylphenyl)-N-(1-methoxybutan-2-yl)-5-methyl-3H-[1,2,3]triazolo[4,5-d]pyrimidin-7-amine (6)

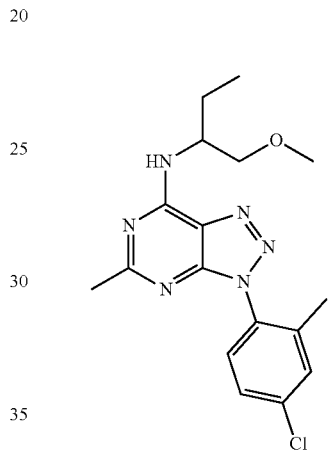

A mixture of 7-chloro-3-(4-chloro-2-methylphenyl)-5-methyl-3H-[1,2,3]triazolo[4,5-d]pyrimidine (1.0 g, 3.4 mmol, 1.0 equiv.) and 1-methoxybutan-2-amine (0.89 g, 8.9 mmol, 2.5 equiv.) in THF (15 mL) was heated in a sealed reaction vessel to an oil bath temperature of 100° C. with stirring. After 3 hours, TLC (20% ethyl acetate in hexanes) indicated complete disappearance of starting material and formation of a single product. The mixture was allowed to cool to room temperature. The mixture was concentrated to dryness and purified by flash chromatography over silica gel (0 to 100% ethyl acetate/hexane gradient) to give the title product as a white solid after drying. (0.47 g, 60.8%). $^1H$ NMR (CD3OD, 300 MHz): δ7.54-7.53 (m, 1H), 7.46-7.38 (m, 2H), 4.69-4.59 (m, 1H), 3.63-3.50 (m, 2H), 3.40 (s, 3H), 2.49 (s, 3H), 2.12 (s, 3H), 1.90-1.62 (m, 2H), 1.02 (t, 7.5 Hz, 3H). $^{13}C$-NMR (75 MHz, CD3OD) δ 9.89, 16.87, 24.45, 24.99, 25.09, 51.60, 55.06, 58.17, 74.04, 74.53, 126.96, 128.98, 131.00, 132.83, 135.97, 137.80, 150.12, 155.01, 168.03. LC-MS (m/z): 360 [M]+, 362 [M+2]+

Example 2

Evaluation of J03 and Analogs

As described below, in vitro studies were performed using SHSY-5Y cells. These cells are a useful neurological model that differentiate into cells with morphological and biochemical characteristics of mature neurons including mature isoforms of tau.

Animal experiments were performed using J20 mice. The J20 mouse is a model of for Alzheimer's disease. This model overexpresses human APP with two mutations linked to familial Alzheimer's disease (the APP KM670/671NL (Swedish) and 5APP V717F (Indiana) mutations).

Initial J03 Studies.

As shown in FIG. 4, panels A-C, J03 reduces tau and phospho-tau (p-tau) increases induced by CRF. In an initial study, SHSY-5Y cells were cultured without serum to induce differentiation and increase tau expression. CRF was added to the cultures at increasing concentrations and, as shown in FIG. 4, panels B and C, both tau (panel B) and phospho-tau (panel C) increased with CRF in a dose-dependent manner. The increases were proportional and both were about 50%. J03 (FIG. 4A) reduced the CRF-induced tau increases more than the p-tau increases. The increase in p-tau with CRF was expected, but the increase in tau less predictable as CRF reduces neuronal differentiation (see Chen et al. (2004) *Proc. Natl. Acad. Sci. USA,* 101(44): 15782-15787), however, it can increase tau accumulation.

Figure 5:
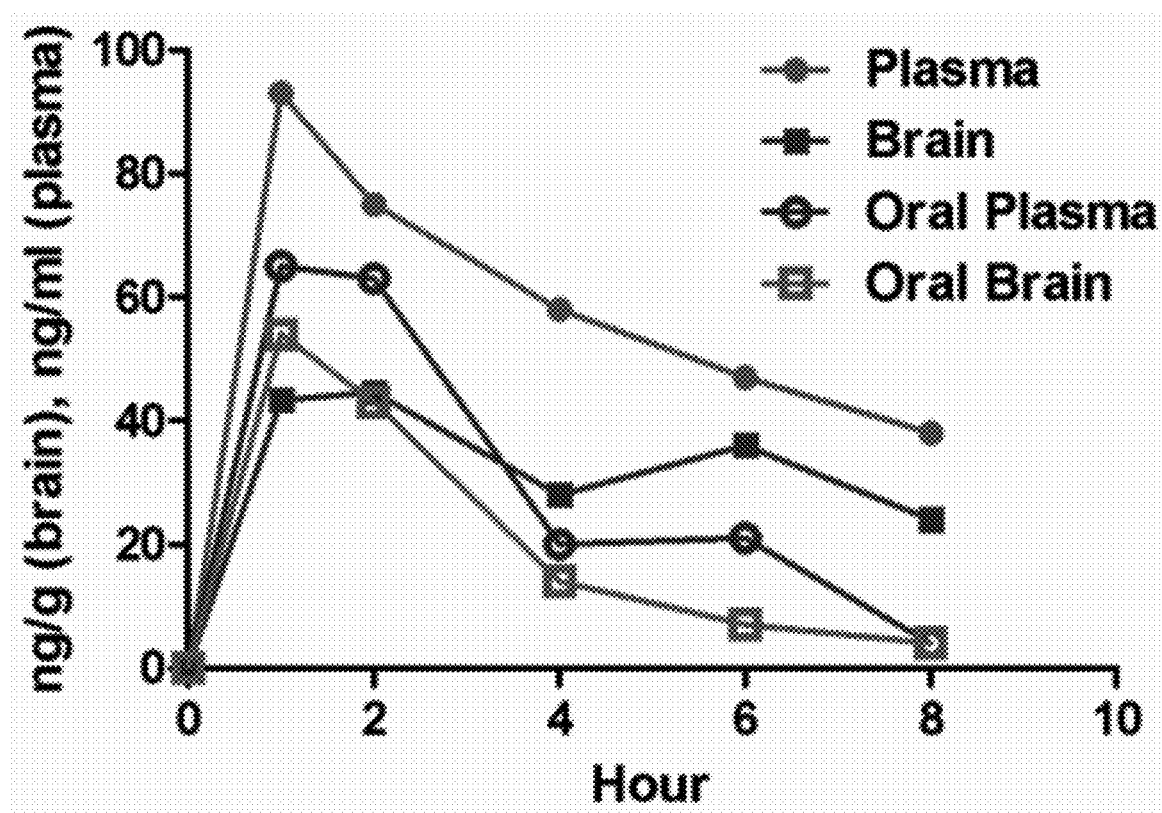
FIG. 5 Illustrates in vivo pharmacokinetics of J03 (10 mk delivered in a single 5 mg/ml DMSO stock, 60 μl, subcutaneous injection).

A standard pharmacokinetic study of J03 was performed in which J03 (10 mk delivered in a 5 mg/ml DMSO stock, 50 ml) was injected subcutaneously (SQ) into J20 mice. As shown in FIG. 5, J03 brain levels were low and the brain/plasma ratio was 1:2, but levels stayed up for hours, resulting in good exposure of brain tissue, even from a single injection. After oral delivery by feeding (not gavage) also at 10 mg/kg, brain levels were slightly higher at the peak (open grey box), and the brain:plasma ratio was close to 1:1.

Figure 6:
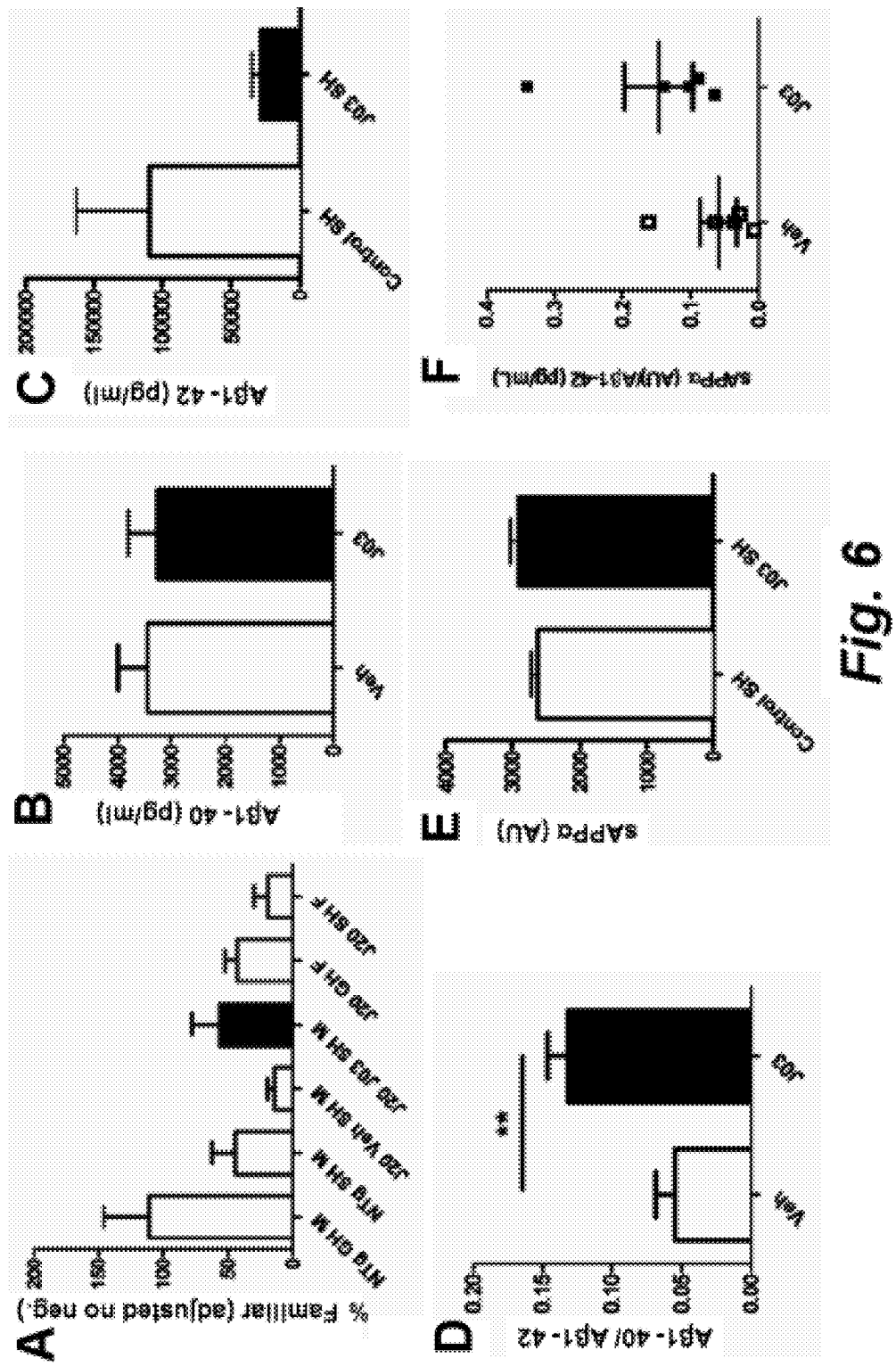
FIG. 6, panels A-F, illustrate non-tau data resulting from initial J03 study. Panel A: Familiarity; Panel B: Aβ1-40; Panel C: Aβ1-42; Panel D: Aβ1-40/Aβ1-42; Panel E: sAPPα levels; Panel F: sAPPα/Aβ1-42.

In pilot study #1, J20 mice housed singly were treated by SQ injection of J02 in PEG/b-MCD at 10 mkd for 12 days. NOR analysis of object memory (N=5/group) was performed. The results are illustrated in FIG. 6, panels A-F. As shown there was a slight improvement in behavior in single housed J03-treated J20 mice (panel A). There was no difference in Aβ1-40 (panel B), but a decrease in Aβ1-42 (panel C). The Aβ1-40/1-42 ratio was significantly increased (panel D). SAPP was very slightly increased (panel E), as was the sAPP/Aβ1-42 ratio (panel F).

Figure 7:
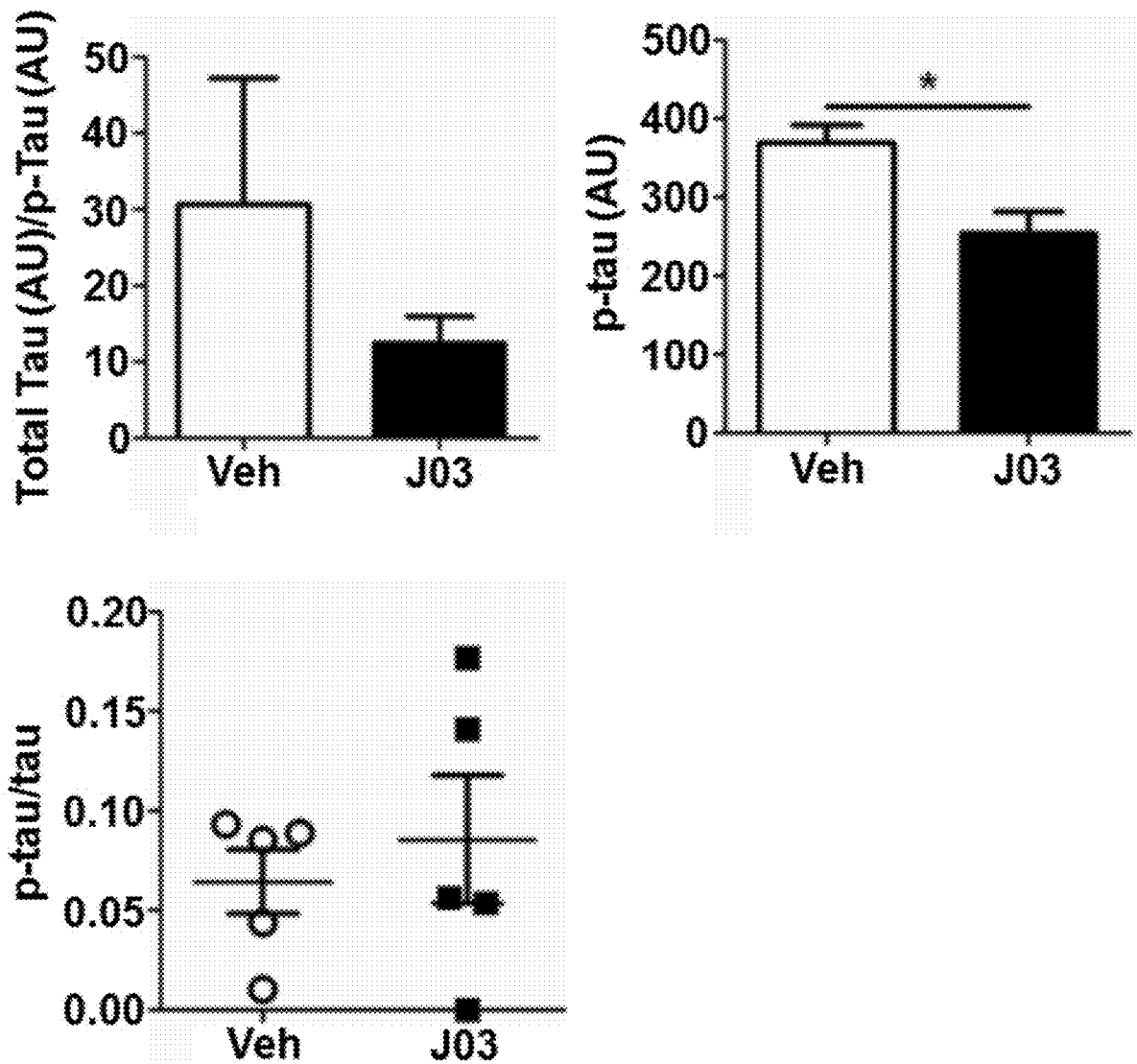
FIG. 7, illustrates effect of J03 on tau (top left), p-tau (top right), and the ratio p-tau/tau (bottom left).

Total tau was decreased by J03 (FIG. 7, top left panel), but largely due to one mouse. P-tau was significantly lower (FIG. 7, top right panel), and the ratio was slightly higher, but with great individual variation (FIG. 7, bottom panel).

Based on these promising results, the study was repeated (pilot study #2) with oral delivery and a longer duration.

Figure 8:
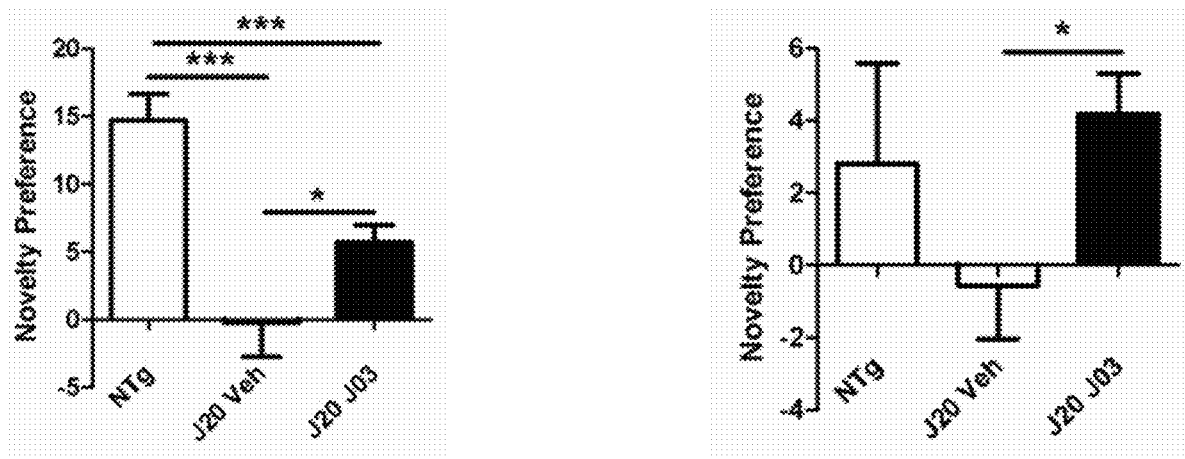
FIG. 8 illustrates the performance of J03-treated mice in both novel location (left) and object (right) assays.

As illustrated in FIG. 8, J03 treated mice performed well in both novel location (left) and novel object (right) assays.

Figure 9:
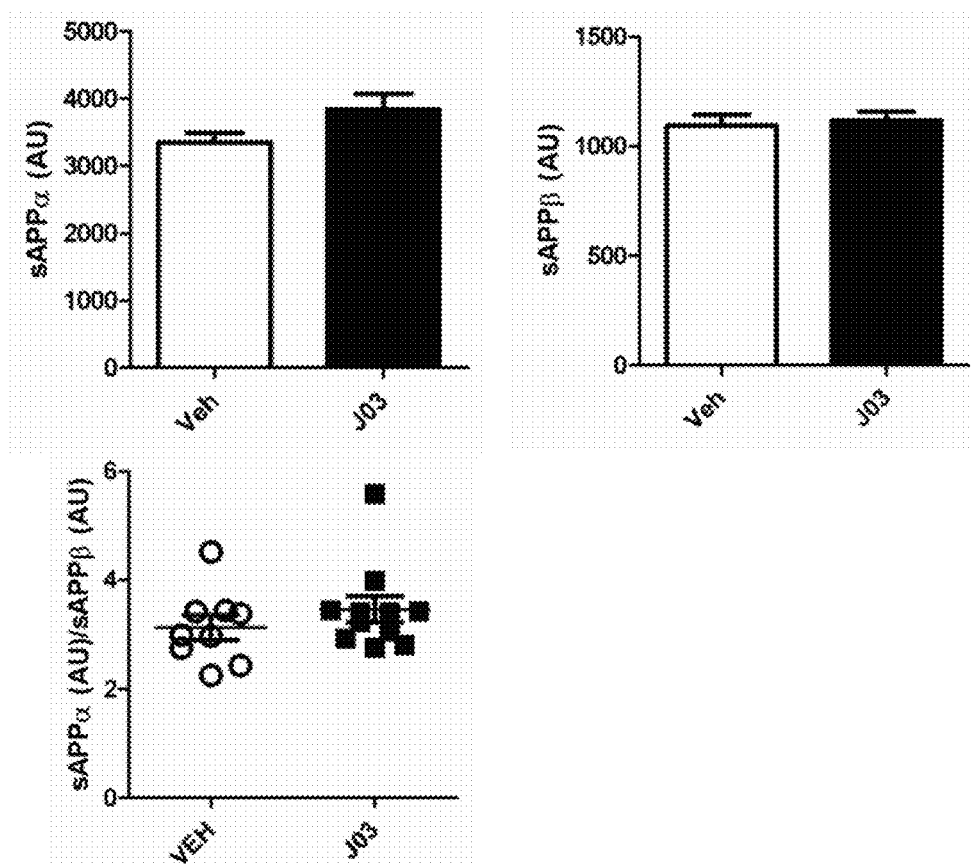
FIG. 9 illustrates the effect of J03 on sAPPα (top left), sAPPβ (top right), and the sAPPα/sAPPβ ratio (bottom left).
Figure 10:
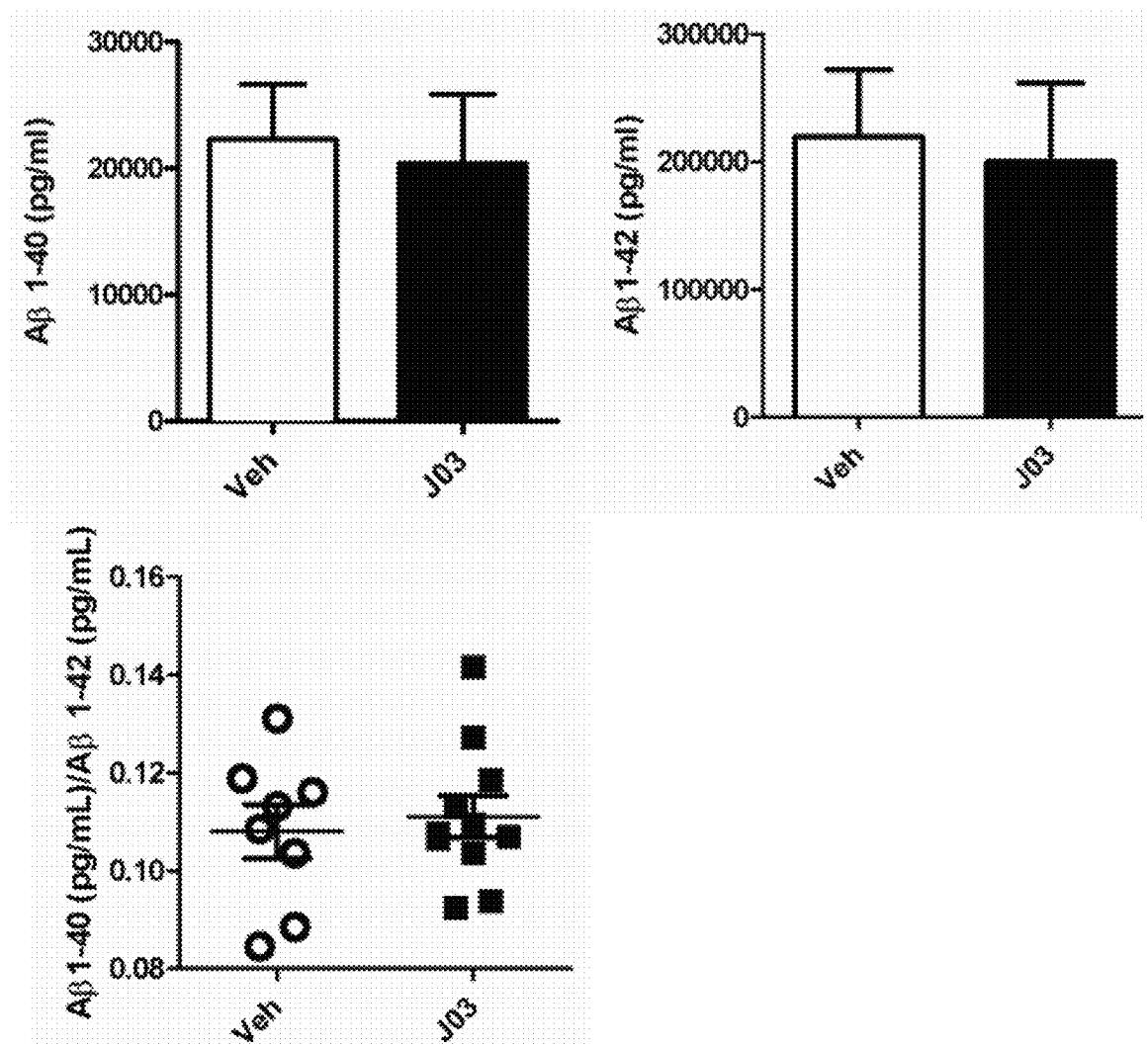
FIG. 10 illustrates the effect of J03 on Aβ1-40 (top left), Aβ1-42 (top right), and the Aβ1-40/Aβ1-42 ratio (bottom left).

As shown in FIG. 9, sAPPα increased slightly (top left), sAPPβ was unchanged (top right), and the sAPPα/sAPPβ ratio (bottom panel) was slightly increased. Both Aβ1-40 (FIG. 10, top left) and Aβ1-42 (FIG. 10, top right) were unchanged with no significant trend to increase. The Aβ1-40/Aβ1-42 ratio (FIG. 10, bottom) was unchanged.

Figure 11:
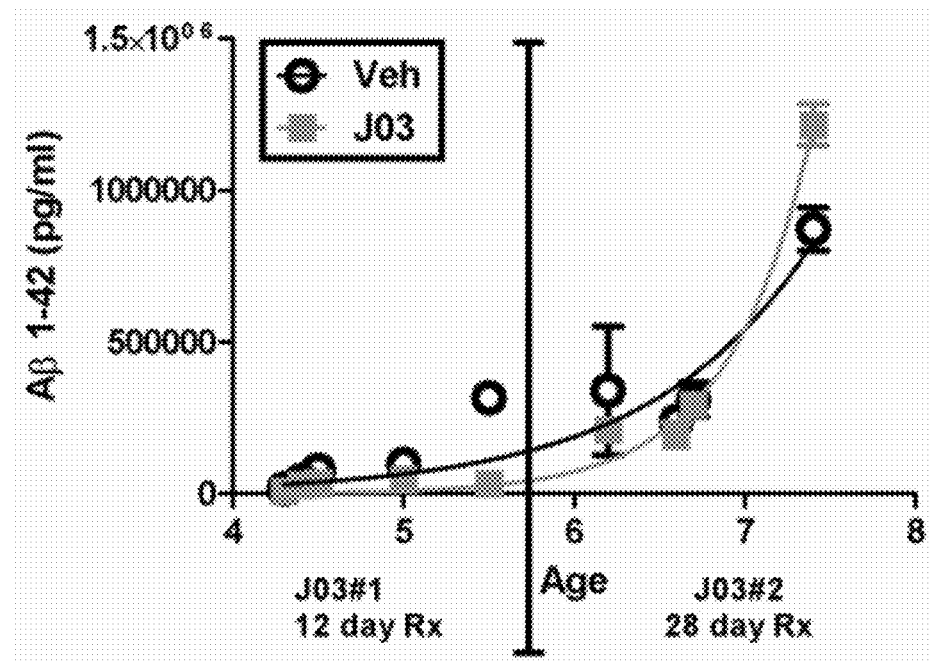
FIG. 11 illustrates the effect of J03 on Aβ1-42 in two studies.

FIG. 11 illustrates the effects of J03 on Aβ1-42 in pilot studies #1 and #2. All mice in the pilot study #2 were older than the mice used in J03 pilot study #1. This was deliberate (as was the choice of younger mice in the first study) as it appeared in the first study the greatest difference in Aβ1-42 was in the oldest J03-treated mouse. When the results are graphed together (with adjustment for dilution factor in the assay), the oldest vehicle-treated mouse in J03 pilot study #1 appears to be a slightly high outlier. Nonetheless, the curves here suggest there is some Aβ-decreasing effect if treatment is started in younger mice, but it is lost if treatment is started after Aβ amplification is underway, as it was in the oldest mice in J03 pilot study #2.

Figure 12:
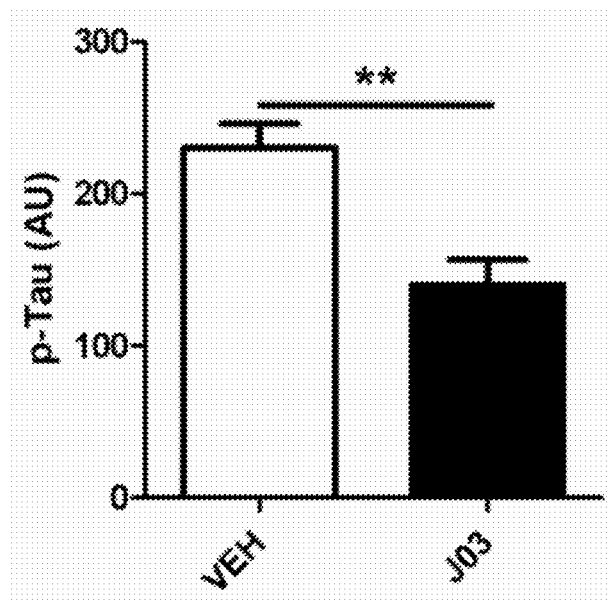
FIG. 12 illustrates the effect of J03 on phosphorylated tau (p-tau).

FIG. 12 shows the effect of J03 on p-tau in pilot study #2. Not only was p-tau decreased again here as it was in pilot study #1, the decrease reached statistical significance.

Figure 13:
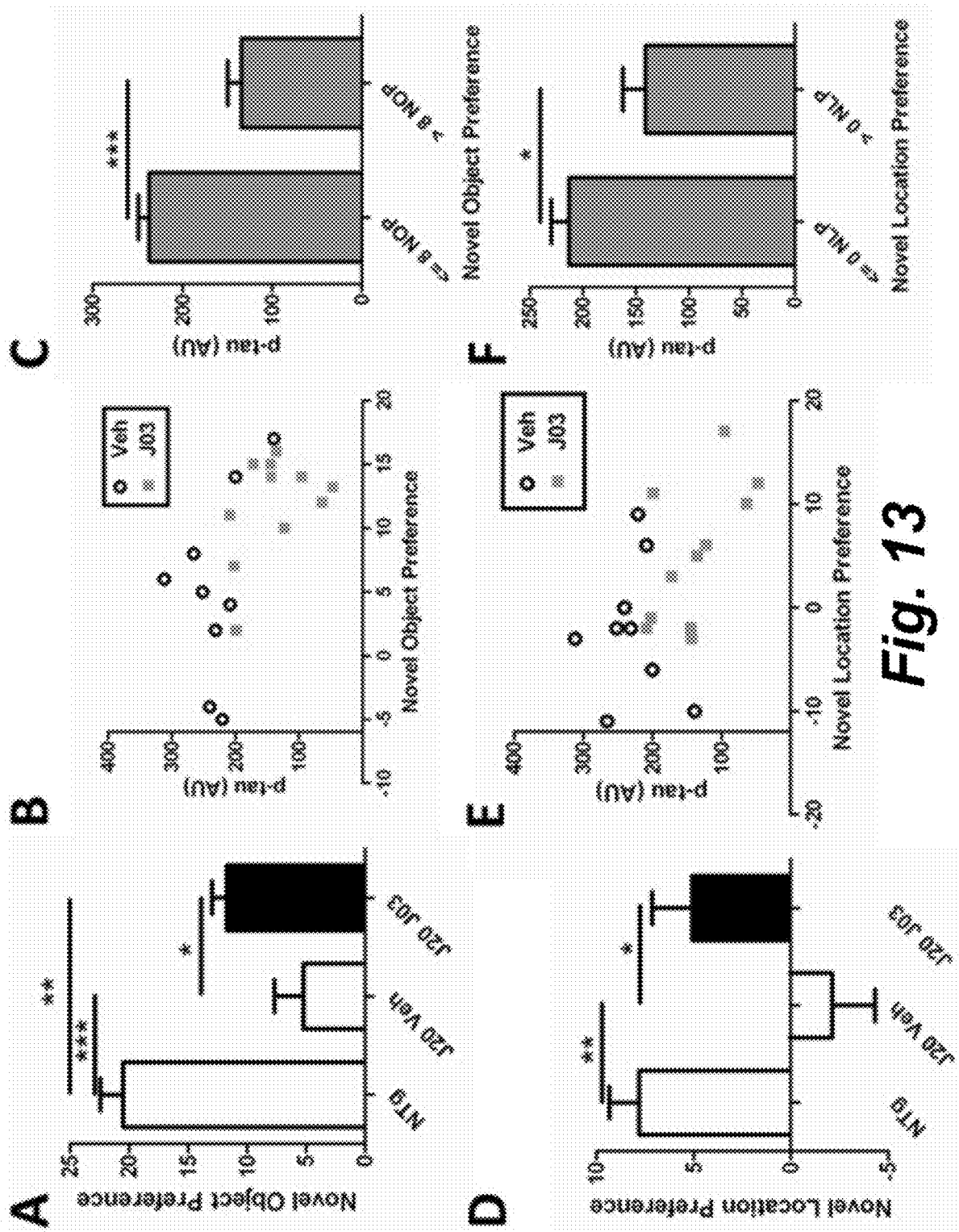
FIG. 13, panels A-F, illustrates the effect of J03 on p-tau and memory. Panel A: Novel object preference; Panel B: p-tau versus novel object preference; Panel C: Relationship between novel object preference (NOP) score and p-tau; Panel D: Effect of J03 on novel location preference (NLP); Panel E p-tau versus novel location preference; Panel F: Relationship between novel location preference (NLP) score and p-tau.
Figure 14:
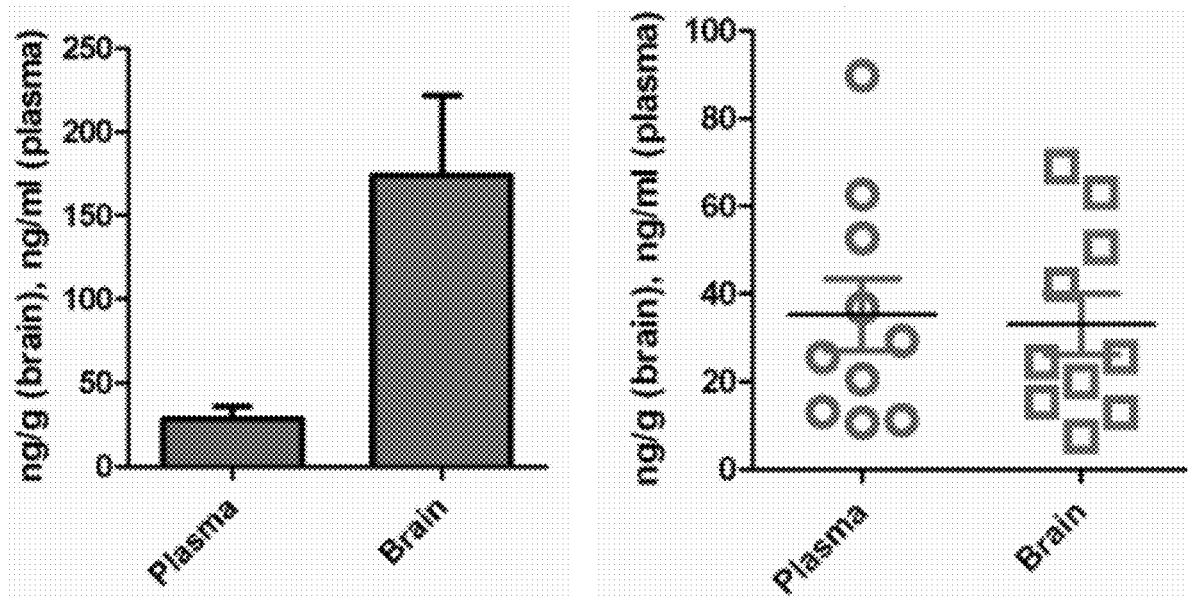
FIG. 14 illustrates plasma and brain levels of J03 two hours after oral dosing (left panel) and at the end of the study (right panel).

FIG. 13, panels A-F, shows the effect of J03 on p-tau and memory. Even vehicle-treated J20 mice showed some novel object preference in the modified protocol, with the erro bar extended to 8 (panel A). There was good correlation to p-tau levels (panel B). Mice that scored above 8 had significantly lower p-tau levels (panel C). Novel location preference was even clearer for J03-treated J20 mice (panel D), and also showed good correlation to p-tau levels (panel E), and mice that scored over 0, therefore showing some novel location preference, had significantly lower p-tau (panel F).

To obtain an early look at plasma and brain J03 levels after oral dosing in formulation, two additional mice were dosed on the first day of the study and euthanized two hours later. In these mice brain levels were higher than expected, at 170 ng/g, (FIG. 9, left panel) but with great variation between the two mice. At the end of the study brain levels were in the expected range of about 35 ng/g (FIG. 9, right panel), again with great variation.

J04 Studies.

J04 (see, FIG. 2) was designed as an analog with replacement of the triazolopyridine with the triazolopyrimidine ring.

Figure 15:
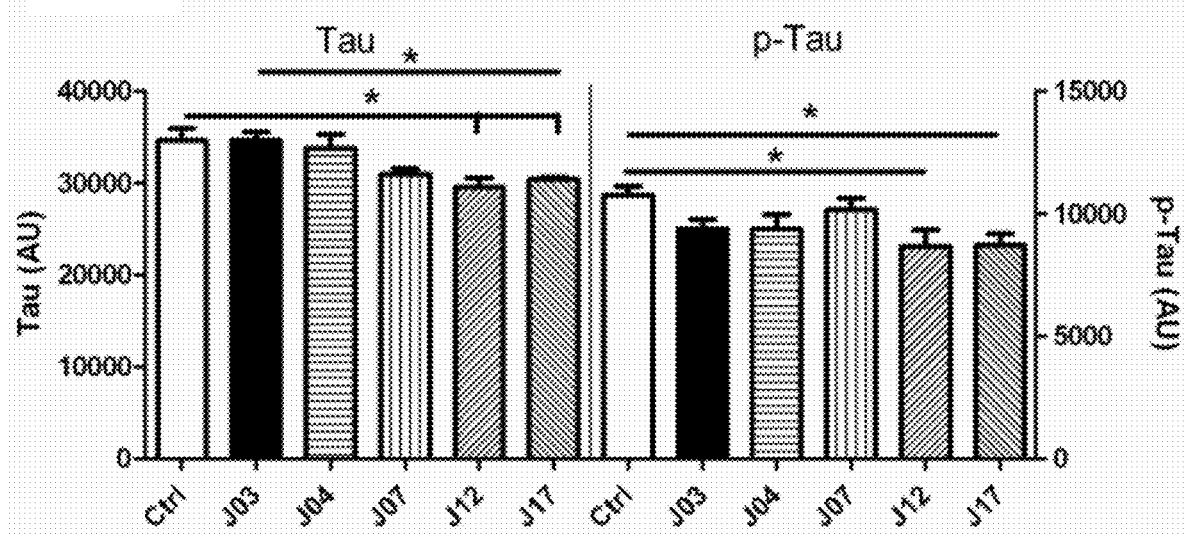
FIG. 15 illustrates the effect of J03, J04, J07, and J12 on tau and p-tau.

In a primary screen in SH-Sy5Y cells, J04 did not lower tau in the primary screen, but did lower p-tau, although not significantly (see, FIG. 15). However, J04 did lower p-tau to the same level as J03 and significant may not have been reached due to low N #.

Figure 16:
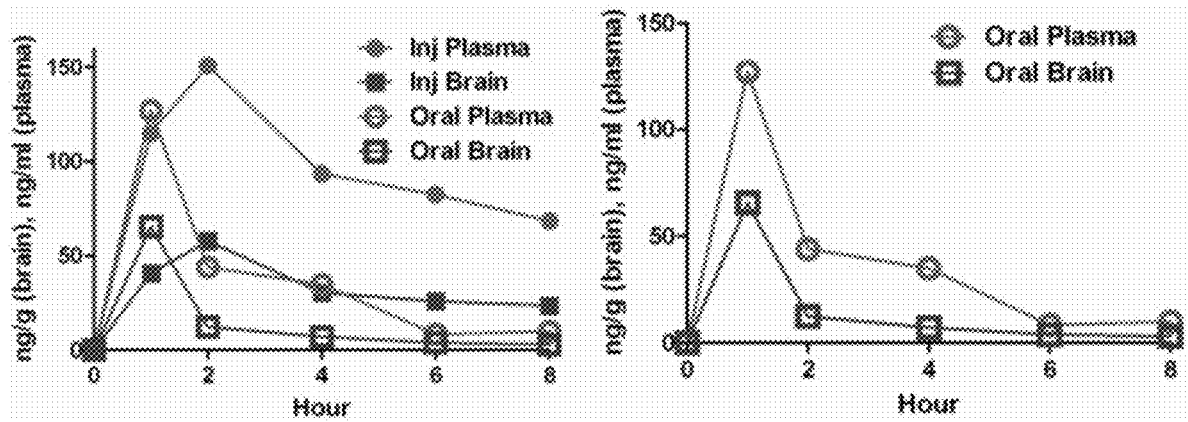
FIG. 16 illustrates the pharmacokinetics of J04 in brain and plasma after injection and oral delivery (left panel) or after oral delivery (right panel).

Brain levels after SQ injection or oral delivery (FIG. 16, left) were similar at ~55 ng/g, although clearance after injection was slower. Clearance after oral delivery is shown in FIG. 16, right.

J17 studies.

Figure 17:
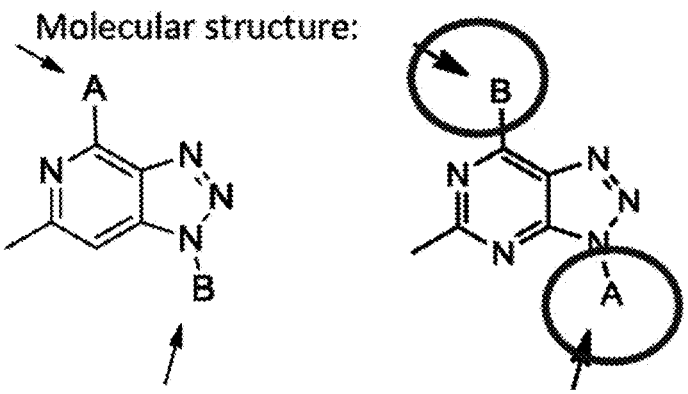
FIG. 17 schematically illustrates the reversal of substituents around the triazolopyrimidine ring. With respect to any of the compounds described herein the reversed substituent form is contemplated as well.

In compound J17 (see FIG. 2), two substituents (see circled substituents in FIG. 17) were reversed.

Figure 18:
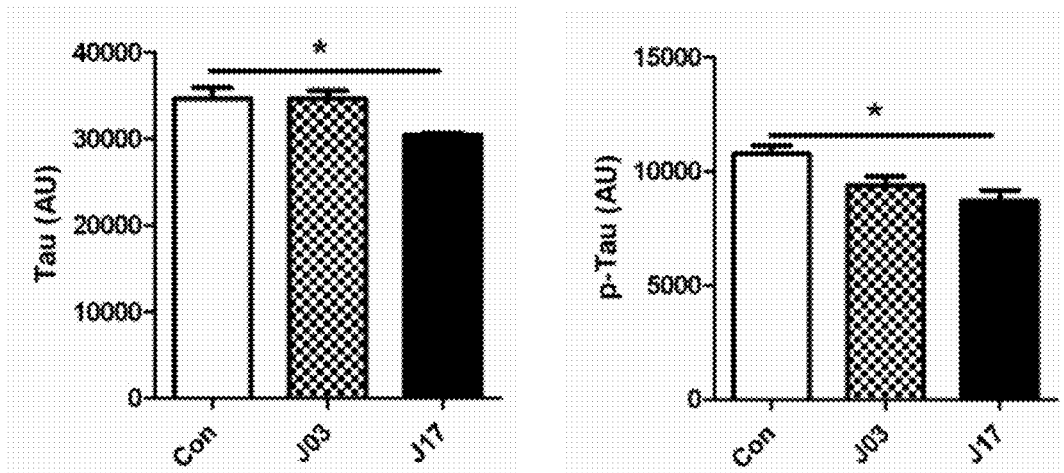
FIG. 18 illustrates the effect of J17 on tau (left panel) and p-tau (right panel) in SH-SY5Y cells.

J17 was observed to significantly lower tau (FIG. 18, left), and p-tau (FIG. 18, right) in SH-Sy5Y cells and the effect was greater than that measured for J03.

Figure 19:
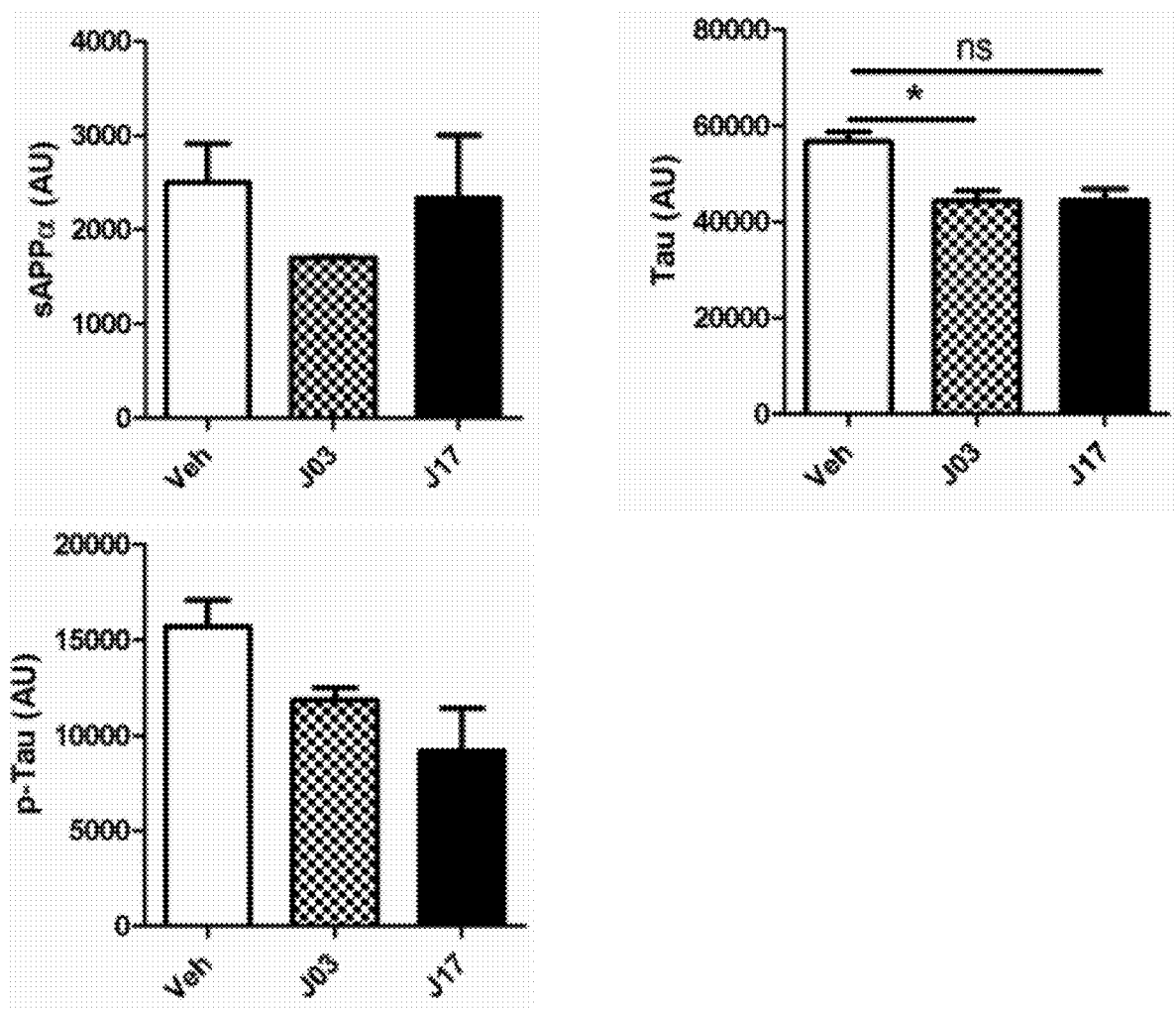
FIG. 19 illustrates the effect of J17 on sAPPα (top left), tau (top right), and p-tau (bottom left) after CRF stimulation.

As shown in FIG. 19, after exposure to CRF, sAPPα (top left) was the same as control for J17, but lower for J03 in this experiment. Tau was decreased for both J03 and J17 (top right). While the J17 decrease looks the same as J03, the value for J17 just missed significance. P-tau was decreased for both J03 and J17 (bottom left). The N number of 3 limited the ability to reach statistical significance.

Figure 20:
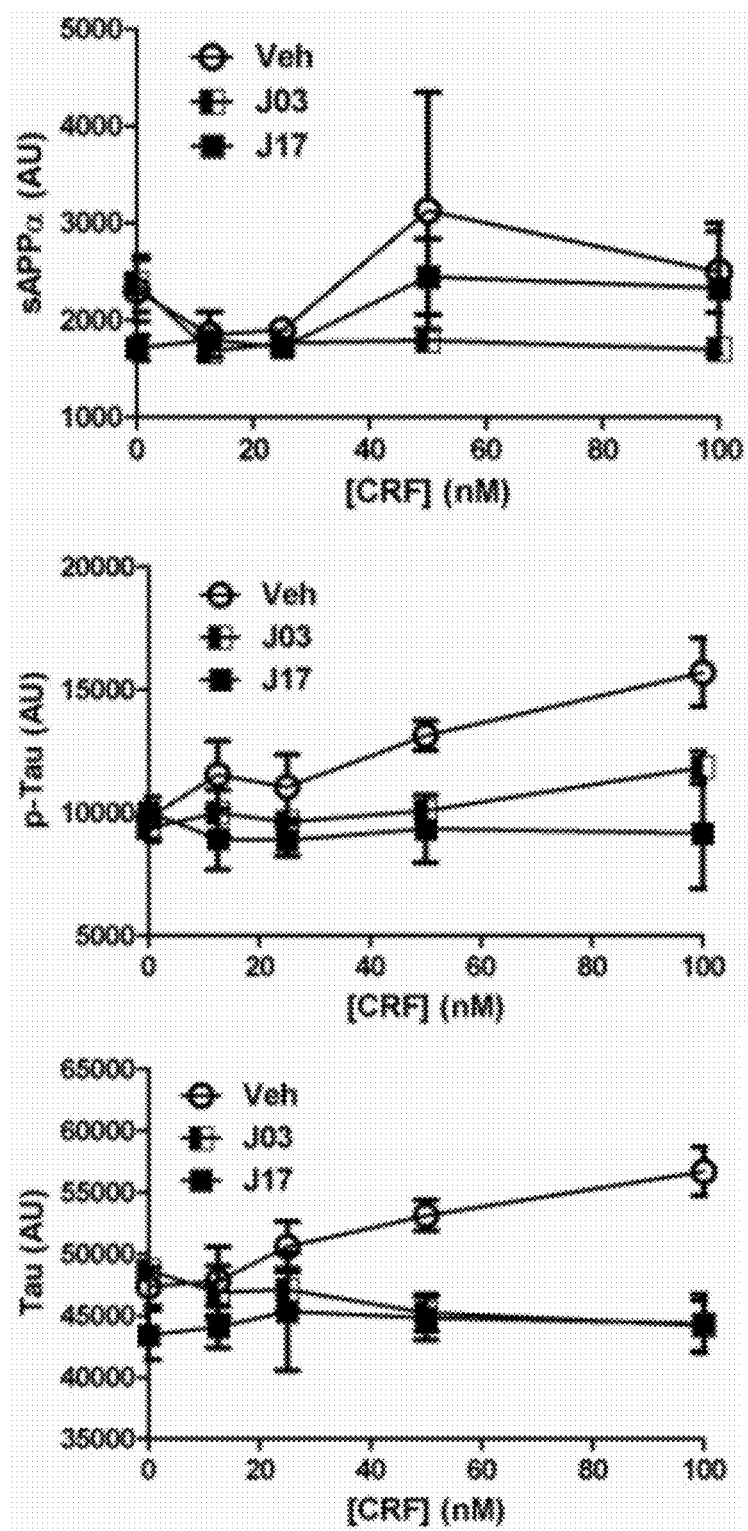
FIG. 20 illustrates the effect J03 and J17 on sAppα (top left), tau (top right), and p-tau (bottom left) with increasing concentrations of CRF.

FIG. 20 illustrates the effect of J03 and J17 on sAPPα, tau, and p-tau with increasing concentrations of CRF. The decrease in sAPPα with J17, or rather, a lack of increase, was seen without CRF and at 50 nM (top left), but not at other concentrations. The decrease in tau was seen without CRF and at 50 and 100 nM (top middle). The decrease in p-tau was seen at all concentrations of CRF tested, excluding 0 (bottom left).

Figure 21:
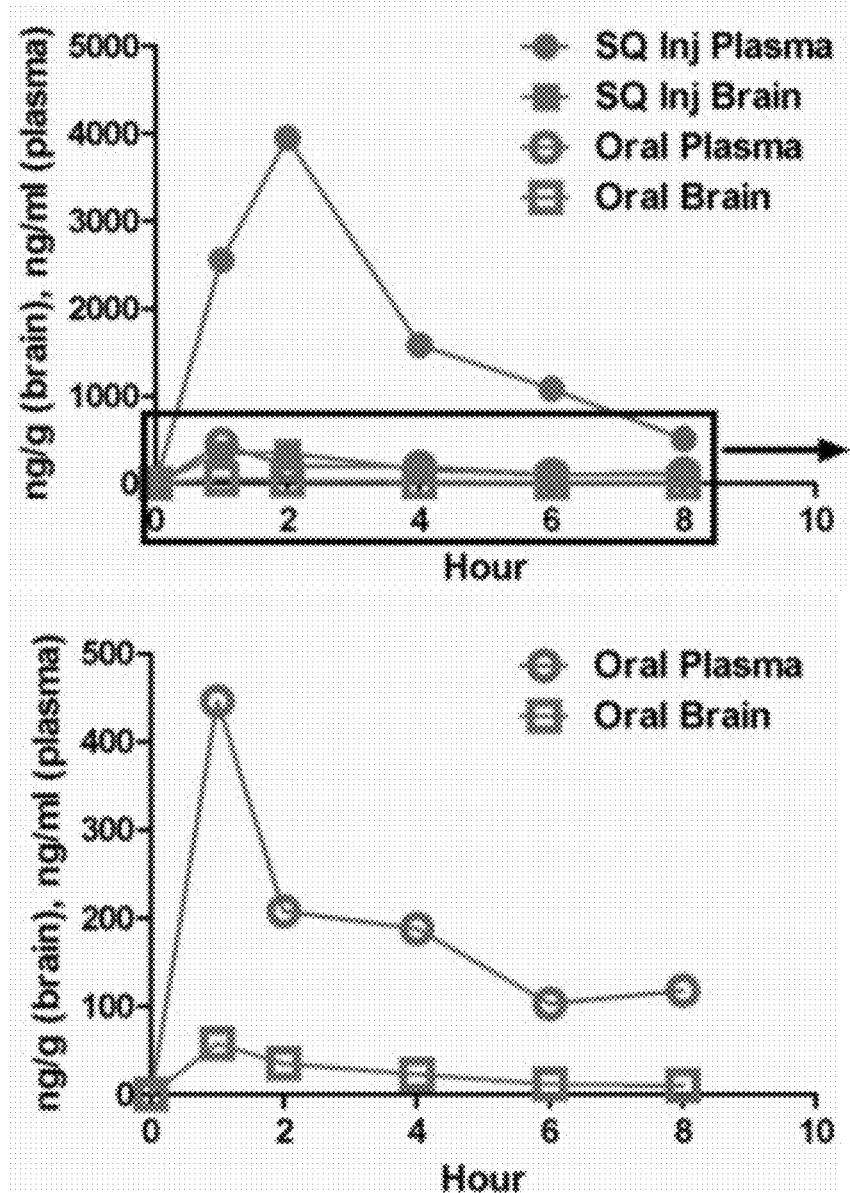
FIG. 21 illustrates in vivo pharmacokinetics of J17.

FIG. 21 illustrates in vivo pharmacokinetics of J17. After subcutaneous injection (SQ Inj) of 10 mg/kg, brain levels were low (~400 ng/g) relative to plasma levels (~4000 ng/m) (left). After oral delivery at the same dose, brain levels were only ~50 ng/g and plasma levels were once again almost 10-fold higher.

In a J17 pilot study (#1 pilot study) male and female J20 mice were housed singly and treated with J17 at 10 mkd by oral delivery for 28 days. Male and female J20 mice were housed singly and treated with J17 at 10 mkd by oral delivery for 28 days.

Figure 22:
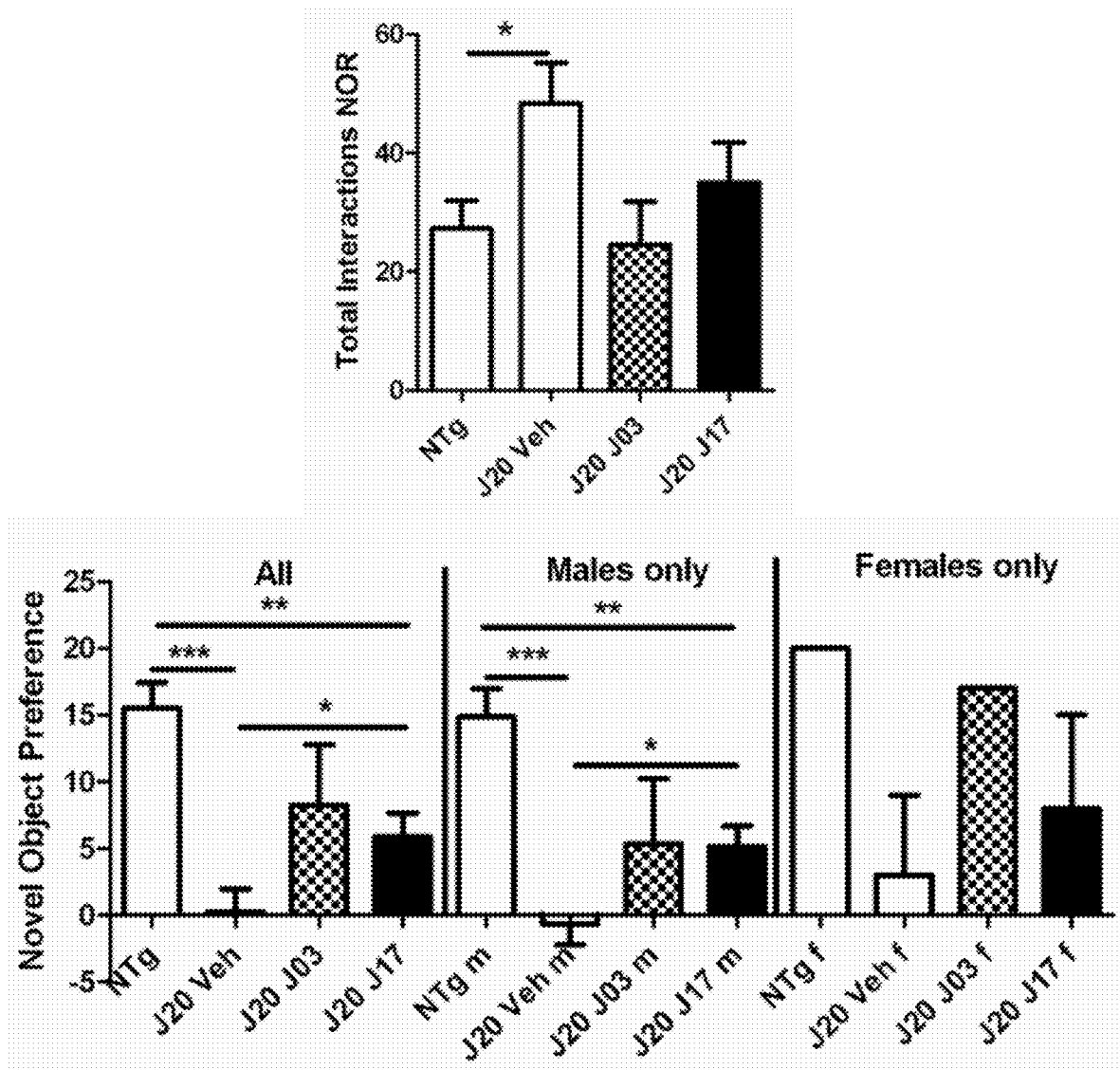
FIG. 22 illustrates the effect of J03 and J17 on total interactions and novel object preference.

The results for males and females showed some differences and are presented together and separately in FIG. 22. As shown therein, both J03 and J17 lowered activity, but not significantly due to individual variation (top panel). Overall, J03 increased novel object preference more than 17, but only the increase with J17 was significant as there was less variation (bottom left). Males (n=6 per group) showed a pattern similar to all the mice (bottom middle panel), with the improvement in memory being less and more similar between J03 and J17. While the greatest increase in NOP was in a female with J03 (bottom right panel), it was only one female (there was also only one female in the NTg group). There were only two females in the J03 and J17 groups.

Figure 23:
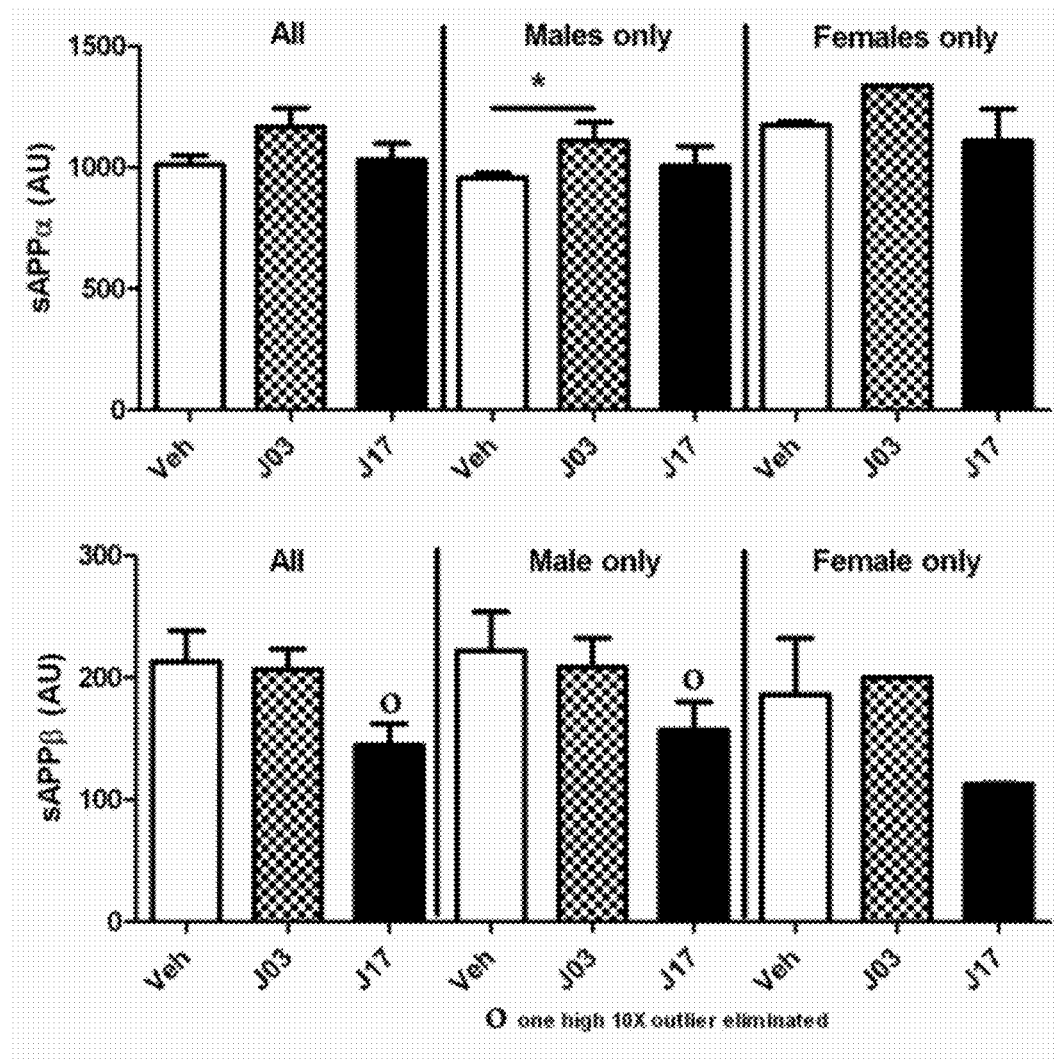
FIG. 23 illustrates the effect of J03 and J17 on sAPPα (top panel), sAPPβ (middle panel) and the ratio (bottom panel) broken out by gender.
Figure 23:
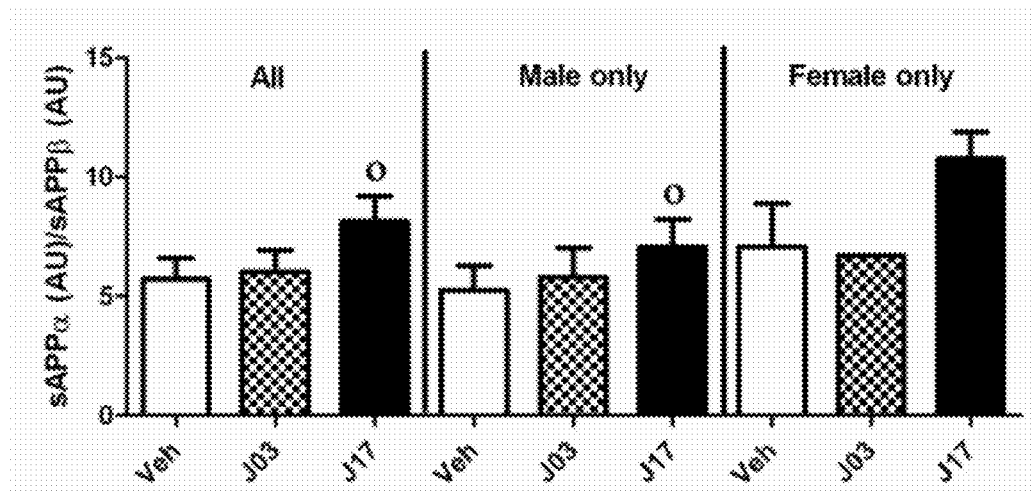

FIG. 23 shows the effect of J03 and J17 on sAPPα, sAPPβ, and the ratio sAPPα/sAPPβ. The sAPPα results were similar for both genders and showed an increase with J03 but not J17 (top panel). sAPPβ results were also similar. There was an decrease with J17 only (one high outlier that was eliminated from the data) (middle panel). There was only a slight increase in the ratio for males with J03, and it was greater with J17, but the two females showed an even greater increase in the ratio, but without statistical significance (bottom panel).

Figure 24:
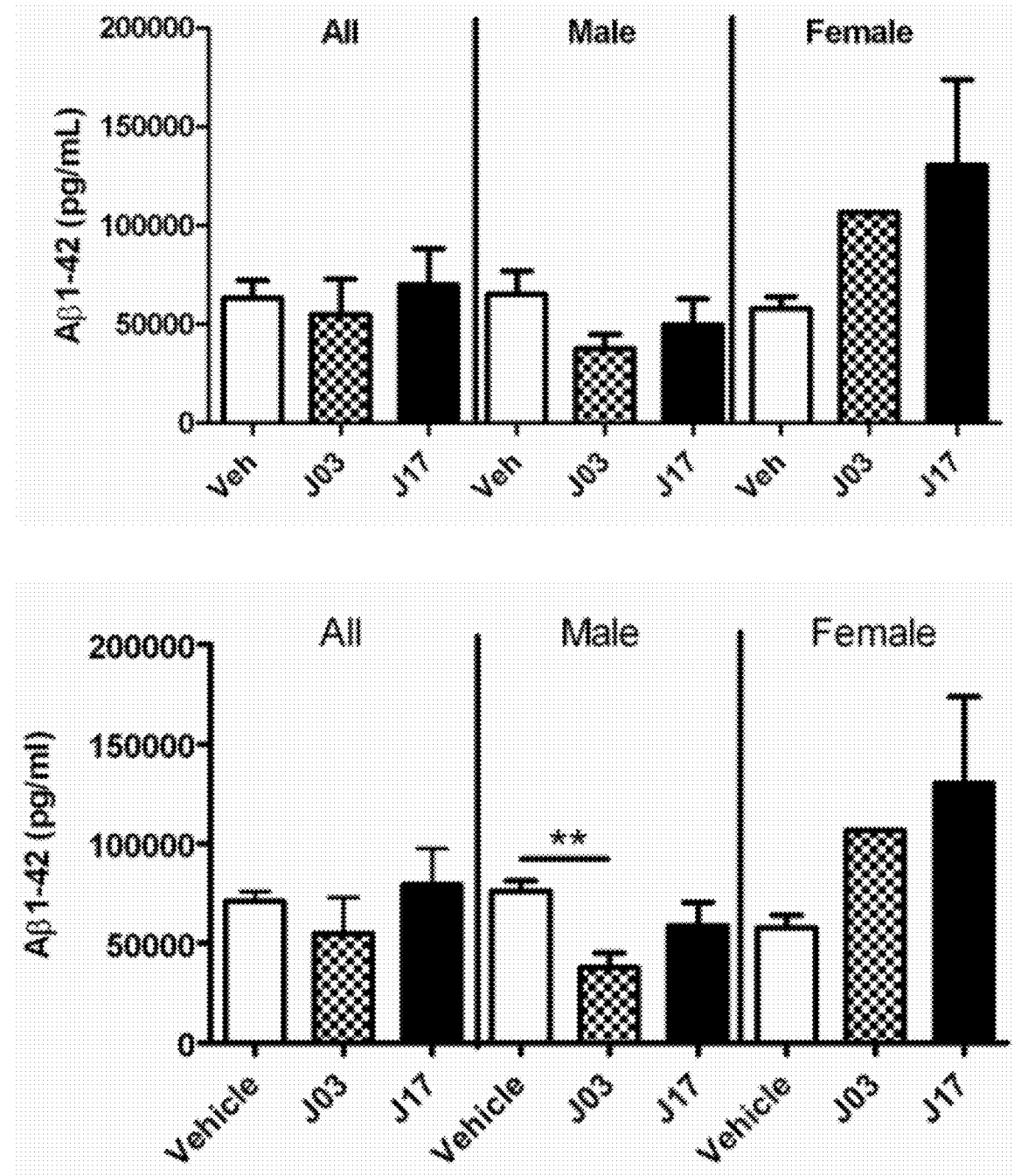
FIG. 24 illustrates the effect of J03 and J17 on Aβ1-42.
Figure 25:
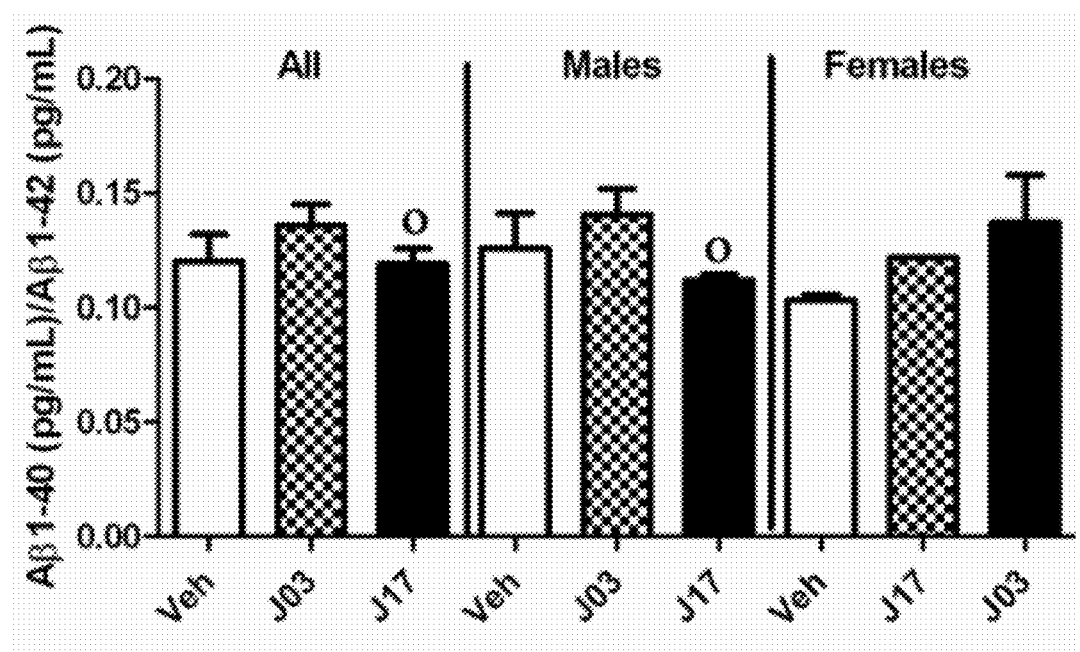
FIG. 25 illustrates the effect of J03 and J17 on the Aβ1-40/Aβ1-42 ratio broken out by gender with outliers removed.

When data from all mice are presented (FIG. 24, top panel), there are no significant differences in Aβ1-42, but when the low outlier (10-fold lower) from one sibling pair was eliminated, there is a significant reduction in Aβ1-42 in male mice (FIG. 24, bottom panel). Even with low outliers eliminated, there was no significant difference in the Aβ1-40/Aβ1-42 ratio (FIG. 25).

Figure 26:
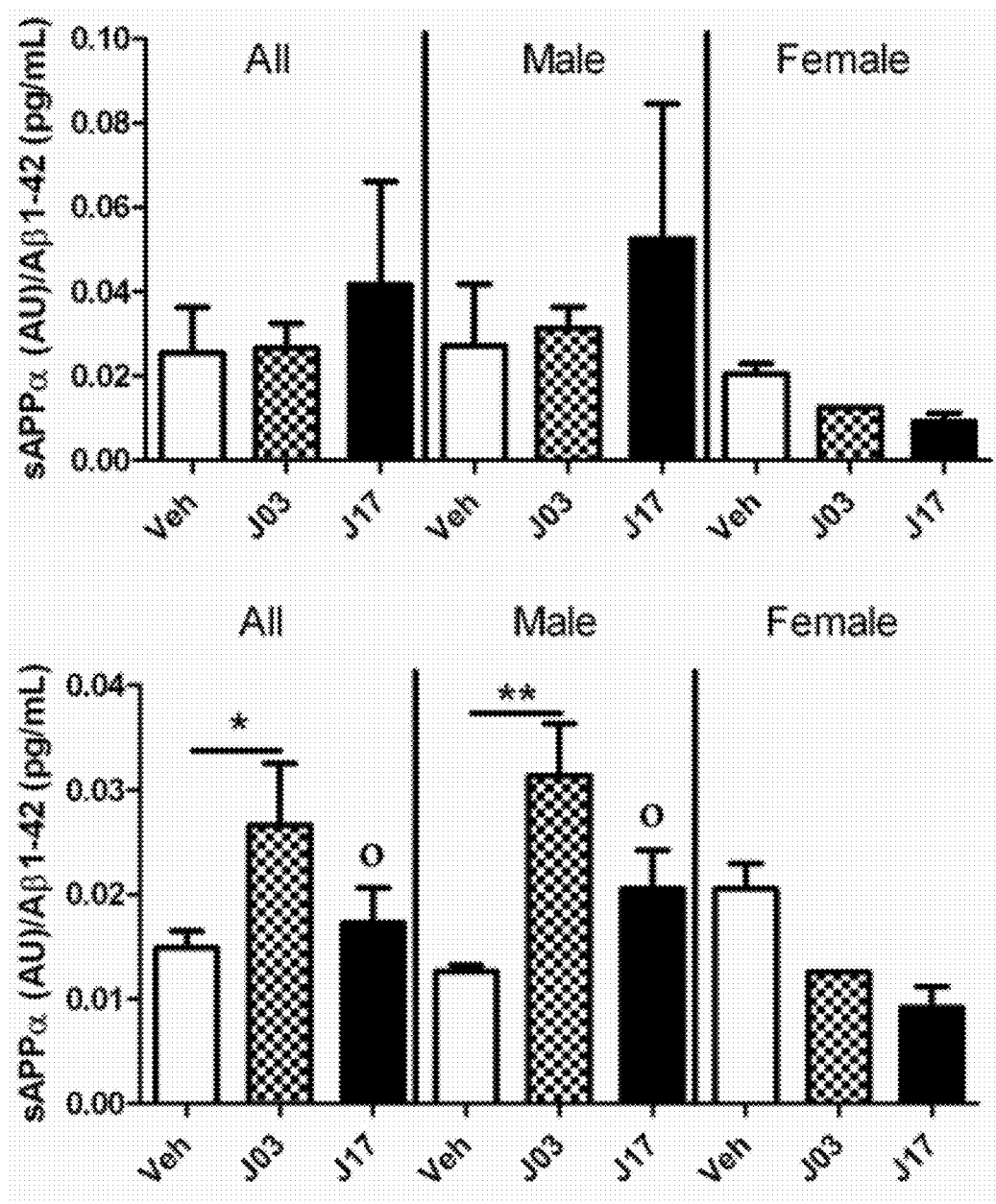
FIG. 26 illustrates the effect of J03 and J17 on the sAPPα/Aβ1-42 ratio broken out by gender with outliers included (top panel) and with outliers removed (bottom panel).

FIG. 26 A 1-42. When data from all mice are presented (top), there are no significant differences in Aβ1-42 (FIG. 26, top), but when the low outlier (10-fold lower) from one sibling pair was eliminated, there was a significant reduction in Aβ1-42 in male mice (FIG. 26, bottom).

Figure 27:
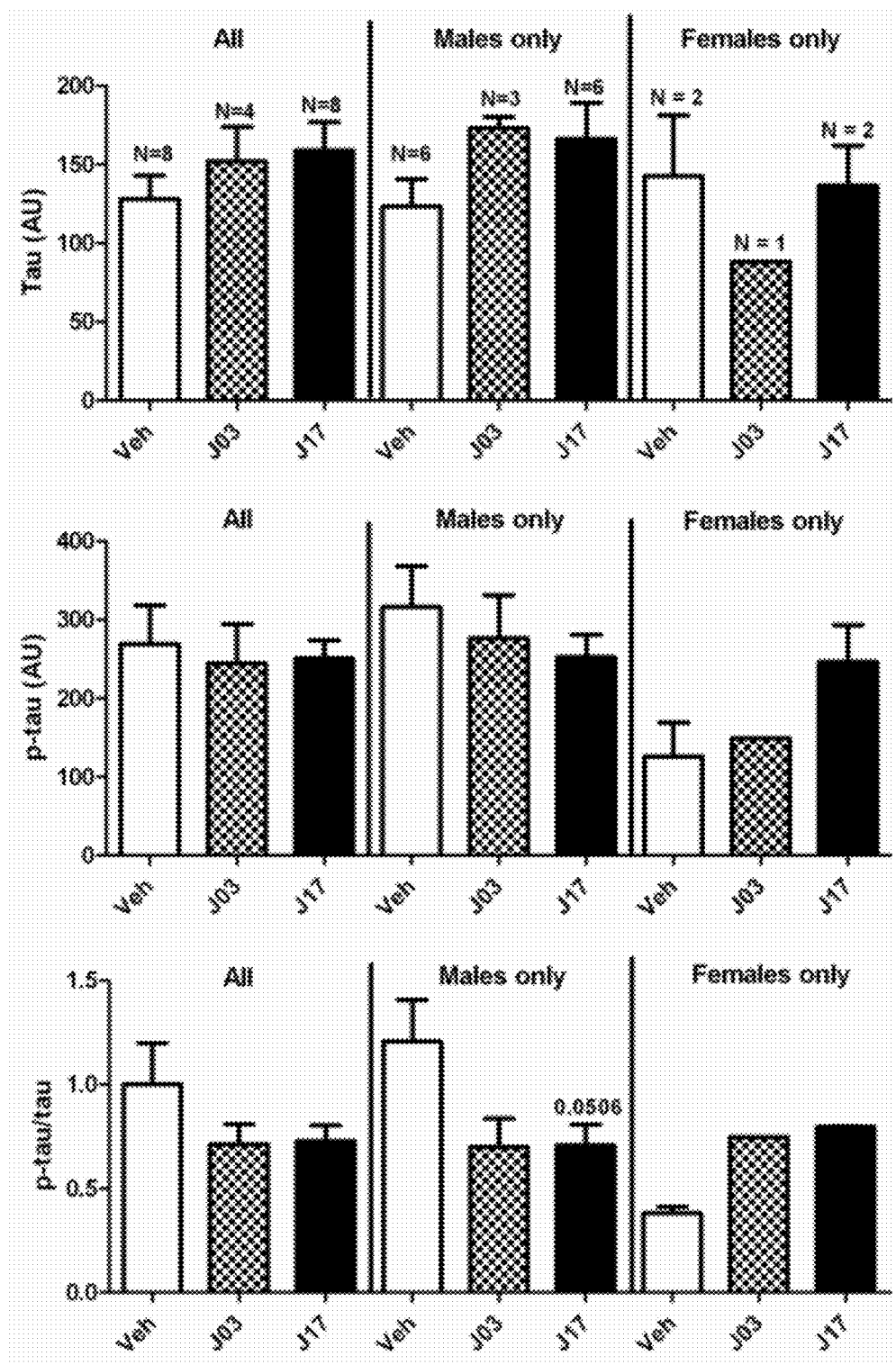
FIG. 27 illustrates the effects of J03 and J17 on the values of tau (top panel), p-tau (middle panel), and the ration p-tau/tau (lower panel) broken out by gender.

Tau (FIG. 27, top panel) was increased in males, but an important readout for this series of compounds, p-tau, was slightly lower in male mice (FIG. 27 middle panel) and the p-tau/tau ratio (FIG. 27, bottom panel) was lower still and just missed significance for J17-treated males.

J19 studies.

Figure 28:
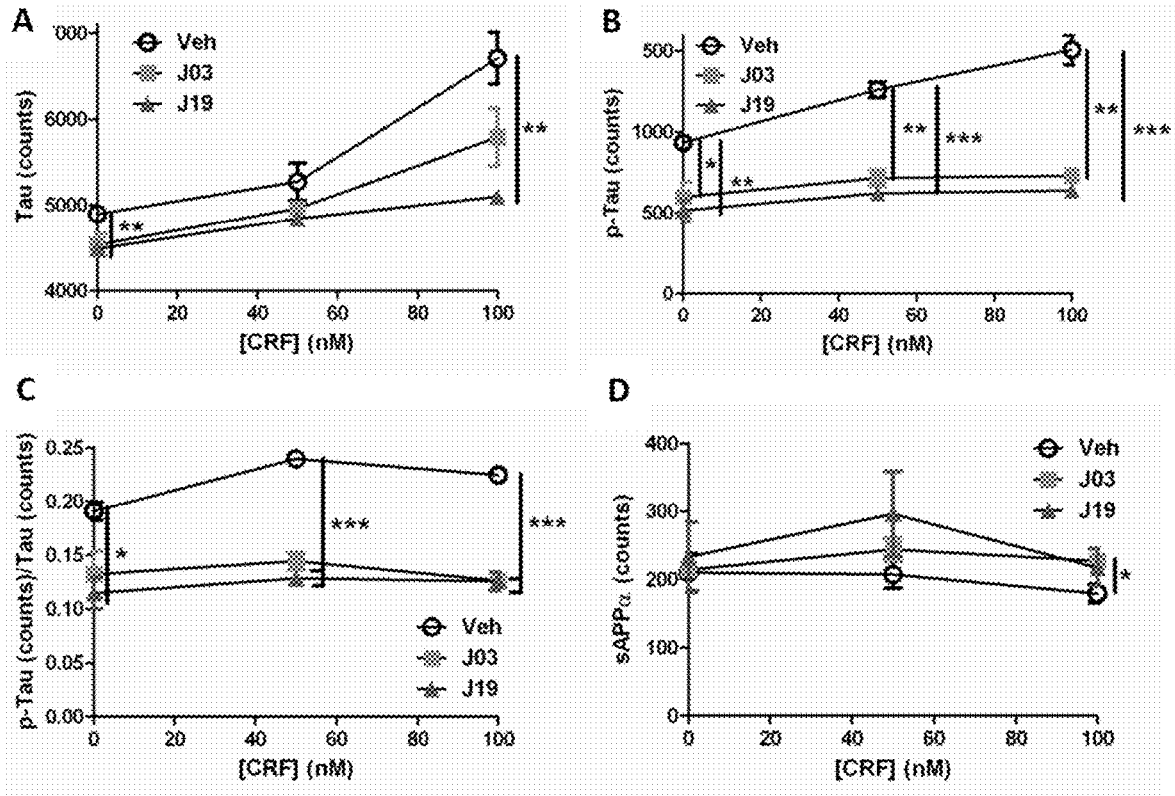
FIG. 28, panels A-D illustrate the effect of J03 and J19 on CRF-induced tau and p-tau alterations. Panel A: tau; Panel B: p-tau; Panel C: p-tau/tau ratio; Panel D: sAppα.

J19 (see FIG. 2) is an analog of J03 similar to J17 and is part of the triazolopyrimidine series described herein. FIG. 28, panels A-D, illustrates the effect of J03 and J19 on CRF-induced tau and p-tau alterations. J03 significantly decreased tau both in the absence of CRF and in the presence of 100 nM CRF (panel A). J19 also showed a trend to decrease tau. Both J03 and J19 significantly reduced p-tau in the presence and absence of CRF (panel B). The p-tau/tau ratios were highly significantly decreased by J03 and J19 at both 50 and 100 nM CRF, and were decreased in the absence of CRF (panel C). There was a trend for sAPPα to be higher with J03 and J19 that reached significance for J03 at 100 nM CRF (panel D).

Figure 29:
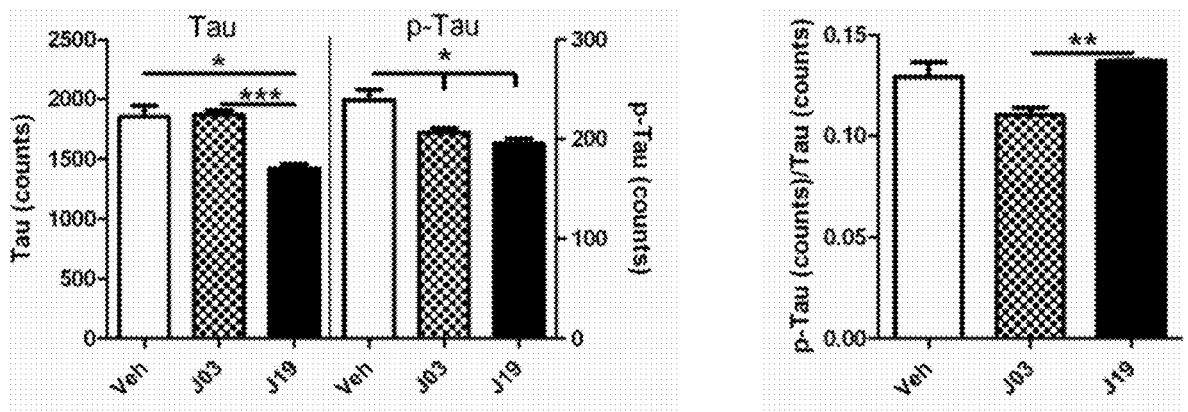
FIG. 29 illustrates the effect of J19 on tau (left panel), p-tau (left panel), and the ratio (right panel).

J19 decreased tau and both J03 and J19 decreased p-tau (FIG. 29, left panel). Therefore, while the p-tau/tau ratio looks unchanged for J19 FIG. 29, right panel). This is due to the tau decrease and not due to a lack of effect.

Figure 30:
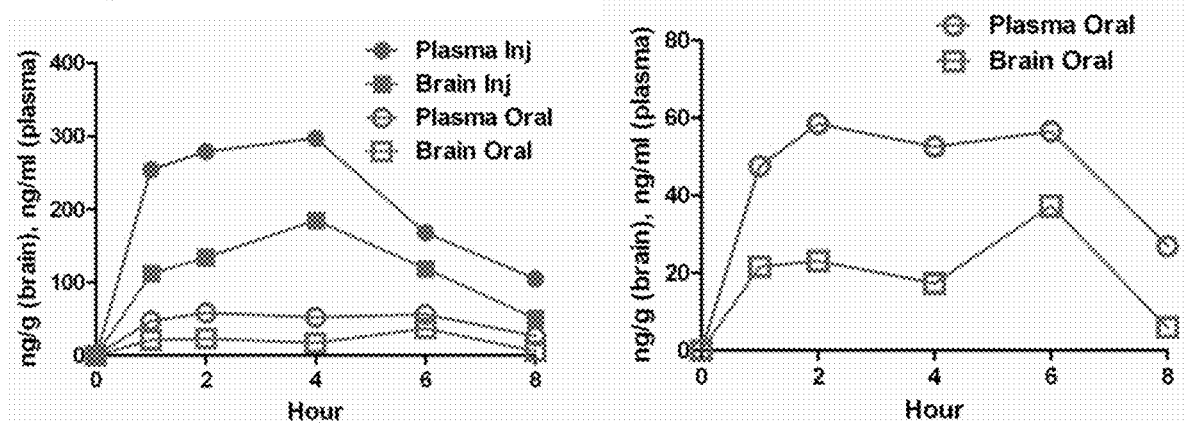
FIG. 30 illustrates the in vivo pharmacokinetics of J19.

FIG. 30 illustrates the in vivo pharmacokinetics of J19. After SQ injection of J19 at 10 mkd, brain levels were ~190 ng/g at the peak 4 hours after injection. Levels remained relatively high until 8 hours (left panel). With oral delivery (right panel), levels were much lower, but again remained detectable from 1 to 6 hours.

REFERENCES

Precursor Protein Processing to Preclude Amyloid Beta and Also Reduces Tau Pathology. *Biol. Psychiatry* 2013 Jan. 8.

Bredesen, 2009

Brunson K. L., Grigoriadis D. E., Lorang M T, Baram T Z. Corticotropin-Releasing Hormone (CRH) Downregulates the Function of Its Receptor (CRF1) and Induces CRF1 Expression in Hippocampal and Cortical Regions of the Immature Rat Brain. *Experimental Neurology* July 2002 176 (1):75-86.

Carroll J C, Iba M, Bangasser D A, Valentino R J, James M J, Brunden K R, Lee V M, Trojanowski J Q. Chronic stress exacerbates tau pathology, neurodegeneration, and cognitive performance through a corticotropin-releasing factor receptor-dependent mechanism in a transgenic mouse model of tauopathy. *J. Neurosci.* 2011 Oct. 5; 31(40):14436-14449.

Chen Y, Bender R A, Brunson K L, Pomper J K, Grigoriadis D E, Wurst W, Baram T Z. Modulation of dendritic differentiation by corticotropin-releasing factor in the developing hippocampus. *Proc. Natl. Acad. Sci. USA,* 2004. 101(44): 15782-15787.

Dong H, Goico B, Martin M, Csernansky C A, Berchume A, Csernansky J G Modulation of hippocampal cell proliferation, memory, and amyloid plaque deposition in APPsw (Tg2576) mutant mice by isolation stress. *Neuroscience* 127 (2004) 601-609

Dong H, Yuede C M, Yoo H-S, Martin M V, Deal C, Mace A G, Csernansky G J Corticosterone and related receptor expression are associated with increased β-amyloid plaques in isolated Tg2576 mice. *Neuroscience.* 2008 Jul. 31; 155(1):154-163.

Holtzman et al., 2011 Hsia A Y, Masliah E, McConlogue L, Yu G-Q, Tatsuno G, Hu K, Kholodenko D, Malenka R C, Nicoll R A, Mucke L. Plaque-independent disruption of neural circuits in Alzheimer's disease mouse models. *Proc. Natl. Acad. Sci. USA,* 1999 March Vol. 96, pp. 3228-3233

Kang J-E, Cirrito J R, Dong H, Csernansky J G, Holtzman D M. Acute stress increases interstitial fluid amyloid-beta via corticotropin-releasing factor and neuronal activity. *Proc. Natl. Acad. Sci. USA,* Jun. 19 2007 104(25): 10673-10678

Karagkouni A, Alevizos M, Theoharides T C. Effect of stress on brain inflammation and multiple sclerosis. *Autoimmun. Rev.* 2013 Mar. 25 (13)00043-48.

Klunk W E, Mathis C A, Price J C, Lopresti B J, DeKosky S T. Two-year follow-up of amyloid deposition in patients with Alzheimer's disease. *Brain.* 2006 November; 129(Pt 11):2805-2807.

Macor J E, Gurley D, Lanthorn T, Loch J, Mack R A, Mullen G, Tran O, Wright N, Gordon J C. The 5-HT3 antagonist tropisetron (ICS 205-930) is a potent and selective alpha7 nicotinic receptor partial agonist. *Bioorg Med Chem Lett.* 2001 Feb. 12; 11(3):319-321.

Martisova E, Solas M, Gerenu G, Milagro F I, Campion J, Ramirez M J. Mechanisms involved in BACE upregulation associated to stress. *Curr. Alzheimer's Res.* 2012 September; 9(7):822-829.

McCarthy J R, Heinrichs S C, Grigoriadis DE. Recent advances with the CRF1 receptor: design of small molecule inhibitors, receptor subtypes and clinical indications. *Current Pharmaceutical Design.* 1999 May; 5(5): 289-315.

What is claimed is:

1. A compound of the formula:

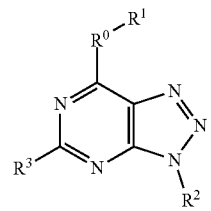

or a pharmaceutically acceptable salt, stereoisomer, or tautomer thereof, wherein:

$R^0$ is —NH— or —NCH$_3$—;

$R^1$ is

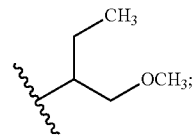 [SMILES: *C(CC)COC]

$R^2$ is

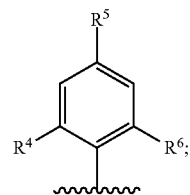

$R^3$ is —CH$_3$;

$R^4$ is —CH$_3$, —CH$_2$CH$_3$, —(CH$_2$)$_2$CH$_3$, or —(CH$_2$)$_3$CH$_3$;

$R^5$ is —F, —Cl, or —I; and $R^6$ is —H.

2. The compound of claim 1, or a pharmaceutically acceptable salt, stereoisomer, or tautomer thereof, wherein $R^0$ is —NH—.

3. The compound of claim 1, or a pharmaceutically acceptable salt, stereoisomer, or tautomer thereof, wherein $R^0$ is —NCH$_3$—.

4. The compound of claim 1, or a pharmaceutically acceptable salt, stereoisomer, or tautomer thereof, wherein $R^4$ is —CH$_3$.

5. The compound of claim 1, or a pharmaceutically acceptable salt, stereoisomer, or tautomer thereof, wherein $R^5$ is —Cl.

6. The compound of claim 1, or a pharmaceutically acceptable salt, stereoisomer, or tautomer thereof, wherein:

$R^4$ is —CH$_3$ or —CH$_2$CH$_3$; and $R^5$ is —F or —Cl.

7. The compound of claim 1, wherein the compound is:

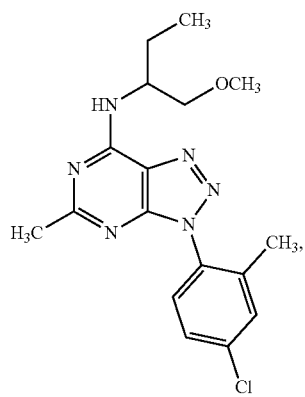

or a pharmaceutically acceptable salt, stereoisomer, or tautomer thereof.

8. The compound of claim 1, or a pharmaceutically acceptable salt, stereoisomer, or tautomer thereof, wherein the stereoisomer is an (S)-enantiomer or an (R)-enantiomer.

9. A pharmaceutical formulation comprising a pharmaceutically acceptable carrier or excipient and a compound of claim 1, or a pharmaceutically acceptable salt, stereoisomer, or tautomer thereof.

10. A compound:

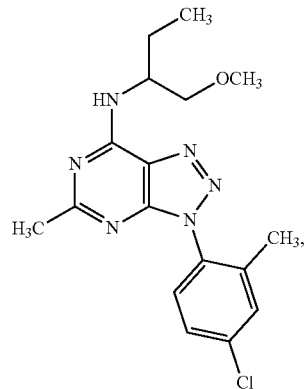

or a pharmaceutically acceptable salt, stereoisomer, or tautomer thereof.

11. A pharmaceutical formulation comprising a pharmaceutically acceptable carrier or excipient and the compound:

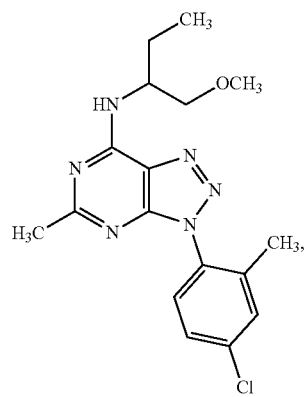

or a pharmaceutically acceptable salt, stereoisomer, or tautomer thereof.

* * * * *